United States Patent
Ikeda et al.

(10) Patent No.: US 11,827,601 B2
(45) Date of Patent: *Nov. 28, 2023

(54) HETEROCYCLIC NMDA ANTAGONISTS

(71) Applicant: TAKEDA PHARMACEUTICAL COMPANY LIMITED, Osaka (JP)

(72) Inventors: Shuhei Ikeda, Fujisawa (JP); Makoto Kamata, Fujisawa (JP); Yuya Oguro, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/087,302

(22) Filed: Dec. 22, 2022

(65) Prior Publication Data
US 2023/0134307 A1    May 4, 2023

Related U.S. Application Data

(63) Continuation of application No. 17/755,907, filed as application No. PCT/IB2020/000962 on Nov. 12, 2020.

(30) Foreign Application Priority Data

Nov. 14, 2019   (JP) ................................. 2019-206311

(51) Int. Cl.
 *C07D 207/263* (2006.01)
 *A61P 25/18* (2006.01)
 *C07D 401/06* (2006.01)

(52) U.S. Cl.
 CPC .......... *C07D 207/263* (2013.01); *A61P 25/18* (2018.01); *C07D 401/06* (2013.01)

(58) Field of Classification Search
 CPC ................................................ C07D 207/263
 See application file for complete search history.

(56) References Cited

U.S. PATENT DOCUMENTS

| | | | |
|---|---|---|---|
| 6,420,415 B1 | 7/2002 | Yamashita et al. | |
| 11,471,428 B2 | 10/2022 | Hu et al. | |
| 2005/0165064 A1 | 7/2005 | Kajino et al. | |
| 2023/0002318 A1 | 1/2023 | Ikeda et al. | |
| 2023/0150934 A1 | 5/2023 | Ikeda et al. | |

FOREIGN PATENT DOCUMENTS

| | | | |
|---|---|---|---|
| AU | 2019204448 B2 | 6/2019 | |
| AU | 2021225156 B2 | 8/2021 | |
| EP | 1 500 658 A1 | 1/2005 | |
| WO | WO 01/30330 A2 | 5/2001 | |
| WO | WO 2007/075387 A1 | 7/2007 | |
| WO | WO-2007078523 A2 * | 7/2007 | ........... C07D 263/20 |
| WO | WO 2009/004430 A1 | 1/2009 | |
| WO | WO-2009004430 A1 * | 1/2009 | ........... C07D 241/08 |
| WO | WO 2015/127391 A1 | 2/2015 | |
| WO | WO 2020/081999 A1 | 4/2020 | |
| WO | WO 2020/198710 A1 | 10/2020 | |
| WO | WO 2021/094832 | 5/2021 | |

OTHER PUBLICATIONS

Caddy, C. et al., Ketamine as the prototype glutamatergic antidepressant: pharmacodynamic actions, and a systematic review and meta-analysis of efficacy. Therapeutic Advances in Psychopharmacology (Ther. Adv. Psychopharmacol.) vol. 4, p. 75-99, 2014.

Devonshire, Ian M. et al. Effects of urethane anaesthesia on sensory processing in the rat barrel cortex revealed by combined optical imaging and electrophysiology, European Journal of Neuroscience (Eur. J. Neurosci.) vol. 32, p. 786-797, 2010.

Howlett, D et al., Inhibition of fibril formation in b-amyloid peptide by a novel series of benzofurans, Biochem. J. vol. 340 (1), p. 283-289, 1999.

Kandiah, N. et al., Cerebral white matter disease is independently associated with BPSD in Alzheimer's disease, Journal of the Neurological Sciences (J. Neurol. Sci.) vol. 337, p. 162-166, 2014.

Kim Y, Cho HY, Ahn YJ, et al. Effect of NMDA NR2B antagonist on neuropathic pain in two spinal cord injury models. Pain, vol. 153, p. 1022-1029, 2012.

Maidment, I. D. et al., Efficacy of Memantine on Behavioral and Psychological Symptoms Related to Dementia: A Systematic Meta-Analysis, The Annals of Pharmacotherapy (Ann. Pharmacother.) vol. 42, p. 32-38, 2007.

Peeters, M. et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics (J. Pharmacol. Exp. Ther.) vol. 321, p. 564-572, 2007.

Preskorn, S. H. et al., An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder, Journal of Clinical Psychopharmacology (J. Clin. Psychopharmacol.) vol. 28, p. 631-637, 2008.

(Continued)

*Primary Examiner* — David K O'Dell
(74) *Attorney, Agent, or Firm* — Finnegan, Henderson, Farabow, Garrett & Dunner LLP

(57) ABSTRACT

A compound of formula (I), or a salt thereof that may have an antagonistic action against an NMDA receptor that includes an NR2B subunit and may be useful as a prophylactic or therapeutic agent for depression, bipolar disorder, migraine, pain, a symptom peripheral to dementia, or the like.

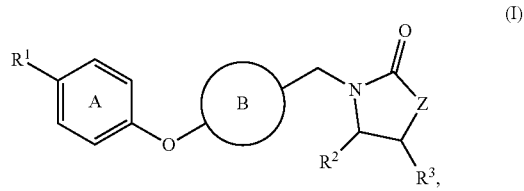

8 Claims, No Drawings

(56) References Cited

OTHER PUBLICATIONS

U.S. Appl. No. 17/755,907, filed May 11, 2022, Takeda Pharmaceutical Company Limited, only the specification, the claims, and drawings.
U.S. Appl. No. 18/087,233, filed Dec. 22, 2022, Takeda Pharmaceutical Company Limited, only the specification, the claims, and drawings.
International Search Report for International Application No. PCT/IB2020/000962, dated Mar. 11, 2021 (three pages).

* cited by examiner

HETEROCYCLIC NMDA ANTAGONISTS

This application is a continuation of U.S. patent application Ser. No. 17/755,907, filed May 11, 2022, which is a national stage filing under 35 U.S.C. § 371 of International Application No. PCT/IB2020/000962, filed Nov. 12, 2020, which claims the benefit of priority to Japanese Patent Application No. 2019-206311, filed Nov. 14, 2019, the contents of each of which are incorporated by reference herein in their entirety.

The present disclosure relates to heterocyclic compounds that may have an antagonistic action on an N-methyl-D-aspartic acid (NMDA) receptor containing an NR2B subunit and may be useful as prophylactic or therapeutic agents for depression, bipolar disorder, migraine, pain, peripheral symptoms of dementia, or the like.

The major excitatory neurotransmitter in the central nervous system (such as the brain and spinal cord) is glutamic acid, and the signal transduction thereof is carried out by the ion channel-conjugated receptor N-methyl-D-aspartic acid (NMDA) receptor, the gamma-amino-3-hydroxy-5-methyl-oxazole-4-propionic acid (AMPA)/kainic acid (KA) receptor, and the metabotropic glutamate receptor. Among these, the NMDA receptor has high permeability to certain cations, including calcium ions, and mediates excitatory neurotransmission by depolarization of the nerve cells. In addition, calcium that has flowed into the cell via the NMDA receptor functions as a secondary messenger and causes plastic changes in the nerve function via actions such as changes in intracellular phosphorylation signals and regulation of gene transcription and translation, and thus the NMDA receptors play an important role in the regulation of central nervous system function.

The NMDA receptor is a receptor composed of a tetramer in which two or three subunits from among NR1, NR2A, NR2B, NR2C, NR2D, NR3A, and NR3B subunits are associated, and the presence of the NR1 subunit is believed to be essential to its function as a receptor for carrying out the excitatory neurotransmission. Since the NR1 subunit is included in functional NMDA receptors, it is widely distributed in the central nervous system. On the other hand, the distribution and expression timing of the NR2 subunit are different for each subunit. For example, the NR2A and NR2C subunits are detected for the first time immediately before birth, while the NR2B and NR2D subunits are observed from the early stage of fetal development. Moreover, for example, the NR2A subunit is widely distributed in the brain, while the NR2B subunit is locally expressed in the forebrain, and the NR2C subunit is locally expressed in the cerebellum.

The NMDA receptor containing the NR2B subunit, the target of the present disclosure, is highly expressed in the cerebral cortex (particularly layers 2 and 3), hippocampus, amygdala, ventral nucleus of thalamus, and olfactory bulb in the adult rodent brain. Also, the receptor is confined to the posterior horn of the spinal cord, particularly the second layer. In addition, in the single cell, the NMDA receptor containing the NR2B subunit is most highly expressed in postsynaptic density and expression thereof is also observed in the extrasynaptic region. This suggests that the NMDA receptor containing the NR2B subunit is functional widely in the brain and may be effective in the prophylaxis or treatment of central nervous system diseases.

The present disclosure provides heterocyclic compounds, and pharmaceutical compositions comprising the same, that may have an antagonistic action on an NMDA receptor containing an NR2B subunit and may be useful as prophylactic or therapeutic agents for depression, bipolar disorder, migraine, pain, peripheral symptoms of dementia, or the like.

Disclosed herein are: [1] A compound of formula (I):

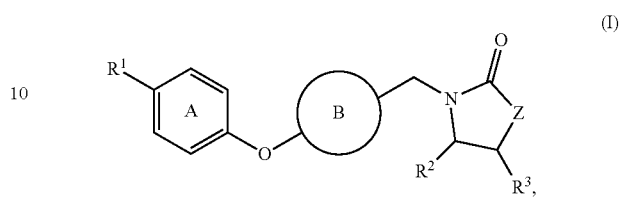

or a salt thereof (which may be abbreviated herein as "compound (I)"), wherein:

$R^1$ is chosen from halogens and $C_{1-3}$ alkyl groups optionally substituted with at least one fluorine;

$R^2$ is chosen from $C_{1-3}$ alkyl groups optionally substituted with at least one fluorine;

$R^3$ is chosen from hydrogen and hydroxy groups;

ring A is chosen from optionally substituted benzene groups;

ring B is chosen from groups of the following formulas:

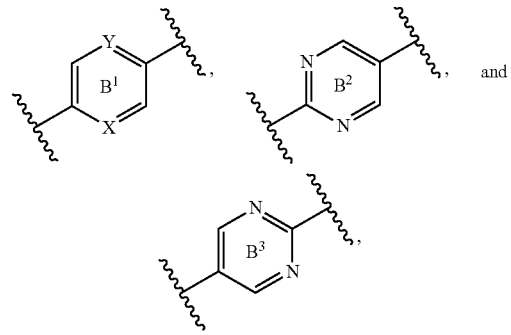

wherein:

X and Y are each independently chosen from carbon and nitrogen;

ring $B^1$ is chosen from optionally substituted benzene groups, optionally substituted pyridine groups, and optionally substituted pyrazine groups;

ring $B^2$ is chosen from optionally substituted pyrimidine groups; and ring $B^3$ is chosen from optionally substituted pyrimidine groups; and Z is chosen from $CH_2$, $CF_2$, O, and NH.

Also disclosed herein is [2] the compound according to [1] or a salt thereof, wherein:

$R^1$ is chosen from halogens and $C_{1-3}$ alkyl groups optionally substituted with one to three fluorine;

$R^2$ is chosen from $C_{1-3}$ alkyl groups optionally substituted with one to three fluorine;

$R^3$ is chosen from hydrogen and hydroxyl groups;

ring A is chosen from benzene groups optionally substituted with one to four halogens;

ring B is chosen from groups of the following formulas:

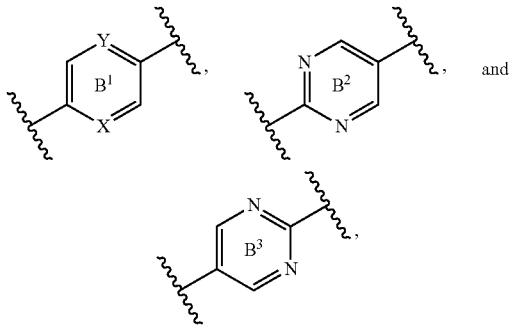

wherein:
X and Y are each independently chosen from carbon and nitrogen;
ring $B^1$ is chosen from an unsubstituted benzene group, unsubstituted pyridine groups, and an unsubstituted pyrazine group;
ring $B^2$ is an unsubstituted pyrimidine group; and
ring $B^3$ is an unsubstituted pyrimidine group; and
Z is chosen from $CH_2$, $CF_2$, O, and NH.

Also disclosed herein is [3] the compound according to [1] or a salt thereof, wherein:
$R^1$ is chosen from halogens and $C_{1-3}$ alkyl groups optionally substituted with one or two fluorine;
$R^2$ is chosen from unsubstituted $C_{1-3}$ alkyl groups;
$R^3$ is chosen from hydrogen and hydroxyl groups;
ring A is chosen from benzene groups optionally substituted with one or two halogens;
ring B is chosen from groups of the following formulas:

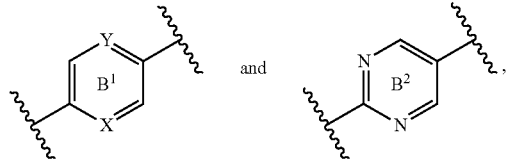

wherein:
one of X and Y is carbon and the other is nitrogen;
ring $B^1$ is chosen from unsubstituted pyridine groups; and
ring $B^2$ is an unsubstituted pyrimidine group; and
Z is $CH_2$ or O.

Also disclosed herein is [4] the compound according to [1] or a salt thereof, wherein:
$R^1$ is chosen from halogens and $C_{1-3}$ alkyl groups optionally substituted with one or two fluorine;
$R^2$ is chosen from unsubstituted $C_{1-3}$ alkyl groups;
$R^3$ is chosen from hydrogen and hydroxyl groups;
ring A is chosen from groups of the formula:

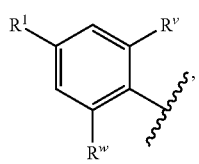

wherein:
$R^v$ is chosen from halogens; and
$R^w$ is chosen from hydrogen and halogens;
ring B is chosen from groups of the following formulas:

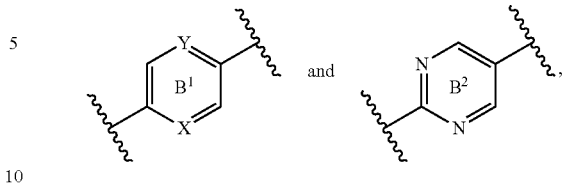

wherein:
one of X and Y is carbon and the other is nitrogen;
ring $B^1$ is chosen from unsubstituted pyridine groups; and
ring $B^2$ is an unsubstituted pyrimidine group; and
Z is $CH_2$ or O.

Also disclosed herein is [5] (4S,5S)-1-({6-[4-(difluoromethyl)-2-fluorophenoxy]pyridin-3-yl}methyl)-4-hydroxy-5-methylpyrrolidine-2-one and salts thereof.

Also disclosed herein are [6] (5S)-1-{[2-(2,4-difluorophenoxy)pyrimidin-5-yl]methyl}-5-methylpyrrolidine-2-one and salts thereof.

Also disclosed herein are [7] (4S)-3-{[2-(4-chloro-2-fluorophenoxy)pyrimidin yl]methyl}-4-methyl-1,3-oxazolidine-2-one and salts thereof.

Also disclosed herein are [8] pharmaceutical compositions comprising at least one entity chosen from compounds according to [1] and salts thereof.

Also disclosed herein are [9] pharmaceutical compositions according to [8], wherein the at least one entity is an antagonist of an NMDA receptor containing an NR2B subunit.

Also disclosed herein are [10] pharmaceutical compositions according to [8], wherein the at least one entity is a prophylactic or therapeutic agent for depression, bipolar disorder, migraine, pain, or peripheral symptoms of dementia.

Also disclosed herein is [11] the compound according to [1] or a salt thereof for use in prevention or treatment of depression, bipolar disorder, migraine, pain, or peripheral symptoms of dementia.

Also disclosed herein is [12] a method for antagonizing an NMDA receptor containing an NR2B subunit in a mammal, comprising administering an effective dose of at least one entity chosen from compounds according to [1] and salts thereof to the mammal.

Also disclosed herein is [13] a method for preventing or treating depression, bipolar disorder, migraine, pain, or peripheral symptoms of dementia in a mammal, comprising administering an effective dose of at least one entity chosen from compounds according to [1] and salts thereof to the mammal.

Also disclosed herein is [14] use of at least one compound chosen from compounds according to [1] and salts thereof in the manufacture of a prophylactic or therapeutic agent for the treatment of depression, bipolar disorder, migraine, pain, or peripheral symptoms of dementia.

The present disclosure provides heterocyclic compounds and pharmaceutical compositions comprising the same that may have an antagonistic effect on the NMDA receptor containing the NR2B subunit and may be useful as prophylactic or therapeutic agents for depression, bipolar disorder, migraine, pain, peripheral symptoms of dementia, or the like.

The definition of each substituent used in the present Specification is described in detail below. Each substituent has the following definitions unless otherwise specified.

Non-limiting examples of "halogens" include fluorine, chlorine, bromine, and iodine.

In the present Specification, non-limiting examples of "$C_{1-6}$ alkyl groups" include a methyl group, an ethyl group, a propyl group, an isopropyl group, a butyl group, an isobutyl group, a sec-butyl group, a tert-butyl group, a pentyl group, an isopentyl group, a neopentyl group, a 1-ethylpropyl group, a hexyl group, an isohexyl group, a 1,1-dimethyl butyl group, a 2,2-dimethyl butyl group, a 3,3-dimethyl butyl group, and a 2-ethyl butyl group.

In the present Specification, "$C_{1-6}$ alkyl groups optionally substituted with at least one halogen" include, but are not limited to, $C_{1-6}$ alkyl groups that may be substituted with one to seven, such as, e.g., one to five, halogens. Non-limiting examples include a methyl group, a chloromethyl group, a difluoromethyl group, a trichloromethyl group, a trifluoromethyl group, an ethyl group, a 2-bromoethyl group, a 2,2,2-trifluoroethyl group, a tetrafluoroethyl group, a pentafluoroethyl group, a propyl group, a 2,2-difluoropropyl group, a 3,3,3-trifluoropropyl group, an isopropyl group, a butyl group, a 4,4,4-trifluorobutyl group, an isobutyl group, a sec-butyl group, a tert-butyl group, a pentyl group, an isopentyl group, a neopentyl group, a 5,5,5-trifluoropentyl group, a hexyl group, and a 6,6,6-trifluorohexyl group.

In the present Specification, non-limiting examples of "$C_{2-6}$ alkenyl groups" include an ethenyl group, a 1-propenyl group, a 2-propenyl group, a 2-methyl-1-propenyl group, a 1-butenyl group, a 2-butenyl group, a 3-butenyl group, a 3-methyl-2-butenyl group, a 1-pentenyl group, a 2-pentenyl group, a 3-pentenyl group, a 4-pentenyl group, a 4-methyl-3-pentenyl group, a 1-hexenyl group, a 3-hexenyl group, and a 5-hexenyl group.

In the present Specification, non-limiting examples of "$C_{2-6}$ alkynyl groups" include an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, a 5-hexynyl group, and a 4-methyl-2-pentynyl group.

In the present Specification, non-limiting examples of "$C_{3-10}$ cycloalkyl groups" include a cyclopropyl group, a cyclobutyl group, a cyclopentyl group, a cyclohexyl group, a cycloheptyl group, a cyclooctyl group, a bicyclo[2.2.1]heptyl group, a bicyclo[2.2.2] octyl group, a bicyclo [3.2.1] octyl group, and an adamantyl group.

In the present Specification, "optionally halogenated $C_{3-10}$ cycloalkyl groups" (i.e., "$C_{3-10}$ cycloalkyl groups optionally substituted with at least one halogen") include, but are not limited to, $C_{3-10}$ cycloalkyl groups that may be substituted with one to seven, such as, e.g., one to five, halogens. Non-limiting examples include a cyclopropyl group, a 2,2-difluorocyclopropyl group, a 2,3-difluorocyclopropyl group, a cyclobutyl group, a difluorocyclobutyl group, a cyclopentyl group, a cyclohexyl group, a cycloheptyl group, and a cyclooctyl group.

In the present Specification, non-limiting examples of "$C_{3-10}$ cycloalkenyl groups" include a cyclopropenyl group, a cyclobutenyl group, a cyclopentenyl group, a cyclohexenyl group, a cycloheptenyl group, and a cyclooctenyl group.

In the present Specification, non-limiting examples of "$C_{6-14}$ aryl groups" include a phenyl group, a 1-naphthyl group, a 2-naphthyl group, a 1-anthryl group, a 2-anthryl group, and a 9-anthryl group.

In the present Specification, non-limiting examples of "$C_{7-16}$ aralkyl groups" include a benzyl group, a phenethyl group, a naphthylmethyl group, and a phenylpropyl group.

In the present Specification, non-limiting examples of "$C_{1-6}$ alkoxy groups" include a methoxy group, an ethoxy group, a propoxy group, an isopropoxy group, a butoxy group, an isobutoxy group, a sec-butoxy group, a tert-butoxy group, a pentyloxy group, and a hexyloxy group.

In the present Specification, "optionally halogenated $C_{1-6}$ alkoxy groups" (i.e., "$C_{1-6}$ alkoxy groups optionally substituted with at least one halogen") include, but are not limited to, $C_{1-6}$ alkoxy groups that may be substituted with one to seven, such as, e.g., one to five, halogens. Non-limiting examples include a methoxy group, a difluoromethoxy group, a trifluoromethoxy group, an ethoxy group, a 2,2,2-trifluoroethoxy group, a propoxy group, an isopropoxy group, a butoxy group, a 4,4,4-trifluorobutoxy group, an isobutoxy group, a sec-butoxy group, a pentyloxy group, and a hexyloxy group.

In the present Specification, non-limiting examples of "$C_{3-10}$ cycloalkyloxy groups" include a cyclopropyloxy group, a cyclobutyloxy group, a cyclopentyloxy group, a cyclohexyloxy group, a cycloheptyloxy group, and a cyclooctyloxy group.

In the present Specification, non-limiting examples of "$C_{1-6}$ alkylthio groups" include a methylthio group, an ethylthio group, a propylthio group, an isopropylthio group, a butylthio group, a sec-butylthio group, a tert-butylthio group, a pentylthio group, and a hexylthio group.

In the present Specification, "optionally halogenated $C_{1-6}$ alkylthio groups" (i.e., "$C_{1-6}$ alkylthio groups optionally substituted with at least one halogen") include, but are not limited to, $C_{1-6}$ alkylthio groups that may be substituted with one to seven, such as, e.g., one to five, halogens. Non-limiting examples include a methylthio group, a difluoromethylthio group, a trifluoromethylthio group, an ethylthio group, a propylthio group, an isopropylthio group, a butylthio group, a 4,4,4-trifluorobutylthio group, a pentylthio group, and a hexylthio group.

In the present Specification, non-limiting examples of "$C_{1-6}$ alkyl-carbonyl groups" include an acetyl group, a propanoyl group, a butanoyl group, a 2-methylpropanoyl group, a pentanoyl group, a 3-methylbutanoyl group, a 2-methylbutanoyl group, a 2,2-dimethylpropanoyl group, a hexanoyl group, and a heptanoyl group.

In the present Specification, "$C_{1-6}$ alkyl-carbonyl groups that may be halogenated" (i.e., "$C_{1-6}$ alkyl-carbonyl groups optionally substituted with at least one halogen") include, but are not limited to, $C_{1-6}$ alkyl-carbonyl groups that may be substituted with one to seven, such as, e.g., one to five, halogens. Non-limiting examples include an acetyl group, a chloroacetyl group, a trifluoroacetyl group, a trichloroacetyl group, a propanoyl group, a butanoyl group, a pentanoyl group, and a hexanoyl group.

In the present Specification, non-limiting examples of "$C_{1-6}$ alkoxy-carbonyl groups" include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, and a hexyloxycarbonyl group.

In the present Specification, non-limiting examples of "$C_{6-14}$ aryl-carbonyl groups" include a benzoyl group, a 1-naphthoyl group, and a 2-naphthoyl group.

In the present Specification, non-limiting examples of "$C_{7-16}$ aralkyl-carbonyl groups" include a phenylacetyl group and a phenylpropionyl group.

In the present Specification, non-limiting examples of "5- to 14-membered aromatic heterocyclic carbonyl groups" include a nicotinoyl group, an isonicotinoyl group, a tenoyl group, and a furoyl group.

In the present Specification, non-limiting examples of "3- to 14-membered non-aromatic heterocyclic carbonyl groups" include a morpholinylcarbonyl group, a piperidinylcarbonyl group, and a pyrrolidinylcarbonyl group.

In the present Specification, non-limiting examples of "mono- or di-$C_{1-6}$ alkyl-carbamoyl groups" include a methylcarbamoyl group, an ethylcarbamoyl group, a dimethylcarbamoyl group, a diethylcarbamoyl group, and an N-ethyl-N-methylcarbamoyl group.

In the present Specification, non-limiting examples of "mono- or di-$C_{7-16}$ aralkyl-carbamoyl groups" include a benzylcarbamoyl group and a phenethylcarbamoyl group.

In the present Specification, non-limiting examples of "$C_{1-6}$ alkylsulfonyl groups" include a methylsulfonyl group, an ethylsulfonyl group, a propylsulfonyl group, an isopropylsulfonyl group, a butylsulfonyl group, a sec-butylsulfonyl group, and a tert-butylsulfonyl group.

In the present Specification, non-limiting examples of "$C_{1-6}$ alkylsulfonyl groups that may be halogenated" (i.e., "$C_{1-6}$ alkylsulfonyl groups optionally substituted with at least one halogen") include, but are not limited to, $C_{1-6}$ alkylsulfonyl groups that may be substituted with one to seven, such as, e.g., one to five, halogens. Non-limiting examples include a methylsulfonyl group, a difluoromethylsulfonyl group, a trifluoromethylsulfonyl group, an ethylsulfonyl group, a propylsulfonyl group, an isopropylsulfonyl group, a butylsulfonyl group, a 4,4,4-trifluorobutylsulfonyl group, a pentylsulfonyl group, and a hexylsulfonyl group.

In the present Specification, non-limiting examples of "$C_{6-14}$ arylsulfonyl groups" include a phenylsulfonyl group, a 1-naphthylsulfonyl group, and a 2-naphthylsulfonyl group.

In the present Specification, non-limiting examples of "substituents" include halogens, a cyano group, a nitro group, optionally substituted hydrocarbon groups, optionally substituted heterocyclic groups, acyl groups, optionally substituted amino groups, optionally substituted carbamoyl groups, optionally substituted thiocarbamoyl groups, optionally substituted sulfamoyl groups, optionally substituted hydroxy groups, optionally substituted sulfanyl (SH) groups, and optionally substituted silyl groups.

In the present Specification, non-limiting examples of "hydrocarbon groups" (including, e.g., "hydrocarbon groups" in "hydrocarbon groups that may be substituted" or "optionally substituted hydrogen carbon groups") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group, and a $C_{7-16}$ aralkyl group.

In the present Specification, non-limiting examples of "hydrocarbon groups that may be substituted" (i.e., "optionally substituted hydrocarbon groups") include hydrocarbon groups that may be substituted with at least one substituent chosen from the following substituent group A:

[Substituent Group A]
  (1) halogens;
  (2) a nitro group;
  (3) a cyano group;
  (4) an oxo group;
  (5) a hydroxy group;
  (6) $C_{1-6}$ alkoxy groups optionally substituted with at least one halogen;
  (7) $C_{6-14}$ aryloxy groups (such as, e.g., a phenoxy group or a naphthoxy group);
  (8) $C_{7-16}$ aralkyloxy groups (such as, e.g., a benzyloxy group);
  (9) 5- to 14-membered aromatic heterocyclic oxy groups (such as, e.g., a pyridyloxy group);
  (10) 3- to 14-membered non-aromatic heterocyclic oxy groups (such as, e.g., a morpholinyloxy group and a piperidinyloxy group);
  (11) $C_{1-6}$ alkyl-carbonyloxy groups (such as, e.g., an acetoxy group or a propanoyloxy group);
  (12) $C_{6-14}$ aryl-carbonyloxy groups (such as, e.g., a benzoyloxy group, a 1-naphthoyloxy group, or a 2-naphthoyloxy group);
  (13) $C_{1-6}$ alkoxy-carbonyloxy groups (such as, e.g., a methoxycarbonyloxy group, an ethoxycarbonyloxy group, a propoxycarbonyloxy group, or a butoxycarbonyloxy group);
  (14) mono- or di-$C_{1-6}$ alkyl-carbamoyloxy groups (such as, e.g., a methylcarbamoyloxy group, an ethylcarbamoyloxy group, a dimethylcarbamoyloxy group, or a diethylcarbamoyloxy group);
  (15) $C_{6-14}$ aryl-carbamoyloxy groups (such as, e.g., a phenylcarbamoyloxy group or a naphthylcarbamoyloxy group);
  (16) 5- to 14-membered aromatic heterocyclic carbonyloxy groups (such as, e.g., a nicotinoyloxy group);
  (17) 3- to 14-membered non-aromatic heterocyclic carbonyloxy groups (such as, e.g., a morpholinylcarbonyloxy group or a piperidinylcarbonyloxy group);
  (18) $C_{1-6}$ alkylsulfonyloxy groups optionally substituted with at least one halogen (such as, e.g., a methylsulfonyloxy group or a trifluoromethylsulfonyloxy group);
  (19) $C_{6-14}$ arylsulfonyloxy groups optionally substituted with a $C_{1-6}$ alkyl group (such as, e.g., a phenylsulfonyloxy group or a toluenesulfonyloxy group);
  (20) $C_{1-6}$ alkylthio groups optionally substituted with at least one halogen;
  (21) 5- to 14-membered aromatic heterocyclic groups;
  (22) 3- to 14-membered non-aromatic heterocyclic groups;
  (23) a formyl group;
  (24) a carboxy group;
  (25) $C_{1-6}$ alkyl-carbonyl groups optionally substituted with at least one halogen;
  (26) $C_{6-14}$ aryl-carbonyl groups;
  (27) 5- to 14-membered aromatic heterocyclic carbonyl groups;
  (28) 3- to 14-membered non-aromatic heterocyclic carbonyl groups;
  (29) $C_{1-6}$ alkoxy-carbonyl groups;
  (30) $C_{6-14}$ aryloxy-carbonyl groups (such as, e.g., a phenyloxycarbonyl group, a 1-naphthyloxycarbonyl group, or a 2-naphthyloxycarbonyl group);
  (31) $C_{7-16}$ aralkyloxy-carbonyl groups (such as, e.g., a benzyloxycarbonyl group or a phenethyloxycarbonyl group);
  (32) a carbamoyl group;
  (33) a thiocarbamoyl group;
  (34) mono- or di-$C_{1-6}$ alkyl-carbamoyl groups;
  (35) $C_{6-14}$ aryl-carbamoyl groups (such as, e.g., a phenylcarbamoyl group);
  (36) 5- to 14-membered aromatic heterocyclic carbamoyl groups (such as, e.g., a pyridylcarbamoyl group or a thienylcarbamoyl group);
  (37) 3- to 14-membered non-aromatic heterocyclic carbamoyl groups (such as, e.g., a morpholinylcarbamoyl group or a piperidinylcarbamoyl group);
  (38) $C_{1-6}$ alkylsulfonyl groups optionally substituted with at least one halogen;

(39) $C_{6-14}$ arylsulfonyl groups;

(40) 5- to 14-membered aromatic heterocyclic sulfonyl groups (such as, e.g., a pyridylsulfonyl group or a thienylsulfonyl group);

(41) $C_{1-6}$ alkylsulfonyl groups optionally substituted with at least one halogen;

(42) $C_{6-14}$ arylsulfinyl groups (such as, e.g., a phenylsulfinyl group, a 1-naphthylsulfinyl group, or a 2-naphthylsulfinyl group);

(43) 5- to 14-membered aromatic heterocyclic sulfinyl groups (such as, e.g., a pyridylsulfinyl group or a thienylsulfinyl group);

(44) an amino group;

(45) mono- or di-$C_{1-6}$ alkylamino groups (such as, e.g., a methylamino group, an ethylamino group, a propylamino group, an isopropylamino group, a butylamino group, a dimethylamino group, a diethylamino group, a dipropylamino group, a dibutylamino group, or an N-ethyl-N-methylamino group);

(46) mono- or di-$C_{6-14}$ arylamino groups (such as, e.g., a phenylamino group);

(47) 5- to 14-membered aromatic heterocyclic amino groups (such as, e.g., a pyridylamino group);

(48) $C_{7-16}$ aralkylamino groups (such as, e.g., a benzylamino group);

(49) a formylamino group;

(50) $C_{1-6}$ alkyl-carbonylamino groups (such as, e.g., an acetylamino group, a propanoylamino group, or a butanoylamino group);

(51) ($C_{1-6}$ alkyl) ($C_{1-6}$ alkyl-carbonyl) amino groups (such as, e.g., an N-acetyl-N-methylamino group);

(52) $C_{6-14}$ aryl-carbonylamino groups (such as, e.g., a phenylcarbonylamino group or a naphthylcarbonylamino group);

(53) $C_{1-6}$ alkoxy-carbonylamino groups (such as, e.g., a methoxycarbonylamino group, an ethoxycarbonylamino group, a propoxycarbonylamino group, a butoxycarbonylamino group, or a tert-butoxycarbonylamino group);

(54) $C_{7-16}$ aralkyloxy-carbonylamino groups (such as, e.g., a benzyloxycarbonylamino group);

(55) $C_{1-6}$ alkylsulfonylamino groups (such as, e.g., a methylsulfonylamino group or an ethylsulfonylamino group);

(56) $C_{6-14}$ arylsulfonylamino groups that may be substituted with a $C_{1-6}$ alkyl group (such as, e.g., a phenylsulfonylamino group and a toluenesulfonylamino group);

(57) $C_{1-6}$ alkyl groups optionally substituted with at least one halogen;

(58) $C_{2-6}$ alkenyl groups;

(59) $C_{2-6}$ alkynyl groups;

(60) $C_{3-10}$ cycloalkyl groups;

(61) $C_{3-10}$ cycloalkenyl groups; and

(62) $C_{6-14}$ aryl groups.

A non-limiting example of the number of the substituents in the "hydrocarbon groups that may be substituted" (i.e., "optionally substituted hydrocarbon groups") is one to five, such as, e.g., one to three. When the number of substituents is two or more, each substituent may be the same or may be different.

In the present Specification, non-limiting examples of "heterocyclic groups" (including the "heterocyclic groups" in the "heterocyclic groups that may be substituted" or "optionally substituted heterocyclic groups") include (i) aromatic heterocyclic groups, (ii) non-aromatic heterocyclic groups, and (iii) 7- to 10-membered bridged heterocyclic groups, each containing at least one carbon and 1 to 4 heteroatoms chosen from nitrogen, sulfur, and oxygen as ring-constituent atoms.

In the present Specification, non-limiting examples of "aromatic heterocyclic groups" (including, e.g., "5- to 14-membered aromatic heterocyclic groups") include 5- to 14-membered (such as, e.g., 5- to 10-membered) aromatic heterocyclic groups containing at least one carbon and 1 to 4 heteroatoms chosen from nitrogen, sulfur, and oxygen as ring-constituent atoms.

Non-limiting examples of "aromatic heterocyclic groups" include 5- to 6-membered monocyclic aromatic heterocyclic groups such as a thienyl group, a furyl group, a pyrrolyl group, an imidazolyl group, a pyrazolyl group, a thiazolyl group, an isothiazolyl group, an oxazolyl group, an isoxazolyl group, a pyridyl group, a pyrazinyl group, a pyrimidinyl group, a pyridadinyl group, a 1,2,4-oxadiazolyl group, a 1,3,4-oxadiazolyl group, a 1,2,4-thiadiazolyl group, a 1,3,4-thiadiazolyl, a triazolyl group, a tetrazolyl group, and a triazinyl group; and 8- to 14-membered condensed polycyclic (such as, e.g., bi- or tricyclic) aromatic heterocyclic groups such as a benzothiophenyl group, a benzofuranyl group, a benzimidazolyl group, a benzoxazolyl group, a benzisoxazolyl group, a benzothiazolyl group, a benzoisothiazolyl group, a benzotriazolyl group, an imidazopyridinyl group, a thienopyridinyl group, a furopyridinyl group, a pyrrolopyridinyl group, a pyrazolopyridinyl group, an oxazolopyridinyl group, a thiazolopyridinyl group, an imidazopyradinyl group, an imidazopyrimidinyl group, a thienopyrimidinyl group, a furopyrimidinyl group, a pyrrolopyrimidinyl group, a pyrazolopyrimidinyl group, an oxazolopyrimidinyl group, a thiazolopyrimidinyl group, a pyrazolotriadinyl group, a naft[2,3-b]thienyl group, a phenoxathiinyl group, an indolyl group, an isoindolyl group, a 1H-indazolyl group, a purinyl group, an isoquinolyl group, a quinolyl group, a phthalazinyl group, a naphthyridinyl group, a quinoxalinyl group, a quinazolinyl group, a cinnolinyl group, a carbazolyl group, a β-carbolinyl group, a phenanthridinyl group, an acridinyl group, a phenazinyl group, a phenothiazinyl group, and a phenoxadinyl group.

In the present Specification, non-limiting examples of "non-aromatic heterocyclic groups" (including, e.g., 3- to 14-membered non-aromatic heterocyclic groups) include 3- to 14-membered (such as, e.g., 4- to 10-membered) non-aromatic heterocyclic groups containing at least one carbon and 1 to 4 heteroatoms chosen from nitrogen, sulfur, and oxygen as ring-constituent atoms.

Non-limiting examples of "non-aromatic heterocyclic groups" include 3- to 8-membered monocyclic non-aromatic heterocyclic groups such as an aziridinyl group, an oxylanyl group, a thiiranyl group, an azetidinyl group, an oxetanyl group, a thietanyl group, a tetrahydrothienyl group, a tetrahydrofuranyl group, a pyrrolinyl group, a pyrrolidinyl group, an imidazolinyl group, an imidazolidinyl group, an oxazolinyl group, an oxazolydinyl group, a pyrazolinyl group, a pyrazolydinyl group, a thiazolinyl group, a thiazolidinyl group, a tetrahydroisothiazolyl group, a tetrahydrooxazolyl group, a tetrahydroisooxazolyl group, a piperidinyl group, a piperazinyl group, a tetrahydropyridinyl group, a dihydropyridinyl group, a dihydrothiopyranyl group, a tetrahydropyrimidinyl group, a tetrahydropyridazinyl group, a dihydropyranyl group, a tetrahydropyranyl group, a tetrahydrothiopyranyl group, a morpholinyl group, a thiomorpholinyl group, an azepanyl group, a diazepanyl group, an azepinyl group, an oxepanyl group, an azocanyl group, and a diazocanyl group; and 9- to 14-membered condensed polycyclic (such as bi- or tricyclic) non-aromatic heterocyclic groups such as a dihydrobenzofuranyl group, a dihydrobenzoimidazolyl group, a dihydrobenzoxazolyl group, a dihydrobenzothiazolyl group, a dihydrobenzoisothiazolyl group, a dihydronaphtho [2,3-b] thienyl group, a tetrahydroisoquinolyl group, a tetrahydroquinolyl group, a 4H-quinolidinyl group, an indolinyl group, an isoindolinyl group, a tetrahydrothieno[2,3-c]pyridinyl group, a tetrahydrobenzoazepinyl group, a tetrahydroquinoxalinyl group, a tetrahydrophenanthridinyl group, a hexahydrophenothiazinyl group, a hexahydrophenoxadinyl group, a tetrahydrophthalazinyl group, a tetrahydronaphthiridinyl group, a tetrahydroquinazolinyl group, a tetrahydrocinnolinyl group, a tetrahydrocarbazolyl group, a tetrahydro-3-carbolinyl group, a tetrahydroacridinyl group, a tetrahydrophenazinyl group, a tetrahydrothioxanthenyl group, and an octahydroisoquinolyl group.

In the present Specification, non-limiting examples of "7- to 10-membered bridged heterocyclic groups" include a quinuclidinyl group and a 7-azabicyclo[2.2.1] heptanyl group.

In the present Specification, non-limiting examples of "nitrogen-containing heterocyclic groups" include heterocyclic groups containing at least one nitrogen as a ring-constituent atom.

In the present Specification, examples of "heterocyclic groups that may be substituted" (i.e., "optionally substituted heterocyclic groups") include, but are not limited to, heterocyclic groups that may be substituted with one or more substituents chosen from substituent group A, described above.

A non-limiting example of the number of substituents in "heterocyclic groups which may be substituted" (i.e., "optionally substituted heterocyclic groups") is one to three. When the number of substituents is two or more, each substituent may be the same or may be different.

In the present Specification, non-limiting examples of "acyl groups" include a formyl group, a carboxy group, a carbamoyl group, a thiocarbamoyl group, a sulfino group, a sulfo group, a sulfamoyl group, and a phosphono group, each of which may be substituted with "one or two substituents chosen from $C_{1-6}$ alkyl groups, $C_{2-6}$ alkenyl groups, $C_{3-10}$ cycloalkyl groups, $C_{3-10}$ cycloalkenyl groups, $C_{6-14}$ aryl groups, $C_{7-16}$ aralkyl groups, 5- to 14-membered aromatic heterocyclic groups, and 3- to 14-membered non-aromatic heterocyclic groups, each of which may be substituted with one to three substituents chosen from halogens, $C_{1-6}$ alkoxy groups, a hydroxy group, a nitro group, a cyano group, an amino group, and a carbamoyl group that each may be halogenated."

In addition, non-limiting examples of "acyl groups" include a hydrocarbon-sulfonyl group, a heterocyclic-sulfonyl group, a hydrocarbon-sulfinyl group, and a heterocyclic-sulfinyl group.

As used herein, a hydrocarbon-sulfonyl group refers to a sulfonyl group to which a hydrocarbon group is bound, a heterocyclic-sulfonyl group refers to a sulfonyl group to which a heterocyclic group is bound, a hydrocarbon-sulfinyl group refers to a sulfinyl group to which a hydrocarbon group is bound, and a heterocyclic-sulfinyl group refers to a sulfinyl group to which a heterocyclic group is bound.

Non-limiting examples of "acyl groups" include a formyl group, a carboxy group, $C_{1-6}$ alkyl-carbonyl groups, $C_{2-6}$ alkenyl-carbonyl groups (such as, e.g., a crotonoyl group), $C_{3-10}$ cycloalkyl-carbonyl groups (such as, e.g., a cyclobutanecarbonyl group, a cyclopentanecarbonyl group, a cyclohexanecarbonyl group, or a cycloheptanecarbonyl group), $C_{3-10}$ cycloalkenyl-carbonyl groups (such as, e.g., a 2-cyclohexenecarbonyl group), $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, $C_{6-14}$ aryloxy-carbonyl groups (such as, e.g., a phenyloxycarbonyl group or a naphthyloxycarbonyl group), $C_{7-16}$ aralkyloxy-carbonyl groups (such as, e.g., a benzyloxycarbonyl group or a phenethyloxycarbonyl group), a carbamoyl group, mono- or di-$C_{1-6}$ alkyl-carbamoyl groups, mono- or di-$C_{2-6}$ alkenyl-carbamoyl groups (such as, e.g., a diallyl carbamoyl group), mono- or di-$C_{3-10}$ cycloalkyl-carbamoyl groups (such as, e.g., a cyclopropylcarbamoyl group), mono- or di-$C_{6-14}$ aryl-carbamoyl groups (such as, e.g., a phenylcarbamoyl group), mono- or di-$C_{7-16}$ aralkyl-carbamoyl groups, 5- to 14-membered aromatic heterocyclic carbamoyl groups (such as, e.g., a pyridylcarbamoyl group), a thiocarbamoyl group, mono- or di-$C_{1-6}$ alkyl-thiocarbamoyl groups (such as, e.g., a methylthiocarbamoyl group or an N-ethyl-N-methylthiocarbamoyl group), mono- or di-$C_{2-6}$ alkenyl-thiocarbamoyl groups (such as, e.g., a diallylthiocarbamoyl group), mono- or di-$C_{3-10}$ cycloalkyl-thiocarbamoyl groups (such as, e.g., a cyclopropylthiocarbamoyl group or a cyclohexylthiocarbamoyl group), mono- or di-$C_{6-14}$ aryl-thiocarbamoyl groups (such as, e.g., a phenyl-thiocarbamoyl group), mono- or di-$C_{7-16}$ aralkyl-thiocarbamoyl groups (such as, e.g., a benzylthiocarbamoyl group or a phenethylthiocarbamoyl group), 5- to 14-membered aromatic heterocyclic thiocarbamoyl groups (such as, e.g., a pyridylthiocarbamoyl group), a sulfino group, $C_{1-6}$ alkylsulfinyl groups (such as, e.g., a methylsulfinyl group or an ethylsulfinyl group), a sulfo group, $C_{1-6}$ alkylsulfonyl groups, $C_{6-14}$ arylsulfonyl groups, a phosphono group, and mono- or di-$C_{1-6}$ alkylphosphono groups (such as, e.g., a dimethylphosphono group, a diethylphosphono group, a diisopropylphosphono group, or a dibutylphosphono group).

In the present Specification, examples of "amino groups that may be substituted" (i.e., "optionally substituted amino groups") include, but are not limited to, amino groups that may be substituted with "one or two substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, a carbamoyl group, mono- or di-$C_{1-6}$ alkyl-carbamoyl groups, mono- or di-$C_{7-16}$ aralkyl-carbamoyl groups, $C_{1-6}$ alkylsulfonyl groups, and $C_{6-14}$ arylsulfonyl groups that each may be substituted with one to three substituents chosen from substituent group A."

Non-limiting examples of "amino groups that may be substituted" (i.e., "optionally substituted amino groups") include an amino group, mono- or di-($C_{1-6}$ alkyl) amino groups, wherein $C_{1-6}$ alkyl may be optionally substituted with at least one halogen (such as, e.g., a methylamino group, a trifluoromethylamino group, a dimethylamino group, an ethylamino group, a diethylamino group, a propylamino group, or a dibutylamino group), mono- or di-$C_{2-6}$ alkenyl amino groups (such as, e.g., a diallylamino group), mono- or di-$C_{3-10}$ cycloalkylamino groups (such as, e.g., a cyclopropylamino group or a cyclohexylamino group), mono- or di-$C_{6-14}$ arylamino groups (such as, e.g., a phenylamino group), mono- or di-$C_{7-16}$ aralkylamino groups (such as, e.g., a benzylamino group or a dibenzylamino group), mono- or di-($C_{1-6}$ alkyl)-carbonylamino group, wherein $C_{1-6}$ alkyl may be optionally substituted with at least one halogen (such as, e.g., an acetylamino group or a propionylamino group), mono- or di-$C_{6-14}$ aryl-carbonylamino groups (such as, e.g., a benzoylamino group), mono- or di-$C_{7-16}$ aralkyl-carbonylamino groups (such as, e.g., a benzylcarbonylamino group), mono- or di-5- to 14-membered aromatic heterocyclic carbonylamino groups (such as, e.g., a nicotinoylamino group and an isonicotinoylamino group), mono- or di-3- to 14-membered non-aromatic heterocyclic carbonylamino groups (such as, e.g., a piperidinylcarbonylamino group), mono- or di-$C_{1-6}$ alkoxycarbonylamino groups (such as, e.g., a tert-butoxycarbonylamino group), 5- to 14-membered aromatic heterocyclic amino groups (such as, e.g., a pyridylamino group), a carbamoylamino group, (mono- or di-$C_{1-6}$ alkyl-carbamoyl) amino groups (such as, e.g., a methylcarbamoylamino group), (mono- or di-$C_{7-16}$ aralkyl-carbamoyl) amino groups (such as, e.g., a benzylcarbamoyl amino), $C_{1-6}$ alkylsulfonylamino groups (such as, e.g., a methylsulfonylamino group or an ethylsulfonylamino group), $C_{6-14}$ arylsulfonylamino groups (such as, e.g., a phenylsulfonylamino group), ($C_{1-6}$ alkyl) ($C_{1-6}$ alkyl-carbonyl) amino groups (such as, e.g., an N-acetyl-N-methylamino group), and ($C_{1-6}$ alkyl) ($C_{6-14}$ aryl-carbonyl) amino groups (such as, e.g., an N-benzoyl-N-methylamino group).

In the present Specification, examples of "carbamoyl groups that may be substituted" (i.e., "optionally substituted carbamoyl groups") include, but are not limited to, carbamoyl groups that may be substituted with "one or two substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, a carbamoyl group, mono- or di-$C_{1-6}$ alkyl-carbamoyl groups, and mono- or di-$C_{7-16}$ aralkyl-carbamoyl groups, each of which may be substituted with one to three substituents chosen from substituent group A."

Non-limiting examples of carbamoyl groups that may be substituted (i.e., optionally substituted carbamoyl groups) include a carbamoyl group, mono- or di-$C_{1-6}$ alkyl-carbamoyl groups, mono- or di-$C_{2-6}$ alkenyl-carbamoyl groups (such as, e.g., a diallylcarbamoyl group), mono- or di-$C_{3-10}$ cycloalkyl-carbamoyl groups (such as, e.g., a cyclopropylcarbamoyl group or a cyclohexylcarbamoyl group), mono- or di-$C_{6-14}$ aryl-carbamoyl groups (such as, e.g., a phenylcarbamoyl group), mono- or di-$C_{7-16}$ aralkyl-carbamoyl groups, mono- or di-$C_{1-6}$ alkyl-carbonyl-carbamoyl groups (such as, e.g., an acetylcarbamoyl group or a propionylcarbamoyl group), mono- or di-$C_{6-14}$ aryl-carbonyl-carbamoyl groups (such as, e.g., a benzoylcarbamoyl group), and 5- to 14-membered aromatic heterocyclic carbamoyl groups (such as, e.g., a pyridylcarbamoyl group).

In the present Specification, examples of "thiocarbamoyl groups that may be substituted" (i.e., "optionally substituted thiocarbamoyl groups") include, but are not limited to, a thiocarbamoyl group that may be substituted with "one or two substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, a carbamoyl group, mono- or di-$C_{1-6}$ alkyl-carbamoyl groups, and mono- or di-$C_{7-16}$ aralkyl-carbamoyl groups, each of which may be substituted with one to three substituents chosen from substituent group A."

Non-limiting examples of thiocarbamoyl groups that may be substituted (i.e., optionally substituted thiocarbamoyl groups) include a thiocarbamoyl group, mono- or di-$C_{1-6}$ alkyl-thiocarbamoyl groups (such as, e.g., a methylthiocarbamoyl group, an ethylthiocarbamoyl group, a dimethylthiocarbamoyl group, a diethylthiocarbamoyl group, or an N-ethyl-N-methylthiocarbamoyl group), mono- or di-$C_{2-6}$ alkenyl-thiocarbamoyl groups (such as, e.g., a diallylthiocarbamoyl group), mono- or di-$C_{3-10}$ cycloalkyl-thiocarbamoyl groups (such as, e.g., a cyclopropylthiocarbamoyl group or a cyclohexyl thiocarbamoyl group), mono- or di-$C_{6-14}$ aryl-thiocarbamoyl groups (such as, e.g., a phenylthiocarbamoyl group), mono- or di-$C_{7-16}$ aralkyl-thiocarbamoyl groups (such as, e.g., a benzylthiocarbamoyl group or a phenethyl thiocarbamoyl group), mono- or di-$C_{1-6}$ alkyl-carbonyl-thiocarbamoyl groups (such as, e.g., an acetylthiocarbamoyl group or a propionyl thiocarbamoyl group), mono- or di-$C_{6-14}$ aryl-carbonyl-thiocarbamoyl groups (such as, e.g., a benzoylthiocarbamoyl group), and 5- to 14-membered aromatic heterocyclic thiocarbamoyl groups (such as, e.g., a pyridylthiocarbamoyl group).

In the present Specification, examples of the "sulfamoyl group that may be substituted" (i.e., "optionally substituted sulfamoyl groups") include, but are not limited to, sulfamoyl groups that may be substituted with "one or two substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, a carbamoyl group, mono- or di-$C_{1-6}$ alkyl-carbamoyl groups, and mono- or di-$C_{7-16}$ aralkyl-carbamoyl groups, each of which may be substituted with one to three substituents chosen from substituent group A."

Non-limiting examples of sulfamoyl groups that may be substituted (i.e., optionally substituted sulfamoyl groups) include a sulfamoyl group, mono- or di-$C_{1-6}$ alkyl-sulfamoyl groups (such as, e.g., a methylsulfamoyl group, an ethylsulfamoyl group, a dimethylsulfamoyl group, a diethylsulfamoyl group, or an N-ethyl-N-methylsulfamoyl group), mono- or di-$C_{2-6}$ alkenyl-sulfamoyl groups (such as, e.g., a diallylsulfamoyl group), mono- or di-$C_{3-10}$ cycloalkyl-sulfamoyl groups (such as, e.g., a cyclopropylsulfamoyl group or a cyclohexylsulfamoyl group), mono- or di-$C_{6-14}$ arylsulfamoyl groups (such as, e.g., a phenylsulfamoyl group), mono- or di-$C_{7-16}$ aralkyl-sulfamoyl groups (such as, e.g., a benzylsulfamoyl group or a phenethylsulfamoyl group), mono- or di-$C_{1-6}$ alkyl-carbonyl-sulfamoyl groups (such as, e.g., an acetylsulfamoyl group or a propionylsulfamoyl group), mono- or di-$C_{6-14}$ aryl-carbonyl-sulfamoyl groups (such as, e.g., a benzoylsulfamoyl group), and 5- to 14-membered aromatic heterocyclicsulfamoyl groups (such as, e.g., a pyridylsulfamoyl group).

In the present Specification, examples of "hydroxy groups that may be substituted" (i.e., "optionally substituted hydroxy groups") include, but are not limited to, a hydroxy group that may be substituted with a "substituent chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, a carbamoyl group, mono- or di-$C_{1-6}$ alkyl-carbamoyl groups, mono- or di-$C_{7-16}$ aralkyl-carbamoyl groups, $C_{1-6}$ alkylsulfonyl groups, and $C_{6-14}$ arylsulfonyl groups, each of which may be substituted by one to three substituents chosen from substituent group A."

Non-limiting examples of hydroxy groups that may be substituted (i.e., optionally substituted hydroxy groups) include a hydroxy group, $C_{1-6}$ alkoxy groups, $C_{2-6}$ alkenyloxy groups (such as, e.g., an allyloxy group, a 2-butenyloxy group, a 2-pentenyloxy group, and a 3-hexenyloxy group), $C_{3-10}$ cycloalkyloxy groups (such as, e.g., a cyclohexyloxy group), $C_{6-14}$ aryloxy groups (such as, e.g., a phenoxy group or a naphthyloxy group), $C_{7-16}$ aralkyloxy groups (such as, e.g., a benzyloxy group or a phenethyloxy group), $C_{1-6}$ alkyl-carbonyloxy groups (such as, e.g., an acetyloxy group, a propionyloxy group, a butyryloxy group, an isobutyryloxy, or a pivaloyloxy group), $C_{6-14}$ aryl-carbonyloxy groups (such as, e.g., a benzoyloxy group), $C_{7-16}$ aralkyl-carbonyloxy groups (such as, e.g., a benzylcarbonyloxy group), 5- to 14-membered aromatic heterocyclic carbonyloxy groups (such as, e.g., a nicotinoyloxy group), 3- to 14-membered non-aromatic heterocyclic carbonyloxy groups (such as, e.g., a piperidinylcarbonyloxy group), $C_{1-6}$ alkoxy-carbonyloxy groups (such as, e.g., a tert-butoxycarbonyloxy group), 5- to 14-membered aromatic heterocyclic oxy groups (such as, e.g., a pyridyloxy group), a carbamoyloxy group, $C_{1-6}$ alkyl-carbamoyloxy groups (such as, e.g., a methylcarbamoyloxy group), $C_{7-16}$ aralkyl-carbamoyloxy groups (such as, e.g., a benzylcarbamoyloxy group), $C_{1-6}$ alkylsulfonyloxy groups (such as, e.g., a methylsulfonyloxy group or an ethylsulfonyloxy group), and $C_{6-14}$ arylsulfonyloxy groups (such as, e.g., a phenylsulfonyloxy group).

In the present Specification, examples of "sulfanyl groups that may be substituted" (i.e., "optionally substituted sulfanyl groups") include, but are not limited to, sulfanyl groups that may be substituted with at least one "substituent chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, and 5- to 14-membered aromatic heterocyclic carbonyl groups, each of which may be substituted with one to three substituents chosen from substituent group A."

Non-limiting examples of sulfanyl groups that may be substituted (i.e., optionally substituted sulfanyl groups) include a sulfanyl (—SH) group, $C_{1-6}$ alkylthio groups, $C_{2-6}$ alkenylthio groups (such as, e.g., an allylthio group, a 2-butenylthio group, a 2-pentenylthio group, or a 3-hexenylthio group), $C_{3-10}$ cycloalkylthio groups (such as, e.g., a cyclohexylthio group), $C_{6-14}$ arylthio groups (such as, e.g., a phenylthio group or a naphthylthio group), $C_{7-16}$ aralkylthio groups (such as, e.g., a benzylthio group or a phenethylthio group), $C_{1-6}$ alkyl-carbonylthio groups (such as, e.g., an acetylthio group, a propionylthio group, a butyrylthio group, an isobutyrylthio group, or a pivaloylthio group), $C_{6-14}$ aryl-carbonylthio groups (such as, e.g., a benzoylthio group), 5- to 14-membered aromatic heterocyclic thio groups (such as, e.g., a pyridylthio group), and halogenated thio groups (such as, e.g., a pentafluorothio group).

In the present Specification, examples of "silyl groups that may be substituted" (i.e., "optionally substituted silyl groups") include, but are not limited to, silyl groups that may be substituted with "one to three substituents chosen from $C_{1-6}$ alkyl groups, $C_{2-6}$ alkenyl groups, $C_{3-10}$ cycloalkyl groups, $C_{6-14}$ aryl groups, and $C_{7-16}$ aralkyl groups, each of which may be optionally substituted with one to three substituents chosen from substituent group A."

Non-limiting examples of silyl groups that may be substituted (i.e., optionally substituted silyl groups) include tri-$C_{1-6}$ alkylsilyl groups (such as, e.g., a trimethylsilyl group and a tert-butyl (dimethyl) silyl group).

In the present Specification, non-limiting examples of "$C_{1-3}$ alkyl groups" include $C_{1-3}$ alkyl groups with one to three carbons.

In the present Specification, "$C_{1-3}$ alkyl groups that may be substituted with fluorine atom(s)" (i.e., "$C_{1-3}$ alkyl groups optionally substituted with at least one fluorine") means $C_{1-3}$ alkyl groups that may be substituted, e.g., with one to five (such as, e.g., one to three, one or two) fluorine.

In the present Specification, benzene groups in "benzene groups that may be further substituted" (i.e., "optionally substituted benzene groups") may have, e.g., one to four (such as, e.g., one to three, one or two) substituents chosen from the above-mentioned substituent group A.

In the present Specification, among the "benzene groups, pyridine groups, or pyrazine groups that each may be further substituted" (i.e., "optionally substituted benzene groups, optionally substituted pyridine groups, and optionally substituted pyrazine groups"), benzene groups may be substituted with a substituent similar to the above-mentioned "benzene groups that may be further substituted," pyridine groups may be substituted with, e.g., one to three (such as, e.g., one or two) substituents chosen from the above-mentioned substituent group A, and pyrazine groups may be substituted, e.g., one or two (such as, e.g., one) substituents chosen from the above-mentioned substituent group A.

In the present Specification, pyrimidine groups of "pyrimidine groups that may be further substituted" (i.e., "optionally substituted pyrimidine groups") may be substituted with, e.g., one or two (such as, e.g., one) substituents chosen from the above-mentioned substituent group A.

The definition of each symbol in formula (I) is described in detail below.

In some embodiments, $R^1$ is chosen from halogens and $C_{1-3}$ alkyl groups optionally substituted with at least one fluorine.

In some embodiments, $R^1$ is chosen from halogens (such as, e.g., fluorine or chlorine) and $C_{1-3}$ alkyl groups (such as, e.g., a methyl group) optionally substituted with one to three (such as, e.g., one or two) fluorine.

In some embodiments, $R^2$ is chosen from $C_{1-3}$ alkyl groups optionally substituted with at least one fluorine.

In some embodiments, $R^2$ is chosen from $C_{1-3}$ alkyl groups (such as, e.g., a methyl group or an ethyl group) optionally substituted with one to three fluorine. In some embodiments, $R^2$ is chosen from unsubstituted $C_{1-3}$ alkyl groups (such as, e.g., a methyl group).

In some embodiments, $R^3$ is chosen from hydrogen and hydroxy groups.

In some embodiments, ring A is chosen from optionally substituted benzene groups.

In some embodiments, the benzene group in ring A may be substituted with one to four (such as, e.g., one or two) substituents in addition to $R^1$ and —O-ring B—. Non-limiting examples of the substituent include at least one substituent chosen from the above-mentioned substituent group A, such as, e.g., halogens (such as, e.g., a fluorine).

In some embodiments, ring A is chosen from benzene groups optionally substituted with one to four (such as, e.g., one or two) halogens (such as, e.g., a fluorine). In some embodiments, ring A is chosen from benzene groups optionally substituted with one or two (such as, e.g., one) halogens (such as, e.g., a fluorine).

In some embodiments of the present disclosure, ring A is chosen from benzene groups substituted with at least one halogen (such as, e.g., a fluorine) at one or two ortho positions relative to the —O-ring B—.

In some embodiments, ring A is chosen from groups of the formula:

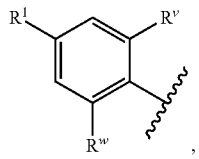

wherein:
R$^1$ is as defined above;
R$^v$ is chosen from halogens (such as, e.g., fluorine); and
R$^w$ is chosen from hydrogen and halogens (such as, e.g., fluorine).

In some embodiments, ring B is chosen from groups of the following formulas:

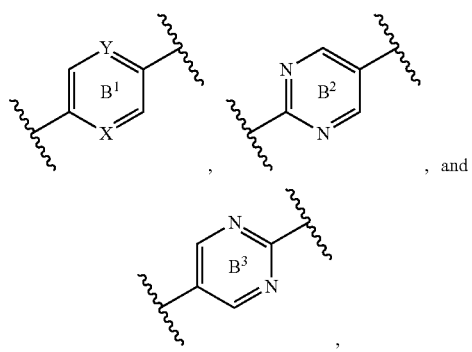

In some embodiments, X and Y are each independently chosen from carbon and nitrogen.

In some embodiments, ring B$^1$ is chosen from optionally substituted benzene groups, optionally substituted pyridine groups, and optionally substituted pyrazine groups.

In some embodiments, ring B$^2$ is chosen from optionally substituted pyrimidine groups.

In some embodiments, ring B$^3$ is chosen from optionally substituted pyrimidine groups.

In some embodiments, ring B$^1$ is chosen from optionally substituted benzene groups, optionally substituted pyridine groups, and optionally substituted pyrazine groups.

In some embodiments, optionally substituted benzene groups (X and Y are both carbon), optionally substituted pyridine groups (one of X and Y is carbon and the other is nitrogen), or optionally substituted pyrazine groups (X and Y are both nitrogen) indicated by ring B$^1$ may be substituted with one to four (such as, e.g., one or two) substituents. Non-limiting examples of substituents include substituents chosen from the above-mentioned substituent group A.

In some embodiments, ring B$^1$ is chosen from an unsubstituted benzene group, unsubstituted pyridine groups, and an unsubstituted pyrazine group.

In some embodiments, ring B$^1$ is chosen from unsubstituted pyridine groups, wherein one of X and Y is carbon and the other is nitrogen, such as, e.g., X is nitrogen and Y is carbon.

In some embodiments, ring B$^2$ is optionally substituted with one or two (such as, e.g., one) substituents. Non-limiting examples of substituents include substituents chosen from the above-mentioned substituent group A.

In some embodiments, ring B$^3$ is optionally substituted with one or two (such as, e.g., one) substituents. Non-limiting examples of substituents include substituents chosen from the above-mentioned substituent group A.

In some embodiments, ring B$^2$ is an unsubstituted pyrimidine group.

In some embodiments, ring B$^3$ is an unsubstituted pyrimidine group.

In some embodiments, ring B is chosen from groups of the following formulas:

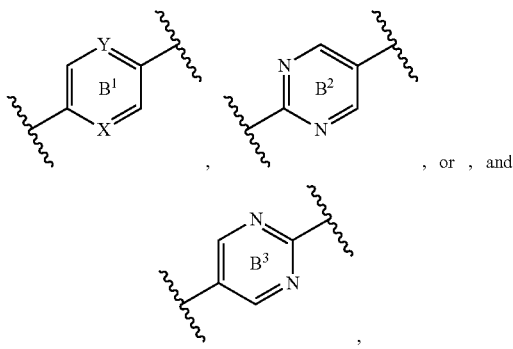

wherein:
X and Y are each independently chosen from carbon and nitrogen;
ring B$^1$ is chosen from an unsubstituted benzene group, unsubstituted pyridine groups, and an unsubstituted pyrazine group;
ring B$^2$ is an unsubstituted pyrimidine group; and
ring B$^3$ is an unsubstituted pyrimidine group.

In some embodiments, ring B is chosen from groups of the following formulas:

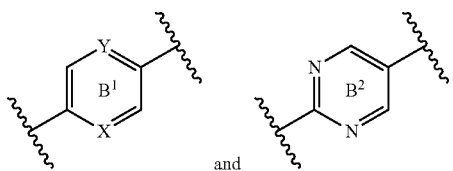

wherein:
one of X and Y is carbon and the other is nitrogen;
ring B$^1$ is chosen from unsubstituted pyridine groups; and
ring B$^2$ is an unsubstituted pyrimidine group.

In some embodiments, ring B is chosen from groups of the formula:

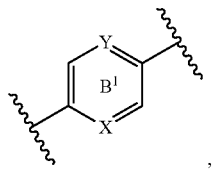

wherein:
one of X and Y is carbon and the other is nitrogen (such as, e.g., X is nitrogen and Y is carbon); and
ring B¹ is unsubstituted.

In some embodiments, Z is chosen from $CH_2$, $CF_2$, O, and NH.

In some embodiments of the present disclosure, Z is chosen from $CH_2$, O, and NH.

In some embodiments, Z is $CH_2$ or O.

Non-limiting examples of compounds of formula (I) and salts thereof include the following compounds and salts thereof.

[Compound I-1]

A compound of formula (I), or a salt thereof, wherein:
$R^1$ is chosen from halogens (such as, e.g., fluorine and chlorine) and $C_{1-3}$ alkyl groups (such as, e.g., a methyl group) optionally substituted with one to three fluorine;
$R^2$ is chosen from $C_{1-3}$ alkyl groups (such as, e.g., a methyl group and an ethyl group) optionally substituted with one to three fluorine;
$R^3$ is chosen from hydrogen and hydroxyl groups;
ring A is chosen from benzene groups optionally substituted with one to four (such as, e.g., one or two) halogens (such as, e.g., fluorine);
ring B is chosen from groups of the following formulas:

wherein:
X and Y are each independently chosen from carbon and nitrogen;
ring B¹ is chosen from an unsubstituted benzene group, unsubstituted pyridine groups, and an unsubstituted pyrazine group;
ring B² is an unsubstituted pyrimidine group; and
ring B³ is an unsubstituted pyrimidine group; and
Z is chosen from $CH_2$, $CF_2$, O, and NH.

[Compound I-2]

A compound of formula (I), or a salt thereof, wherein:
$R^1$ is chosen from halogens (such as, e.g., fluorine and chlorine) and $C_{1-3}$ alkyl groups (such as, e.g., a methyl group) optionally substituted with one or two fluorine;
$R^2$ is chosen from unsubstituted $C_{1-3}$ alkyl groups (such as, e.g., a methyl group);
$R^3$ is chosen from hydrogen and hydroxyl groups;
ring A is chosen from benzene groups optionally substituted with one or two (such as, e.g., one) halogens (such as, e.g., fluorine);

ring B is chosen from groups of the following formulas:

wherein:
one of X and Y is carbon and the other is nitrogen (such as, e.g., X is nitrogen and Y is carbon);
ring B¹ is chosen from unsubstituted pyridine groups; and
ring B² is an unsubstituted pyrimidine group; and
Z is $CH_2$ or O.

[Compound I-3]

A compound of formula (I), or a salt thereof, wherein:
$R^1$ is chosen from halogens (such as, e.g., fluorine and chlorine) and $C_{1-3}$ alkyl groups (such as, e.g., a methyl group) optionally substituted with one or two fluorine;
$R^2$ is chosen from unsubstituted $C_{1-3}$ alkyl groups (such as, e.g., a methyl group);
$R^3$ is chosen from hydrogen and hydroxyl groups;
ring A is chosen from groups of the formula:

wherein:
$R^v$ is chosen from halogens (such as, e.g., fluorine); and
$R^w$ is chosen from hydrogen and halogens (such as, e.g., fluorine);
ring B is chosen from groups of the following formulas:

wherein:
one of X and Y is carbon and the other is nitrogen (such as, e.g., X is nitrogen and Y is carbon);
ring B¹ is chosen from unsubstituted pyridine groups; and
ring B² is an unsubstituted pyrimidine group; and
Z is $CH_2$ or O.

Non-limiting examples of compounds of formula (I) include compounds of the following Examples 1 to 50.

In some embodiments, the salt of a compound of formula (I) is a pharmacologically acceptable salt. Non-limiting examples of such salts include salts with an inorganic base, salts with an organic base, salts with an inorganic acid, salts with an organic acid, and salts with a basic or acidic amino acid.

Non-limiting examples of salts with an inorganic base include: alkaline metal salts, such as, e.g., sodium salts and potassium salts; alkaline earth metal salts, such as, e.g., calcium salts and magnesium salts; aluminum salts; and ammonium salts.

Non-limiting examples of salts with an organic base include salts with trimethylamine, triethylamine, pyridine, picoline, ethanolamine, diethanolamine, triethanolamine, trometamine [tris (hydroxymethyl) methylamine], tert-butylamine, cyclohexylamine, benzylamine, dicyclohexylamine, or N,N-dibenzylethylenediamine.

Non-limiting examples of salts with an inorganic acid include salts with hydrogen chloride, hydrogen bromide, nitric acid, sulfuric acid, or phosphoric acid.

Non-limiting examples of salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, or p-toluenesulfonic acid.

Non-limiting examples of salts with a basic amino acid include salts with arginine, lysine, or ornithine.

Non-limiting examples of salts with an acidic amino acid include salts with aspartic acid or glutamic acid.

In some embodiments, a compound of formula (I) may be administered as a prodrug.

In some embodiments, a prodrug of a compound of formula (I) is a compound which is converted into a compound of formula (I) by reaction with an enzyme, a gastric acid, etc., under physiological conditions in vivo, that is, a compound which is converted into a compound of formula (I) by enzymatic oxidation, reduction, hydrolysis, and the like, and a compound which is converted into a compound of formula (I) by hydrolysis and the like by the gastric acid, etc.

Non-limiting examples of prodrugs of a compound of formula (I) include: compounds in which the amino group of the compound of formula (I) is acylated, alkylated, or phosphorylated (such as, e.g., a compound in which the amino group of the compound of formula (I) is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated, or tert-butylated); compounds in which the hydroxy group of the compound of formula (I) is acylated, alkylated, phosphorylated, or borated (such as, e.g., a compound in which the hydroxy group of the compound of formula (I) is acetylated, palmitoylated, propanoylated, pivaloylated, succinylated, fumarylated, allanylated, or dimethylaminomethylcarbonylated); compounds in which the carboxy group of the compound of formula (I) is esterified or amidated (such as, e.g., a compound in which the carboxy group of the compound of formula (I) is ethyl esterified, phenyl esterified, carboxymethyl esterified, dimethylaminomethyl esterified, pivaloyloxy methyl esterified, ethoxycarbonyloxyethyl esterified, phthalidyl esterified, (5-methyl-2-oxo-1,3-dioxolen-4-yl) methyl esterified, cyclohexyloxycarbonylethyl esterified, or methylamidated); and the like. These prodrugs may be produced from compounds of formula (I) by methods known to those of ordinary skill in the art.

In some embodiments, a prodrug of a compound of formula (I) may be converted to the compound of formula (I) under physiological conditions as described in "IYAKUHIN no KAIHATSU (Development of Pharmaceuticals)", Vol. 7, Design of Molecules, p. 163-198, Published by HIROKAWA SHOTEN (1990).

In some embodiments, a prodrug may form a salt, and examples of such salts include those exemplified as salts of a compound of formula (I) above.

In some embodiments, a compound of formula (I) may be labeled by an isotope (such as, e.g., $^3H$, $^{13}C$, $^{14}C$, $^{18}F$, $^{35}S$, and $^{125}I$) and the like.

In some embodiments, a compound of formula (I) labeled by or substituted with an isotope may be used, for example, as a tracer in the Positron Emission Tomography (PET) (PET tracer), and may be useful in fields such as medical diagnosis.

In some embodiments, a compound of formula (I) may be a hydrate, a non-hydrate, a non-solvate, or a solvate.

In some embodiments, a compound of formula (I) also includes a deuterium conversion form obtained by converting $^1H$ to $^2H$ (D).

In some embodiments, a compound of formula (I) may be a pharmaceutically acceptable co-crystal or co-crystal salt. In some embodiments, a co-crystal or a co-crystal salt is a crystalline substance composed of two or more types of unique substances which are solids at room temperature, each having different physical properties (such as, e.g., structure, melting point, heat of melting, hygroscopicity, solubility, and stability). The co-crystal or the co-crystal salt may be produced according to a co-crystallization method known to those of ordinary skill in the art.

In some embodiments, a compound of formula (I), a salt thereof, or a prodrug thereof can be used as is or by forming a pharmaceutical composition by mixing with a pharmaceutically acceptable carrier or the like. In some embodiments, a compound of formula (I), a salt thereof, or a prodrug thereof may be used as a prophylactic or therapeutic agent for various diseases described below in mammals (such as, e.g., humans, mice, rats, rabbits, dogs, cats, cows, horses, pigs, and monkeys).

Non-limiting examples of pharmacologically acceptable carriers include various organic or inorganic carrier materials conventionally used as formulation materials. In some embodiments, solid formulations comprise an excipient, a lubricant, a binder, a disintegrant, or the like. In some embodiments, liquid formulations comprise a solvent, a solubilization agent, a suspending agent, an isotonicity agent, a buffer, a soothing agent, or the like. In some embodiments, a formulation additive such as a preservative, an antioxidant, a colorant, or a sweetener can be added as necessary.

Non-limiting examples of excipients include lactose, sucrose, D-mannitol, D-sorbitol, starch, gelatinated starch, dextrin, crystalline cellulose, low-substituted hydroxypropylcellulose, carboxymethylcellulose sodium, gum arabic, pullulan, light anhydrous silicic acid, synthetic aluminum silicate, and magnesium aluminometasilicate.

Non-limiting examples of lubricants includes magnesium stearate, calcium stearate, talc, and colloidal silica.

Non-limiting examples of binders include gelatinated starch, sucrose, gelatin, gum arabic, methylcellulose, carboxymethylcellulose, carboxymethylcellulose sodium, crystalline cellulose, D-mannitol, trehalose, dextrin, pullulan, hydroxypropylcellulose, hydroxypropylmethylcellulose, and polyvinylpyrrolidone.

Non-limiting examples of disintegrating agents include lactose, sucrose, starch, carboxymethylcellulose, carboxymethylcellulose calcium, croscarmellose sodium, carboxymethyl starch sodium, light anhydrous silicic acid, and low-substituted hydroxypropylcellulose.

Non-limiting examples of solvents include water for injection, physiological saline, Ringer's solution, alcohol, propylene glycol, polyethylene glycol, sesame seed oil, corn oil, olive oil, and cotton seed oil.

Non-limiting examples of solubilization agents include polyethylene glycol, propylene glycol, D-mannitol, trehalose, benzyl benzoate, ethanol, tris-aminomethane, cholesterol, triethanolamine, sodium carbonate, sodium citrate, sodium salicylate, and sodium acetate.

Non-limiting examples of suspending agents include a surfactant such as stearyl triethanolamine, sodium lauryl sulfate, laurylaminopropionic acid, lecithin, benzalkonium chloride, benzethonium chloride, and glyceryl monostearate; a hydrophilic polymer such as polyvinyl alcohol, polyvinylpyrrolidone, carboxymethylcellulose sodium, methylcellulose, hydroxymethylcellulose, hydroxyethylcellulose, and hydroxypropylcellulose; polysorbates, and polyoxyethylene hydrogenated castor oil.

Non-limiting examples of isotonic agents include sodium chloride, glycerin, D-mannitol, D-sorbitol, and glucose.

Non-limiting examples of buffer agents include a buffer solution such as a phosphate, an acetate, a carbonate, and a citrate.

Non-limiting examples of soothing agents include benzyl alcohol.

Non-limiting examples of preservatives include paraoxybenzoic acid esters, chlorobutanol, benzyl alcohol, phenethyl alcohol, dehydroacetic acid, and sorbic acid.

Non-limiting examples of antioxidants include sulfite and ascorbate.

Non-limiting examples of colorants include a water-soluble edible tar dye (such as, e.g., a food coloring such as edible red No. 2 and No. 3, edible yellow No. 4 and No. 5, and edible blue No. 1 and No. 2), a water-insoluble lake dye (such as, e.g., an aluminum salt of the above-mentioned water-soluble edible tar dye), a natural dye (such as, e.g., β-carotene, chlorophyll, and Bengala dye).

Non-limiting examples of sweeteners include saccharin sodium, dipotassium glycyrrhizinate, aspartame, and stevia.

Non-limiting examples of pharmaceutical dosage forms of the present disclosure include oral formulations such as tablets (such as, e.g., sugar-coated tablets, film-coated tablets, sublingual tablets, oral disintegrating tablets, buccal tablets, and the like), pills, powders, granules, capsules (such as, e.g., soft capsules and microcapsules), troches, syrups, liquids, emulsions, suspension agents, aerosols, films (such as, e.g., oral disintegrating films and oral mucosal patches); and parenteral formulations such as injections (such as, e.g., subcutaneous injections, intravenous injections, intramuscular injections, intraperitoneal injections, and infusions), topical agents (such as, e.g., transdermal formulations, ointments, lotions, and patches), suppositories (such as, e.g., rectal suppositories and vaginal suppositories), pellets, parenteral agents, transpulmonary agents (such as, e.g., inhalants), and eye drops.

A compound of formula (I), a salt thereof, or a prodrug thereof or a pharmaceutical composition of the present disclosure can be administered orally or parenterally (such as, e.g., intravenous, intraarterial, intramuscular, subcutaneous, intraorgan, intranasal, intradermal, instillation, intracerebral, endorectal, intravaginal, intraperitoneal, intratumoral, near-tumor administrations, and the like) or administered directly to lesions.

In some embodiments, pharmaceutical compositions of the present disclosure may be controlled-release formulations, such as, e.g., quick release formulations or sustained release formulations (such as, e.g., sustained release microcapsules).

In some embodiments, pharmaceutical compositions of the present disclosure may be produced by a method commonly used in the pharmaceutical technology field, such as, e.g., the method described in the Japanese Pharmacopoeia.

In some embodiments, the content of a compound of the present disclosure in a pharmaceutical composition of the present disclosure may be, for example, about 0.1 to 100 wt %. The content of a compound of the present disclosure depends on the dosage form, the dosage of the compound, and the like.

In some embodiments, when an oral agent is produced, coating may be carried out for the purpose of masking the taste, improving an enteric property, or improving durability.

Non-limiting examples of coating bases include sugar coating bases, water-soluble film coating bases, enteric film coating bases, and sustained-release film coating bases.

In some embodiments, sucrose is used as a sugar coating base. In some embodiments, one or more types selected from talc, precipitated calcium carbonate, gelatin, gum arabic, pullulan, and Carnauba wax may be used together.

Non-limiting examples of water-soluble film coating bases include: cellulose-based high molecular weight molecules, such as, e.g., hydroxypropylcellulose, hydroxypropylmethylcellulose, hydroxyethylcellulose, and methylhydroxyethylcellulose; synthetic high molecular weight molecules, such as, e.g., polyvinyl acetal diethylaminoacetate, aminoalkyl methacrylate copolymer E [Eudragit E (trade name)], and polyvinylpyrrolidone; and polysaccharides, such as, e.g., pullulan.

Non-limiting examples of enteric film coating bases include: cellulose-based high molecular weight molecules, such as, e.g., hydroxypropylmethylcellulose phthalate, hydroxypropylmethylcellulose acetate succinate, carboxymethylethylcellulose, and cellulose phthalate acetate; acrylate-based high molecular weight molecules, such as, e.g., methacrylate copolymer L [Eudragit L (trade name)], methacrylate copolymer LD [Eudragit L-30D55 (trade name)], and methacrylate copolymer S [Eudragit S (trade name)]; and natural products such as, e.g., shellac.

Non-limiting examples of sustained-release film coating bases include: cellulose-based high molecular weight molecules, such as, e.g., ethyl cellulose; and acrylate-based high molecular weight molecules, such as, e.g., aminoalkyl methacrylate copolymer RS [Eudragit RS (trade name)] and ethyl acrylate-methyl methacrylate copolymer suspension [Eudragit NE (trade name)].

In some embodiments, coating bases described above may be used by mixing two or more types of the coating base in an appropriate ratio. In some embodiments, a light shielding agent such as titanium oxide and iron sesquioxide may be used for coating.

A compound of formula (I), a salt thereof, or a prodrug thereof may have an antagonistic action on a NMDA receptor containing a NR2B subunit. In some embodiments, the antagonistic action on an NMDA receptor containing a NR2B subunit is confirmed by, e.g., a suppressive effect on activation of the receptor (such as, e.g., glutamic acid-induced intracellular calcium ion ($Ca^{2+}$) influx).

In some embodiments, the NMDA receptor containing the NR2B subunit is a receptor composed of four subunits in total, including one NR2B subunit and further three subunits of two to three types chosen from NR1, NR2A, NR2B, NR2C, NR2D, NR3A, and NR3B.

In some embodiments, the NMDA receptor containing the NR2B subunit is a receptor composed of four subunits including a heterodimer of NR1 and NR2B, one type of subunit chosen from NR2A, NR2B, NR2C, and NR2D, and a heterodimer of NR1.

In some embodiments, the NMDA receptor containing the NR2B subunit is a receptor composed of four subunits consisting of two sets of heterodimers of NR1 and NR2B.

In some embodiments, a compound of formula (I), a salt thereof, or a prodrug thereof is expected show low toxicity (such as, e.g., cardiotoxicity, acute toxicity, chronic toxicity, genotoxicity, reproductive toxicity, pulmonary toxicity, and carcinogenicity) and less side effects (such as, e.g., psychotomimetic side effects). In some embodiments, a compound of formula (I), a salt thereof, or a prodrug thereof may be used as a prophylactic agent, a therapeutic agent, or a diagnostic agent for various diseases in mammals.

In some embodiments, a compound of formula (I), a salt thereof, or a prodrug thereof is expected to show low mutagenicity in the Ames tests and/or a low hERG (human ether-a-go-go-related gene) inhibition effect. In some embodiments, a compound of formula (I), a salt thereof, or a prodrug thereof is expected to show low extracerebral excretion via BCRP (breast cancer resistance protein) transporter and/or superior stability against conjugated metabolism.

In some embodiments, a compound of formula (I), a salt thereof, or a prodrug thereof is expected to have superior intracerebral transferability.

A compound of formula (I), a salt thereof, or a prodrug thereof may be used as a prophylactic or therapeutic agent for central and peripheral diseases. In some embodiments, a compound of formula (I), a salt thereof, or a prodrug thereof may be useful as a prophylactic or therapeutic agent for various diseases, such as, e.g.:

(1) psychiatric diseases (such as, e.g., major depression (including intractable major depression and treatment-resistant depression), minor depressive disorder, bipolar depression, recurrent depression, postpartum depression, stress disorder, major depressive disorder associated with psychosis (including delusional disorder and schizophrenia), manic or mixed mood episodes, hypomanic mood episodes, depression episodes with atypical features, depression episodes with melancholy features, depression episodes with tonic features, post-stroke depression episodes (the above are sometimes indicated as "depression" in the present specification), dysthymic disorder, emotional disorder (such as, e.g., seasonal affective disorder and the like), delirium, peripheral symptoms of dementia (such as, e.g., psychiatric symptoms or behavioral abnormalities), anxiety, generalized anxiety disorder, anxiety syndrome, anxiety neurosis, mood disorder, cyclothymic disorder, premenstrual dysphoric disorder, panic disorder, phobia, social phobia, social anxiety disorder, obsessive-compulsive disorder, post-traumatic stress syndrome, post-traumatic stress disorder, delusions or depressive schizoaffective disorder, paranoid personality disorder, Tourette syndrome, autism, fragile X syndrome, Rett syndrome, adjustment disorder, bipolar disorder (including type I bipolar disorder and type II bipolar disorder), neurosis, schizophrenia (such as, e.g., positive symptoms, negative symptoms, memory disorder, delusional schizophrenia, disassembled schizophrenia, catatonic schizophrenia, undifferentiated schizophrenia, and residual schizophrenia), schizophrenia-like disorders, chronic fatigue syndrome, obsessive-compulsive neurosis, epilepsy, pediatric refractory epilepsy syndrome, West syndrome, anxiety discomfort psychosis, emotional abnormalities, cyclothymia, nerve hypersensitivity, fainting, indulgence, decreased libido, attention deficit hyperactivity disorder (ADHD), psychotic disorders (such as, e.g., short-term psychotic disorders and shared psychotic disorders), alcohol-, amphetamines-, cannabis-, cocaine-, hallucinogens-, obesity-, inhalants-, opioids-, or phencyclidine-induced psychosis, delusional disorder, Noonan syndrome, Angelman syndrome, Prader-Willi syndrome, Beckwith-Wiedemann syndrome, Silver Russell syndrome, nodular sclerosis, Williams syndrome, Kallmann syndrome, Rubinstein-Taybi syndrome, movement disorder, mental retardation, paranoid tendency;

(2) neurodegenerative disease, such as, e.g., Alzheimer's disease, Alzheimer's type senile dementia, Parkinson's disease, Huntington's chorea, multiple cerebral infarction dementia, frontal-temporal dementia, Parkinson's type frontal-temporal dementia, alcoholic dementia, or other drug-related dementia, dementia associated with intracranial tumor or brain trauma, dementia associated with Huntington's disease or Parkinson's disease, neurodegeneration associated with brain trauma, neurodegeneration associated with stroke, neurodegeneration associated with cerebral infarction, neurodegeneration associated with hypoglycemia, neurodegeneration associated with epilepsy, neurodegeneration associated with neurotoxicity, multisystem atrophy, spinal cord injury, AIDS-related dementia, progressive nuclear paralysis, Pick syndrome, Niemann-Pick syndrome, corticobasal degeneration, Down syndrome, vascular dementia, Parkinson's disease after encephalitis, Lewy body dementia, HIV dementia, amyotrophic lateral sclerosis (ALS), motor neurogenic disease (MND), Creutzfeldt-Jakob disease or prion disease, cerebral palsy, multiple sclerosis, and neuromyopathy;

(3) amnestic disorder, mild cognitive impairment, learning disorder (such as, e.g., dyslexia, dysgraphia, and dyscalculia), and cognitive and memory impairment with aging (such as, e.g., age-related memory impairment and senile dementia);

(4) sleep disorder (such as, e.g., intrinsic sleep disorder (such as, e.g., psychophysiological insomnia, and the like), extrinsic sleep disorder, circadian rhythm disorder (such as, e.g., time zone change syndrome (jet lag), shift work sleep disorder, irregular sleep-wake pattern, sleep phase recession syndrome, sleep phase advance syndrome, non-24-hour sleep awakening, and the like), parasomnia, sleep disorder associated with internal or psychiatric disorder (such as, e.g., chronic obstructive pulmonary disease, Alzheimer's disease, Parkinson's disease, cerebrovascular dementia, schizophrenia, depression, and anxiety neurosis), stress insomnia, insomnia, insomnia neurosis, and sleep apnea syndrome;

(5) respiratory depression due to anesthetics, traumatic diseases, neurodegenerative diseases, or the like;

(6) pain, such as, e.g., psychogenic pain (such as, e.g., physical expression disorder, pain disorder, somatization disorder, hypochondria, conversion disorder, and chronic pain with depression), inflammatory pain, peripheral neuropathic pain, central neuropathic pain, neuropathic pain, acute pain, refractory pain, cancerous persistent pain, cancerous breakthrough pain, cancerous pain, persistent pain, physical pain, breakthrough pain, chronic pain, tenderness, general pain, dull pain, skin pain disease, radiating pain, pain, and post-thoracotomy pain syndrome;

(7) deafness, such as, e.g., kanamycin deafness, streptomycin deafness, toxic deafness, senile deafness, idiopathic bilateral sensorineural hearing loss, sudden deafness, acquired deafness, hereditary deafness, organic deafness, treble-sensorineural hearing loss, occupational deafness, and bass-sensorineural hearing loss;

(8) traumatic brain injury and associated disorder or complication thereof, post-concussion syndrome, infant shake syndrome, stroke, age-related macular degeneration, eye palatal tremor, spasm, phantom limb pain, radiation lethargic syndrome, nervous loss of appetite, eating disorder, nervous anorexia, hyperphagia, other eating disorders, alcoholism, alcohol abuse, alcoholic forgetfulness, alcohol delusions, alcohol preference, alcohol withdrawal, alcoholic psychosis, alcohol poisoning, alcoholic jealousy, alcoholic manic psychosis, alcohol-dependent mental disorder, hepatic encephalopathy, drug preference, drug phobia, drug enthusiast, drug abuse, drug dependence, drug withdrawal, migraine, stress headache, tension headache, diabetic neuropathy, obesity, diabetes, muscle spasm, Meniere's disease, autonomic imbalance, alopecia, glaucoma, hypertension, heart disease, tachycardia, congestive heart failure, hyperventilation, bronchial asthma, apnea, sudden infant death syndrome, inflammatory disease, allergic disease, systemic lupus erythematosus, impotence, menopausal disorder, infertility, cancer, immunodeficiency syndrome due to HIV infection, immunodeficiency syndrome due to stress, cerebrospinal fever, terminal hypertrophy, incontinence, metabolic syndrome, osteoporosis, digestive ulcer, irritable bowel syndrome, inflammatory bowel disease, ulcerative colitis, Crohn's disease, stress gastrointestinal disorder, nervous vomiting, diarrhea, constipation, and postoperative ileus.

In some embodiments, a compound of formula (I), a salt thereof, or a prodrug thereof may be useful for the prevention or treatment of depression (including major depression, intractable depression, treatment-resistant depression, and the like), bipolar disorder, migraine, pain, or peripheral symptoms of dementia.

Both depression and bipolar disorder may be characterized by a depressive state, or a depressive state and a manic state for a long period of time. In recent years, it has been found that the intravenous single administration of ketamine, an NMDA receptor antagonist, rapidly and continuously improves depression symptoms associated with major depression and bipolar disorder [Therapeutic Advances in Psychopharmacology (Ther. Adv. Psychopharmacol.) Vol. 4, page 75 to 99, 2014]. In addition, it has been reported that treatment-resistant depression symptoms are significantly improved by continuous intravenous administration of CP-101,606 which are antagonists to the NMDA receptor containing the NR2B subunit [Journal of Clinical Psychopharmacology (J. Clin. Psychopharmacol.) Vol. 28, page 631 to 637, 2008]. Therefore, the compound of the present disclosure is promising as a prophylactic or therapeutic agent for treatment-resistant depression.

A migraine is a chronic and paroxysmal primary headache. The onset mechanism is unknown, but it is thought to occur along with abnormalities of central nervous system processing, abnormalities of the trigeminal neurovascular system, or the like. In the study of the pathophysiological process of migraines, especially aura thereof, the cortical spreading depression phenomenon (cortical spreading depression) has attracted attention. In an experimental cortical spreading depression test using rodents, it has been reported that CP-101,606 and Ro25-6981, which are antagonists for the NMDA receptor containing the NR2B subunit, suppress the number of occurrences of and the depth of cortical spreading depression [The Journal of Pharmacology and Experimental Therapeutics (J. Pharmacol. Exp. Ther.) Vol. 321, page 564 to 572, 2007]. Therefore, a compound of formula (I), a salt thereof, or a prodrug thereof may be useful as a prophylactic or therapeutic agent for migraines.

Pain is classified into acute pain, in which the pain is sustained for a relatively short period of time, and into chronic pain in which the pain is sustained for three months or longer or reoccurs, the pain is sustained for more than a month after recovery of acute tissue damage, or an accompanying lesion which is not cured is observed. The NMDA receptor containing the NR2B subunit is highly expressed in the posterior horn of the spinal cord, which plays an important role in the reception of pain. It has been suggested that pain may be controlled by functional control of the NMDA receptor containing the NR2B subunit. In fact, it has been reported that the pain threshold value is increased by gene modification operation which causes the lowering of the function of the NR2B subunit [European Journal of Neuroscience (Eur. J. Neurosci.) Vol. 32, page 798 to 810, 2010]. Additionally, it has reported that the pain threshold value is increased by Ifenprodil, which is an antagonist of the NMDA receptor containing the NR2B subunit [Pain (Pain), Vol. 153, page 1022 to 1029, 2012]. Therefore, a compound of formula (I), a salt thereof, or a prodrug thereof may be useful as a prophylactic or therapeutic agent for pain.

Dementia is a chronic, general, and usually irreversible decline in cognitive ability. The quality of life reduction in patients caused by a decrease in cognitive ability is notable, but peripheral symptoms of dementia (such as, e.g., mental symptoms or behavioral abnormalities) are also considered to be a significant factor in lowering patient and/or caregiver quality of life. Although there is no effective therapeutic intervention for the peripheral symptoms of dementia, it has been reported that the peripheral symptoms of dementia are partially ameliorated by the administration of memantine, an antagonist of the NMDA receptor [The Annals of Pharmacotherapy (Ann. Pharmacother.) Vol. 42, page 32 to 38, 2007]. NMDA receptors containing the NR2B subunits are widely distributed throughout brain regions other than the cerebellum, but the peripheral symptoms of dementia are reported to be related to white matter abnormalities in brain regions other than the cerebellum [Journal of the Neurological Sciences (J. Neurol. Sci.) Vol. 337, page 162 to 166, 2014]. Therefore, a compound of formula (I), a salt thereof, or a prodrug thereof may be useful as a prophylactic or therapeutic agent for peripheral symptoms of dementia.

The dosage of a compound of formula (I), a salt thereof, or a prodrug thereof may vary depending on the object of administration, route of administration, target disease, symptoms, or the like, but, for example, when oral or parenteral administration is carried out to an adult patient, a usual amount for a single time may be about 0.01 to 100 mg/kg of body weight, such as, e.g., 0.1 to 50 mg/kg of body weight, such as, e.g., 0.5 to 20 mg/kg of body weight, and the amount can be administered one to three times a day.

A compound of formula (I), a salt thereof, or a prodrug thereof may be used in combination with other active ingredients (hereinafter, abbreviated as a concomitant drug).

Non-limiting examples of concomitant drugs include the following drugs: an acetylcholinesterase inhibitor (such as, e.g., donepezil, rivastigmine, galantamine, and zanapezil), a nootropic (such as, e.g., memantine), a β-amyloid protein production, secretion, accumulation, aggregation, and/or deposition suppressor, a β-secretase inhibitor (for example, 6-(4-biphenylyl) methoxy-2-[2-(N,N-dimethylamino) ethyl] tetraline, 6-(4-biphenylyl) methoxy-2-(N,N-dimethylamino) methyltetraline, 6-(4-biphenylyl) methoxy-2-(N,N-dipropylamino) methyltetraline, 2-(N,N-dimethylamino) methyl-6-(4'-methoxybiphenyl-4-yl) methoxytetraline, 6-(4-bifeniryl) methoxy-2-[2-(N,N-diethylamino) ethyl] tetraline, 2-[2-(N, N-dimethylamino) ethyl]-6-(4'-methylbiphenyl-4-yl) methoxytetraline, 2-[2-(N,N-dimethylamino) ethyl]-6-(4'-methoxybiphenyl-4-yl) methoxytetraline, 6-(2',4'-dimethoxybiphenyl-4-yl) methoxy-2-[2-(N,N-dimethylamino) ethyl] tetraline, 6-[4-(1,3-benzodioxol-5-yl) phenyl] methoxy-2-[2-(N,N-dimethylamino) ethyl] tetraline, 6-(3', 4'-dimethoxybiphenyl-4-yl) methoxy-2-[2-(N,N-dimethylamino) ethyl] tetraline, an optical active substance thereof, a salt thereof, and a hydrate thereof, and OM99-2 (WO 01/00663)), a γ-secretase inhibitor, a β-amyloid protein aggregation inhibitor (for example, PTI-00703, ALZHEMED (NC-531), PPI-368 (JP H11-514333 T), PPI-558 (JP 2001-500852 T), SKF-74652 (Biochem. J. (1999), 340 (1), 283-289)), a brain function activator such as a β-amyloid vaccine and a β-amyloid degrading enzyme, (such as, e.g., aniracetam and nicergoline), a therapeutic for Parkinson's disease (such as, e.g., a dopamine receptor agonist (such as, e.g., L-dopa, bromocriptine, pergolide, talipexole, pramipexole, cabergoline, and amantadine), a monoamyloid oxidase (MAO) inhibitor (such as, e.g., deprenil, selegiline (selegiline), remasemide, and riluzol), an anticholinergic agent (such as, e.g., trihexyphenidyl and biperiden), a COMT inhibitor (such as, e.g., entacapone)), a therapeutic agent for amyotrophic lateral sclerosis (such as, e.g., a neurotrophic factor such as riluzol), a therapeutic agent for abnormal behavior associated with the progression of dementia, wandering, and the like (such as, e.g., a sedative and an anxiolytic), an apoptosis inhibitor (such as, e.g., CPI-1189, IDN-6556, and CEP-1347), nerve differentiation/regeneration promoter (such as, e.g., leteprinim, xaliproden (xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl] isoindoline, 5,6-dimethoxy-2-[3-(4-isopropylphenyl)-2,2,4,6,7-pentamethyl-2,3-dihydro-1-benzofuran-5-yl] isoindoline, 6-[3-(4-isopropylphenyl)-2,2,4,6,7-pentamethyl-2,3-dihydro-1-benzofuran-5-yl]-6,7-dihydro-5H-[1,3] dioxolo [4,5-f] isoindole and an optically active substance thereof, a salt thereof, and a hydrate thereof), a non-steroidal anti-inflammatory drug (such as, e.g., meloxicam, tenoxicam, indomethacin, ibuprofen, celecoxib, rofecoxib, aspirin, indomethacin, and the like), a steroid drug (such as, e.g., dexamethasone, hexestrol, cortisone acetate, and the like), disease-modifying antirheumatic drugs (DMARDs), an anti-cytokine drug (such as, e.g., a TNF inhibitor and a MAP kinase inhibitor), a therapeutic agent for urinary incontinence/frequent urine (such as, e.g., flavoxate hydrochloride, oxybutinine hydrochloride, and propiverine hydrochloride), a phosphodiesterase inhibitor (such as, e.g., sildenafil (citrate)), a dopamine agonist (such as, e.g., apomorphine), an anti-arrhythmic drug (such as, e.g., mexiletine), a sex hormone or a derivative thereof (such as, e.g., progesterone, estradiol, and estradiol benzoate), a therapeutic agent for osteoporosis (such as, e.g., alfacalcidol, calcitriol, elcatonin, salmon calcitonin, estriol, ipriflavone, disodium pamidronate, sodium alendronate hydrate, and disodium Incadronate), parathyroid hormone (PTH), a calcium receptor antagonist, a therapeutic agent for insomnia (such as, e.g., a benzodiazepine drug, a non-benzodiazepine drug, a melatonin agonist, and an orexin receptor antagonist), a schizophrenia drug (such as, e.g., a typical antipsychotic, such as, e.g., haloperidol; an atypical antipsychotic, such as, e.g., clozapine, olanzapine, risperidone, and aripiprazole; a drug that affects the metabolic glutamate receptor or the ion channel conjugated glutamate receptor; and a phosphodiesterase inhibitor), a benzodiazepine drug (such as, e.g., chlordiazepoxide, diazepam, potassium clorazepate, lorazepam, alprazolam, and the like), an L-type calcium channel inhibitor (such as, e.g., pregabalin and the like), a tricyclic or tetracyclic antidepressant drug (such as, e.g., imipramine hydrochloride, amitriptyline hydrochloride, clomipramine hydrochloride, mianserin hydrochloride, setiptiline maleate salt, and the like), a selective serotonin reuptake inhibitor (such as, e.g., fluvoxamine maleate, fluoxetine hydrochloride, citalopram hydrobromide, escitalopram oxalate, sertraline hydrochloride, paroxetine hydrochloride hydrate, and the like), a serotonin-noradrenaline reuptake inhibitor (such as, e.g., venlafaxine hydrochloride, duloxetine hydrochloride, desvenlafaxine, and the like), a noradrenaline reuptake inhibitor (such as, e.g., reboxetine mesylate and the like), mirtazapine, trazodone hydrochloride, bupropion hydrochloride, a $5-HT_{1A}$ agonist (such as, e.g., buspirone hydrochloride, tandospirone citrate, osemozotan hydrochloride, and the like), a $5-HT_{2A}$ antagonist, a $5-HT_{2A}$ inverse agonist, a $5-HT_3$ antagonist (such as, e.g., cyamemazine and the like), a non-cardiac-selective β-inhibitor (such as, e.g., propranolol hydrochloride, oxprenolol hydrochloride, and the like), a histamine $H_1$ antagonist, a CRF antagonist, other anti-anxiety agents (such as, e.g., meprobamate and the like), a tachykinin antagonist, a drug that affect to the metabolic glutamate receptor, a CCK antagonist, a β3 adrenaline antagonist (such as, e.g., amibegron hydrochloride and the like), a GAT-1 inhibitor, an N-type calcium channel inhibitor, a type-2 carbonate dehydrogenase inhibitor, a NMDA glycine site agonist, a NMDA antagonist (such as, e.g., memantine, ketamine, amphetamine, and the like), a peripheral benzodiazepine receptor agonist, a vasopressin receptor antagonist, a phosphodiesterase inhibitor, an opioid antagonist, an opioid agonist, uridine, a nicotinic acid receptor agonist, thyroid hormone, thyroid stimulating hormone (TSH), thyroid stimulating hormone releasing hormone (TRH), a MAO inhibitor (such as, e.g., phenelzine sulfate, tranylcypromine sulfate, moclobemide, and the like), a bipolar disorder therapeutic agent (such as, e.g., lithium carbonate, sodium valproate, lamotrigine, riluzole, felbamate, and the like), a cannabinoid CB1 antagonist, a FAAH inhibitor, a sodium channel inhibitor, an anti-ADHD drug (such as, e.g., methylphenidate hydrochloride, methamphetamine hydrochloride, and the like), an alcoholism drug, an autism drug, a chronic fatigue syndrome drug, a spasm drug, a fibromyalgia drug, a headache drug, a drug for smoking cessation, a myasthenia gravis drug, a cerebral infarction drug, a mania drug, a hypersomnia drug, a pain drug, a dysthymia drug, an autonomic imbalance drug, a drug for male and female sexual dysfunction, a migraine drug, a drug for pathological gambling, a lower limb immobility syndrome drug, a substance addiction drug, a drug for alcohol-related disease, a drug for hypersensitivity bowel syndrome, a lipid disorder drug, such as, e.g., cholesterol-lowering drugs (such as, e.g., statins and the like), fibrates, and a squalene synthesis inhibitor), an abnormal behavior drug or a suppressing agent for wandering habits due to dementia (such as, e.g., a sedative, an anti-anxiety drug, and the like), an anti-obesity drug, an antidiabetic drug, a drug for diabetic complication, a hypertension drug, a hypotension drug, a diuretic, a chemotherapeutic agent, an immunotherapeutic agent, an antithrombotic agent, an anticancer agent, an antibody drug, a nucleic acid or a nucleic acid derivative, an aptamer drug, and the like.

The concomitant drugs described above may be used by combining two or more types at an appropriate ratio.

Furthermore, when a compound of formula (I), a salt thereof, or a prodrug thereof is used in the treatment or preventing of any of the diseases described above, the compound, salt, or prodrug may be used in combination with a biological formulation (such as, e.g., an antibody drug, a nucleic acid or a nucleic acid derivative, an aptamer drug, and a vaccine formulation), in combination with a gene therapy and the like, or in combination with a treatment in a psychiatric area without drugs.

Examples of treatment in a psychiatric area without drugs include modified electroconvulsive therapy, deep brain stimulation therapy, repeated transcranial magnetic stimulation therapy, and psychotherapy including cognitive behavioral therapy.

In some embodiments, a compound of formula (I), a salt thereof, or a prodrug thereof may be used in combination with various organ regeneration methods, such as, e.g., cardiac regeneration, renal regeneration, pancreatic regeneration, and vascular regeneration, a cell transplantation therapy using bone marrow cells (such as, e.g., marrow mononuclear cell and marrow stem cell), and artificial organs (such as, e.g., artificial blood vessel and cardiac muscle cell sheet) using tissue engineering.

By combining a compound of formula (I), a salt thereof, or a prodrug thereof with a concomitant drug, (1) the dosage can be reduced as compared with the case of single administration of a compound of formula (I), a salt thereof, or a prodrug thereof or the concomitant drug;

(2) depending on the symptoms of the patient (mild, severe, or the like), a compound of formula (I), a salt thereof, or a prodrug thereof and the concomitant drug can be selected;

(3) the treatment period can be set to a long period by selecting a concomitant drug having a different mechanism of action from a compound of formula (I), a salt thereof, or a prodrug thereof;

(4) the therapeutic effect can be sustained by selecting a concomitant drug having a different mechanism of action from a compound of formula (I), a salt thereof, or a prodrug thereof; and (5) by using the compound of the present disclosure and the concomitant drug in combination, excellent effects such as a synergistic effect can be obtained.

Hereinafter, the combined use of a compound of formula (I), a salt thereof, or a prodrug thereof and the concomitant drug is referred to as a "combination therapy of the present disclosure."

When using a combination therapy of the present disclosure, the administration time of a compound of formula (I), a salt thereof, or a prodrug thereof and the concomitant drug is not limited, and a compound of formula (I), a salt thereof, or a prodrug thereof or a pharmaceutical composition comprising the same and the concomitant drug or a pharmaceutical composition comprising the same may be simultaneously administered to the administration subject (as a single formulation or as separate formulations), or may be administered at different times. In the case of administering at a difference time, for the order of administration, either of a compound of formula (I), a salt thereof, or a prodrug thereof or the concomitant drug may be administered earlier. Moreover, a compound of formula (I), a salt thereof, or a prodrug thereof may be administered after continuously administering the concomitant drug for a fixed period.

The dosage of the concomitant drug may be based on the dosage clinically used, and may be appropriately selected depending on the administration target, administration route, disease, combination, and the like.

The dosage of the concomitant drug may be selected as appropriate based on the dosage clinically used. Further, the blending ratio of a compound of formula (I), a salt thereof, or a prodrug thereof and the concomitant drug may be appropriately selected according to the administration target, administration route, target disease, symptoms, combination, and the like.

Methods for producing a compound of formula (I) are described below.

The starting materials and reagents used in each step of the following production methods and the obtained compounds may each form a salt. Examples of such salts include salts similar to the aforementioned salts of the compound of the present disclosure, and the like.

When the compound obtained in each step is a free compound, the compound may be converted into the target salt by a method known to those of ordinary skill in the art. Conversely, when the compound obtained in each step is a salt, the compound may be converted into a free body or other type of salt of object by a method known by those of ordinary skill in the art.

The compound obtained in each step may be used in the next reaction as the reaction mixture thereof or, after it is obtained, as a crude product thereof. Alternatively, the compound obtained in each step can be isolated and/or purified from the reaction mixture by separation means, such as, e.g., concentration, crystallization, recrystallization, distillation, solvent extraction, fractionation, chromatography, or the like, according to conventional methods in the art to which this disclosure pertains.

When the starting materials for each step and reagents are commercially available, the commercially available products can be used as they are.

In the reaction of each step, reaction time may differ depending on the reagents or solvents used, but unless otherwise noted, it is normally 1 minute to 48 hours, such as, e.g., 10 minutes to 8 hours.

In the reaction of each step, reaction temperature may differ depending on the reagents or solvents used, but unless otherwise noted, it is normally −78° C. to 300° C., such as, e.g., −78° C. to 150° C.

In the reaction of each step, pressure may differ depending on the reagents or solvents used, but unless otherwise noted, it is normally 1 atm to 20 atm, such as 1 atm to 3 atm.

In the reaction of each step, for example, a microwave synthesis device such as Initiator manufactured by Biotage may be used. Reaction temperature may differ depending on the reagents or solvents used, but unless otherwise noted, it is normally room temperature to 300° C., such as, e.g., 50° C. to 250° C. Reaction time may differ depending on the reagents or solvents used, but unless otherwise noted, it is normally 1 minute to 48 hours, such as, e.g., 1 minute to 8 hours.

In the reaction of each step, unless otherwise noted, a reagent may be used in an amount of 0.5 equivalents to 20 equivalents, such as, e.g., 0.8 equivalents to 5 equivalents, relative to the substrate. When a reagent is used as a catalyst, the reagent may be used in an amount of 0.001 equivalents to 1 equivalent, such as, e.g., 0.01 equivalents to 0.2 equivalents, relative to the substrate. When a reagent also serves as a reaction solvent, the reagent may be the used in the amount of a solvent.

In the reaction of each step, unless otherwise noted, reactions are performed in the absence of a solvent or by dissolving or suspending in a suitable solvent. Non-limiting examples of solvents include the solvents described in the Examples and in the following:

alcohols: methanol, ethanol, tert-butyl alcohol, 2-methoxyethanol, and the like;

ethers: diethyl ether, diphenyl ether, tetrahydrofuran, 1,2-dimethoxyethane, and the like;

aromatic hydrocarbons: chlorobenzene, toluene, xylene, and the like;

saturated hydrocarbons: cyclohexane, hexane, and the like;

amides: N,N-dimethylformamide, N-methylpyrrolidone, and the like;

halogenated hydrocarbons: dichloromethane, carbon tetrachloride, and the like;
nitriles: acetonitrile, and the like;
sulfoxides: dimethyl sulfoxide, and the like;
aromatic organic bases: pyridine, and the like;
anhydrides: acetic anhydride, and the like;
organic acids: formic acid, acetic acid, trifluoroacetic acid, and the like;
inorganic acids: hydrochloric acid, sulfuric acid, and the like;
esters: ethyl acetate, and the like;
ketones: acetone, methyl ethyl ketone, and the like; and
water.

The foregoing solvents may be used by mixing two or more kinds at appropriate ratios.

When a base is used in the reaction of each process, a base shown below or a base described in the Examples may be used:
inorganic bases: sodium hydroxide, magnesium hydroxide, sodium carbonate, calcium carbonate, sodium hydrogen carbonate, and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, and the like;
metal alkoxides: sodium ethoxide, potassium tert-butoxide, and the like;
alkali metal hydrides: sodium hydride, and the like;
metal amides: sodium amide, lithium diisopropylamide, lithium hexamethyldisilazide, and the like; and
organolithium: n-butyl lithium and the like.

When an acid or an acidic catalyst is used in the reaction of each process, an acid or acidic catalyst shown below or an acid or acidic catalyst described in the Examples may be used:
inorganic acids: hydrochloric acid, sulfuric acid, nitric acid, hydrobromic acid, phosphoric acid, and the like;
organic acids: acetic acid, trifluoroacetic acid, citric acid, p-toluenesulfonic acid, 10-camphor sulfonic acid, and the like; and
Lewis acids: boron trifluoride diethyl ether complex, zinc iodide, anhydrous aluminum chloride, anhydrous zinc chloride, anhydrous iron chloride, and the like.

The reaction of each step is, unless otherwise stated, performed according to a method known by those of ordinary skill in the art, including, e.g., a method described in: Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry, Revised 2nd Edition (L. F. Tietze, Th. Eicher, Nankodo); Revised Organic Name Reactions: Mechanisms and Essence (by Hideo Togo, Kodansha); ORGANIC SYNTHESES Collective Volumes I to VII (John Wiley & Sons Inc); Modern Organic Synthesis in the Laboratory A Collection of Standard Experiential Procedures (by Jie Jack Li, published by OXFORD UNIVERSITY); Comprehensive Heterocyclic Chemistry III, Vol. 1 to Vol. 14 (Elsevier Japan KK); Strategic Applications of Named Reactions in Organic Synthesis (translation supervised by Kiyoshi Tomioka, published by Kagaku-Dojin); or Comprehensive Organic Transformations (VCH Publishers Inc.), published 1989; or the like; or a method described in the Examples.

In each step, a protection or deprotection reaction on a functional group is performed according to a method known to those of ordinary skill in the art, such as, e.g., a method described in: "Protective Groups in Organic Synthesis, 4th Ed.," published by Wiley-Interscience in 2007 (by Theodora W. Greene and Peter G. M. Wuts); "Protecting Groups 3rd Ed.," published by Thieme in 2004 (by P. J. Kocienski); or the like, or a method described in the Examples.

Non-limiting examples of protecting groups for hydroxyl groups such as alcohols and phenolic hydroxyl groups include: ether protecting groups, such as, e.g., methoxymethyl ether, benzyl ether, tert-butyldimethylsilyl ether, tetrahydropyranyl ether; carboxylate ester protecting groups, such as, e.g., acetate esters; sulfonate ester protecting groups, such as, e.g., methanesulfonate esters; carbonate ester protecting groups, such as, e.g., tert-butyl carbonate.

Non-limiting examples of protecting groups for carbonyl group of aldehyde include: acetal protecting groups, such as, e.g., a dimethyl acetal; cyclic acetal protecting groups, such as, e.g., 1,3-dioxane; and the like.

Non-limiting examples of protecting groups for carbonyl group of ketone include: ketal protecting groups, such as, e.g., dimethyl ketal; cyclic ketal protecting groups, such as, e.g., 1,3-dioxane; oxime protecting groups, such as, e.g., O-methyloxime; hydrazone protecting groups such as, e.g., N,N-dimethylhydrazone; and the like.

Non-limiting examples of protecting groups for carboxyl groups include: ester protecting groups, such as, e.g., methyl esters; amide protecting groups, such as, e.g., N,N-dimethylamide; and the like.

Non-limiting examples of protecting groups for thiols include: ether protecting groups, such as, e.g., benzyl thioether; ester protecting groups, such as, e.g., thioacetate esters, thiocarbonates, and thiocarbamates; and the like.

Non-limiting examples of protecting groups for amino groups and aromatic heterocycles such as imidazole, pyrrole, and indole include: carbamate protecting groups, such as, e.g., benzyl carbamate and tert-butyl carbamate; amide protecting groups, such as, e.g., acetamide; alkylamine protecting groups, such as, e.g., N-triphenylmethylamine; sulfonamide protecting groups, such as, e.g., methanesulfonamide; 2-(trimethylsilyl)ethoxymethyl groups; and the like.

Removal of protecting groups can be performed using a method known to those of ordinary skill in the art, such as, e.g., a method using an acid, a base, ultraviolet light, hydrazine, phenylhydrazine, sodium N-methyldithiocarbamate, tetrabutylammonium fluoride, palladium acetate, trialkylsilyl halide (such as, e.g., trimethylsilyl iodide, trimethylsilyl bromide), a reduction method, or the like.

In each step, when performing a reduction reaction, non-limiting examples of reducing agents include: metal hydrides, such as, e.g., lithium aluminum hydride, sodium triacetoxyborohydride, sodium cyanoborohydride, diisobutylaluminum hydride (DIBAL-H), sodium borohydride, and tetramethylammonium triacetoxyborohydride; boranes, such as, e.g., borane tetrahydrofuran complex; Raney nickel; Raney cobalt; hydrogen; formic acid; triethylsilane; and the like. When reducing a carbon-carbon double bond or triple bond, there are methods of using a catalyst such as palladium-carbon or a Lindlar catalyst. Furthermore, when reducing a nitro group, there are methods such as using a catalyst such as rhodium-carbon in the presence of iron(II) acetate. Moreover, when reducing an azide group, there are methods such as using triphenylphosphine in the presence of water.

In each step, when performing an oxidation reaction, non-limiting examples of oxidizing agents include: peracids, such as, e.g., m-chloroperbenzoic acid (mCPBA), hydrogen peroxide, potassium peroxymonosulfate (OXONE®), and tert-butyl hydroperoxide; perchlorates, such as, e.g., tetrabutylammonium perchlorate; chlorates, such as, e.g., sodium chlorate; chlorites, such as, e.g., sodium chlorite; periodic acids, such as, e.g., sodium periodate; high valence iodine reagents, such as, e.g., iodosylbenzene; reagents containing manganese, such as, e.g., manganese dioxide and potassium permanganate; leads, such as, e.g., lead tetraacetate; reagents containing chromium, such as, e.g., pyridinium chlorochromate (PCC), pyridinium dichromate (PDC), and Jones reagents; halogen compounds, such as, e.g., N-bromosuccinimide (NBS); oxygen; ozone; sulfur trioxide-pyridine complexes; osmium tetroxide; selenium dioxide; 2,3-dichloro-5,6-dicyano-1,4-benzoquinone (DDQ); and the like.

In each step, when performing a radical cyclization reaction, non-limiting examples of radical initiators include: azo compounds, such as, e.g., azobisisobutyronitrile (AIBN); water-soluble radical initiators, such as, e.g., 4-4'-azobis-4-cyanopentanoic acid (ACPA); triethylboron in the presence of air or oxygen; benzoyl peroxide; and the like. Furthermore, non-limiting examples of radical reagents include tributylstannane, tris(trimethylsilyl)silane, 1,1,2,2-tetraphenyldisilane, diphenylsilane, samarium iodide, and the like.

In each step, when performing a Wittig reaction, non-limiting examples of the Wittig reagent include alkylidene phosphoranes and the like. Alkylidene phosphoranes can be prepared by methods known per se, for example, reacting a phosphonium salt with a strong base.

In each step, when performing a Horner-Emmons reaction, non-limiting examples of the reagents include: phosphonoacetic esters such as methyl dimethylphosphonoacetate and ethyl diethylphosphonoacetate; bases such as an alkali metal hydrides or organolithium; and the like In each step, when performing a Friedel-Crafts reaction, non-limiting examples of the reagents include a combination of a Lewis acid and an acid chloride or a combination of a Lewis acid and an alkylating agent (such as, e.g., alkyl halides, alcohols, olefins, and the like). Alternatively, an organic acid or an inorganic acid may be used instead of a Lewis acid, and an acid anhydride such as acetic anhydride may be used instead of an acid chloride.

In each step, when performing an aromatic nucleophilic substitution reaction, a nucleophilic agent (for example, phenols, amines, imidazole, and the like) and a base (for example, inorganic bases, organic bases, and the like) may be used as the reagent.

In each step, when performing a nucleophilic addition reaction using a carbanion, a nucleophilic 1,4-addition reaction using a carbanion (Michael addition reaction), or a nucleophilic substitution reaction using a carbanion, non-limiting examples of bases used to generate carbanions include organolithium, metal alkoxides, inorganic bases, organic bases, and the like.

In each step, when performing a Grignard reaction, non-limiting examples of Grignard reagents include arylmagnesium halides such as phenylmagnesium bromide; and alkylmagnesium halides such as methylmagnesium bromide. The Grignard reagent can be prepared by methods known per se, such as, e.g., reacting an alkyl halide or aryl halide with metal magnesium in the presence of an ether or tetrahydrofuran as a solvent.

In each step, when performing a Knoevenagel condensation reaction, an active methylene compound (such as, e.g., malonic acid, diethyl malonate, malononitrile, or the like) and base (such as, e.g., organic bases, metal alkoxides, and inorganic bases) sandwiched between two electron attracting groups may be used as reagents.

In each step, when performing a Vilsmeier-Haack reaction, a combination of phosphoryl chloride and an amide derivative (such as, e.g., N, N-dimethylformamide or the like) or (chloromethylene)dimethyliminium chloride (Vilsmeier reagent) may be used as a reagent.

In each step, when performing an azidation reaction of alcohols, alkylhalides, or sulfonate esters, non-limiting examples of azidation agents include diphenylphosphoryl azide (DPPA), trimethylsilyl azide, sodium azide, and the like. For example, when azidizing alcohols, there are methods for using diphenylphosphoryl azide and 1,8-diazabicyclo[5.4.0]undec-7-ene (DBU), methods for using trimethylsilyl azide and a Lewis acid, and the like.

In each step, when performing a reductive amination reaction, non-limiting examples of reducers include sodium triacetoxyborohydride, borane-2-methylpyridine complexes, sodium cyanoborohydride, hydrogen, formic acid, and the like. When the substrate is an amine compound, non-limiting examples of carbonyl compounds include not only paraformaldehyde but also aldehydes such as acetaldehyde and ketones such as cyclohexanone. When the substrate is a carbonyl compound, examples of amines include: primary amines such as ammonia and methylamine; and secondary amines such as dimethylamine.

In each step, when performing a Mitsunobu reaction, azodicarboxylate esters (such as, e.g., diethyl azodicarboxylate (DEAD), diisopropyl azodicarboxylate (DIAD), and the like) and triphenylphosphine may be used as reagents.

In each step, when performing an esterification reaction, an amidation reaction, or a urea conversion reaction, non-limiting examples of reagents include: halogenated acyl forms such as acid chlorides and acid bromides; and activated carboxylates such as acid anhydrides, active esters, and sulfate esters. When performing an amidation reaction using a non-activated ester, trimethylaluminum or the like may be used as an activator. Examples of carboxylic acid activators include: carbodiimide-based condensing agents, such as, e.g., 1-ethyl-3-(3-dimethylaminopropyl)carbodiimide hydrochloride (WSCD); triazine-based condensing agents, such as, e.g., 4-(4,6-dimethoxy-1,3,5-triazine-2-yl)-4-methylmorpholinium chloride-n-hydrate (DMT-MM); carbonate ester-based condensing agents, such as, e.g., 1,1-carbonyldiimidazole (CDI); diphenylphosphoryl azide (DPPA); benzotriazol-1-yloxy-tris(dimethylamino)phosphonium salts (BOP reagents); 2-chloro-1-methyl-pyridinium iodide (Mukaiyama reagent); thionyl chloride; lower alkyl halides, such as, e.g., ethyl chloroformate; 0-(7-azabenzotriazol-1-yl)-N,N,N',N'-tetramethyluronium hexafluorophosphate (HATU); sulfuric acid; or a combination of these. When using a carbodiimide-based condensing agent, additives such as, e.g., 1-hydroxybenzotriazole (HOBt), N-hydroxysuccinimide (HOSu), and dimethylaminopyridine (DMAP) may be further added to the reaction.

In each step, when performing a coupling reaction, non-limiting examples of metal catalysts include: palladium compounds, such as, e.g., palladium(II) acetate, tetrakis(triphenylphosphine)palladium(0), dichlorobis(triphenylphosphine)palladium(II), dichlorobis(triethylphosphine)palladium (II), tris(dibenzylideneacetone)dipalladium (0), [1,1'-bis(diphenylphosphino)ferrocene]palladium(II) chloride; nickel compounds, such as, e.g., tetrakis(triphenylphosphine)nickel(0); rhodium compounds, such as, e.g., tris(triphenylphosphine)rhodium(III) chloride; cobalt compounds; copper compounds, such as, e.g., copper oxide and copper(I) iodide; and platinum compounds. Additionally, a base may be added to the reaction, and examples of such bases include inorganic bases and the like.

In each step, when performing a thiocarbonylation reaction, diphosphorus pentasulfide may be used as the thiocarbonylation agent, but other than diphosphorus pentasulfide, reagents having 1,3,2,4-dithiadiphosphetane-2,4-disulfide structures such as 2,4-bis(4-methoxyphenyl)-1,3,2,4-dithiadiphosphetane-2,4-disulfide (Lawesson's reagent) may be used.

In each step, when performing a Wohl-Ziegler reaction, non-limiting examples of halogenating agents include N-iodosuccinimide, N-bromosuccinimide (NBS), N-chlorosuccinimide (NCS), bromine, sulfuryl chloride, and the like. Additionally, by adding radical initiators such as heat, light, benzoyl peroxide, or azobisisobutyronitrile to the reaction, the reaction can be accelerated.

In each step, when performing a halogenation reaction of a hydroxyl group, non-limiting examples of halogenating agents include acid halides of hydrohalogenic acids and inorganic acids, specifically, hydrochloric acid, thionyl chloride, phosphorus oxychloride, and the like when chlorinated and 48% hydrobromic acid and the like when brominated. Furthermore, methods for obtaining alkyl halides from alcohols may be used by the action between triphenylphosphine and carbon tetrachloride, carbon tetrabromide, or the like. Alternatively, a method for synthesizing an alkyl halide via a two-step reaction such as converting an alcohol into a sulfonate ester and then reacting with lithium bromide, lithium chloride, or sodium iodide may be used.

In each step, when performing an Arbuzov reaction, non-limiting examples of reagents include: alkyl halides, such as, e.g., ethyl bromoacetate; and phosphites, such as, e.g., triethyl phosphite, tri(isopropyl) phosphite, and the like.

In each step, when performing a sulfonate esterification reaction, non-limiting examples of sulfonylating agents include methanesulfonyl chloride, p-toluenesulfonyl chloride, methanesulfonate anhydride, trifluoromethanesulfonate anhydride, p-toluenesulfonate anhydride, and the like.

In each step, when performing a hydrolysis reaction, an acid or base may be used as a reagent. Furthermore, when performing an acid hydrolysis reaction of a tert-butyl ester, formic acid, triethylsilane, or the like may be added to reductively trap a tert-butyl cation, which is generated as a byproduct.

In each step, when performing a dehydration reaction, non-limiting examples of dehydrating agents include sulfuric acid, diphosphorus pentoxide, phosphorus oxychloride, N,N'-dicyclohexylcarbodiimide, alumina, polyphosphoric acid, and the like.

In each step, when performing an alkylation reaction, non-limiting examples of bases include potassium carbonate, tripotassium phosphate, triethylamine, N,N-diisopropylethylamine, pyridine, sodium ethoxide, potassium tert-butoxide, sodium hydride, lithium hexamethyldisilazide, sodium hexamethyldisilazide, n-butyllithium, and the like.

In each step, when performing an aromatic electrophilic substitution reaction, an electrophilic agent (such as, e.g., a halogenating agent, a nitrating agent, or the like) may be used as a reagent. Non-limiting examples of halogenating agents include N-iodosuccinimide, N-bromosuccinimide (NBS), N-chlorosuccinimide (NCS), bromine, bis(tetrafluoroborate)1-(chloromethyl)-4-fluoro-1,4-diazoniabicyclo[2.2.2]octane (SelectFluor®), and the like. Furthermore, non-limiting examples of nitrating agents include nitric acid and the like.

In each step, when performing a Leimgruber-Batcho indole synthesis reaction, a carbon chain homologation agent (such as, e.g., N,N-dimethylformamide dimethyl acetal or the like) and a reducing agent (such as, e.g., a hydrogen atmosphere, catalytic amounts of iron (II) acetate, and rhodium-carbon, or the like) may be used as reagents.

In each step, when performing a deoxyfluorination reaction, non-limiting examples of fluorinating agents include bis(2-methoxyethyl)aminosulfur trifluoride, diethylaminosulfur trifluoride, 4-tert-butyl-2,6-dim ethyl phenyl sulfur trifluoride, N,N-diethyl-S,S-difluorophenyl sulfyliminium tetrafluoroborate, difluoro-4-morpholinyl sulfonium tetrafluoroborate, and the like.

In each step, when performing a decarboxylative fluorination reaction, bis(tetrafluoroborate)1-(chloromethyl)-4-fluoro-1,4-diazoniabicyclo[2.2.2] octane (SelectFluor®) and an inorganic base (for example, lithium carbonate, lithium acetate, potassium fluoride, or the like) may be used.

A compound of formula (I), or a salt thereof, can be synthesized according to a method exemplified in production methods A to H described below or by methods corresponding thereto.

Unless specifically described otherwise, symbols in each general formula in the reaction equations each have the same meaning as above. In the formulae, $R^a$ is chosen from optionally substituted $C_{1-3}$ alkyl groups. Examples of optionally substituted $C_{1-3}$ alkyl groups include $C_{1-3}$ alkyl groups optionally substituted with one to three substituents chosen from the above-mentioned substituent group A. In some embodiments, $R^a$ is chosen from unsubstituted Ci-3 alkyl groups (such as, e.g., a methyl group). In the formulae, X is chosen from halogens (such as, e.g., fluorine, chlorine, bromine, or iodine). $P^1$ is chosen from protecting groups (such as, e.g., tert-butyldimethylsilyl ether) of an alcoholic hydroxyl group. $P^2$ is chosen from protecting groups (such as, e.g., benzyl ether) of a phenolic hydroxyl group.

Raw material compounds used in each production method are either commercially available or can be produced by methods known to those of ordinary skill in the art.

A compound of formula (Ia), or a salt thereof, wherein Z is chosen from $CH_2$, $CF_2$, and O in a compound of formula (I), can be produced from compound (2) by the following method.

[Production Method A]

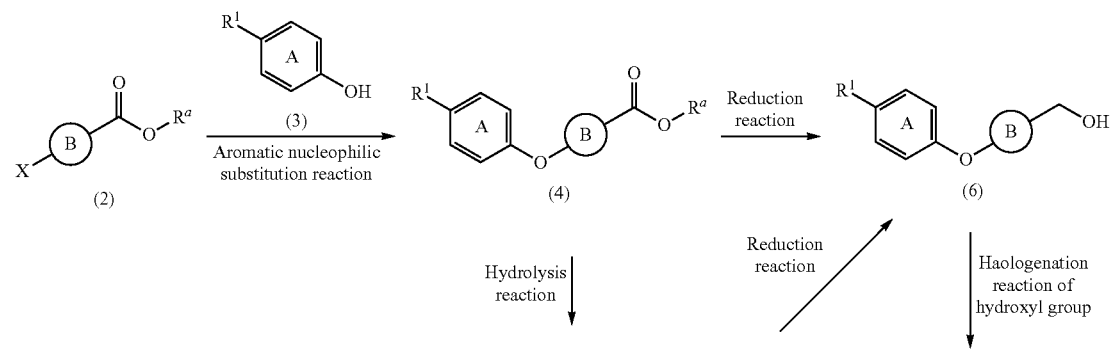

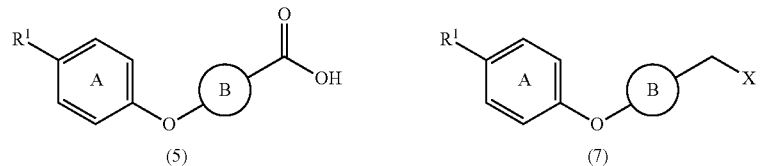

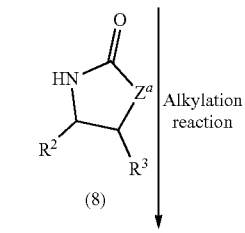

In the formula, $Z^a$ is chosen from $CH_2$, $CF_2$, and O, and all other symbols have the same meaning as above.

Compound (4) can be produced by subjecting compound (2) to an aromatic nucleophilic substitution reaction together with compound (3). Potassium carbonate or the like can be used as the base. Compound (6) can be produced by subjecting compound (4) to a reduction reaction. Furthermore, compound (6) can be produced by subjecting compound (5) obtained by hydrolyzing compound (4) to a reduction reaction. Compound (7) can be produced by halogenating a hydroxyl group of compound (6). Examples of reagents include phosphorus tribromide and the like. A compound of formula (Ia) can be produced by subjecting compound (7) to an alkylation reaction together with compound (8).

A compound of formula (Ib), or a salt thereof, wherein $Z^a$ is $CH_2$ and $R^3$ is a hydroxyl group in a compound of formula (Ia), can be produced from compound (7) by the following method.

[Production Method B]

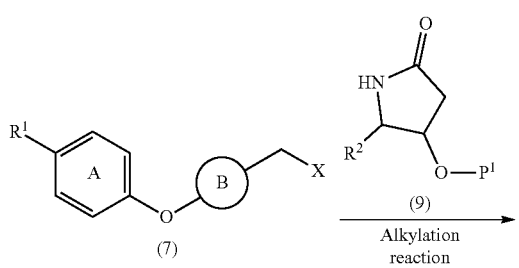

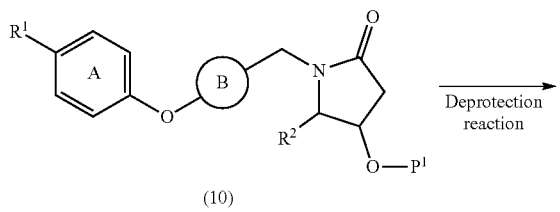

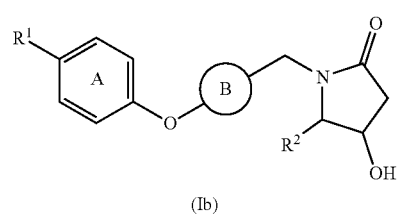

A compound of formula (Ib) can also be produced by deprotecting compound (10) obtained by subjecting compound (7) to an alkylation reaction together with compound (9).

A compound of formula (Ic), or a salt thereof, wherein $R^1$ is a difluoromethyl group in compound of formula (Ia), can also be produced from compound (2) by the following method.

[Production Method C]

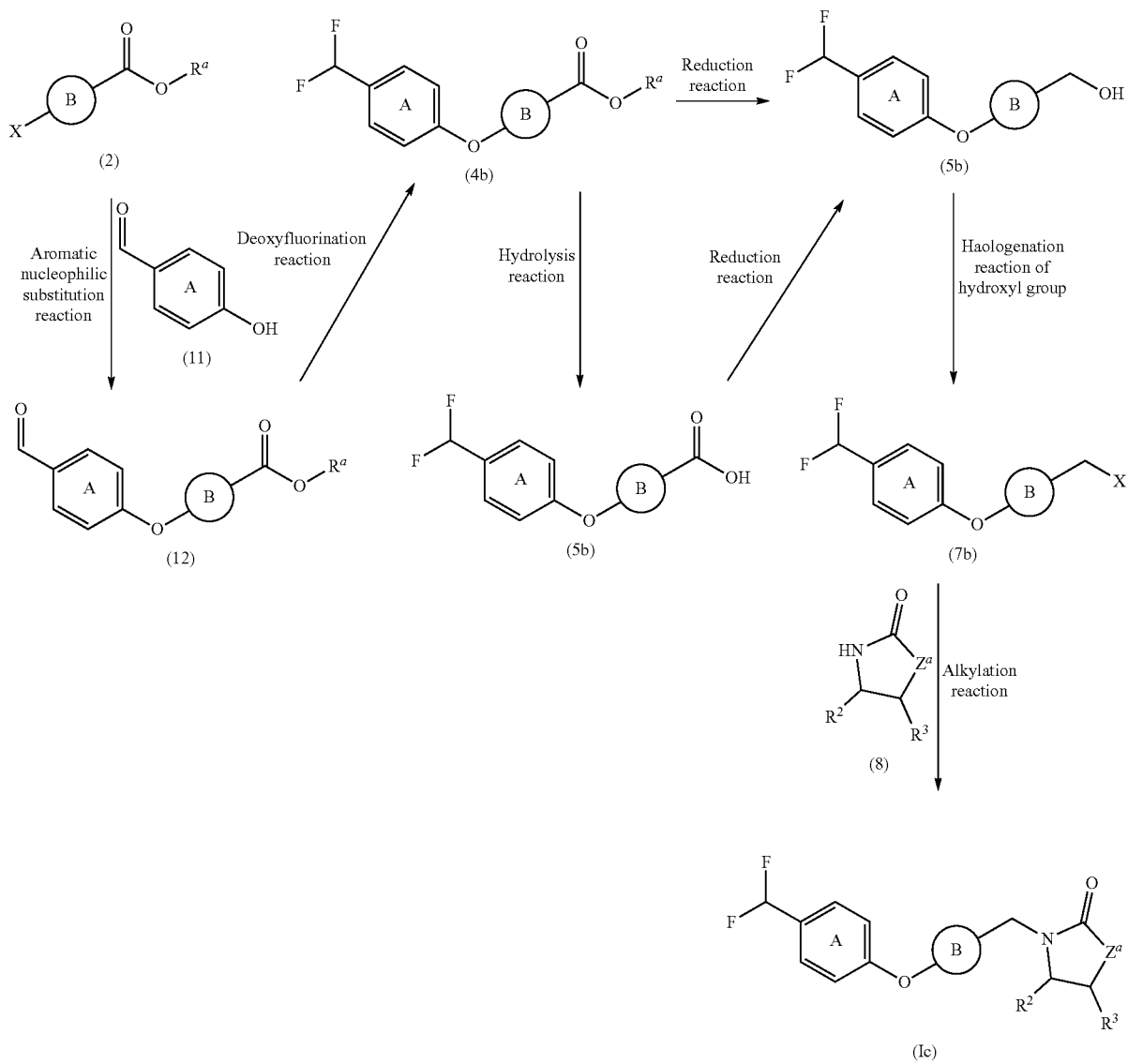

Compound (12) can be produced by subjecting compound (2) to an aromatic nucleophilic substitution reaction together with compound (11). Compound (4b) can be produced by subjecting compound (12) to a deoxidation fluorination reaction. Compound (6b) can be produced by subjecting compound (4b) to a reduction reaction. Furthermore, compound (6b) can be produced by subjecting compound (5b) obtained by hydrolyzing compound (4b) to a reduction reaction. Compound (7b) can be produced by halogenating a hydroxyl group of compound (6b). A compound of formula (Ic) can be produced by subjecting compound (7b) to an alkylation reaction together with compound (8).

A compound of compound (Id), or a salt thereof, wherein $Z^a$ is $CH_2$ and $R^3$ is a hydroxyl group in compound of formula (Ic), can also be produced from compound (7b) by the following method.

[Production Method D]

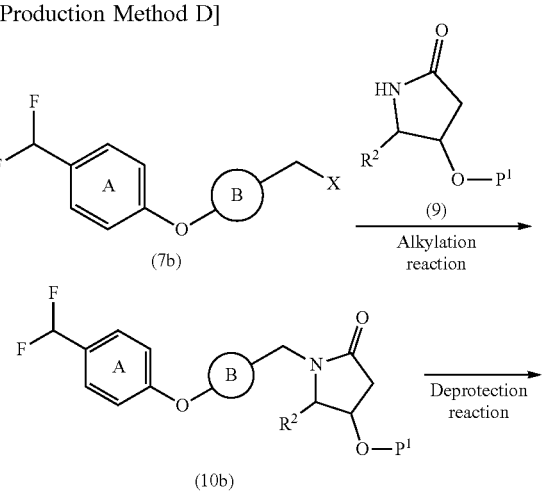

-continued

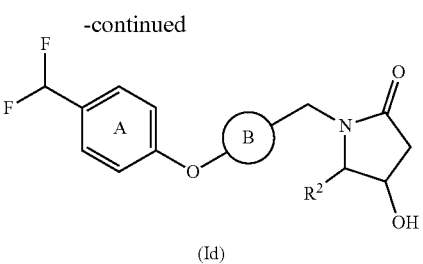

(Id)

A compound of formula (Id) can be produced by deprotecting compound (10b) obtained by subjecting compound (7b) to an alkylation reaction together with compound (9).

A compound of formula (Ie), or a salt thereof, wherein $Z^a$ is O and $R^2$ is a monofluoromethyl group or a difluoromethyl group in a compound of formula (Ia), can also be produced from compound (7) by the following method.

[Production Method E]

In the formula, $R^{2a}$ is a monofluoromethyl group or a difluoromethyl group, and all other symbols have the same meaning as above.

Compound (14) can be produced by subjecting compound (7) to an alkylation reaction together with compound (13). Compound (15) can be produced by subjecting compound (14) to a cyclization reaction in the presence of a base. Non-limiting examples of cyclization agents include triphosgene and the like, and examples of bases include triethylamine and the like. Compound (Ie) can be produced by subjecting compound (15) to a deoxidation fluorination reaction. Furthermore, a compound of formula (Ie) can be produced by subjecting compound (16) obtained by hydrolyzing compound (15) to a deoxidation fluorination reaction.

A compound of formula (If), or a salt thereof, wherein Z is NH and $R^3$ is hydrogen in a compound of formula (I), can also be produced from compound (7) by the following method.

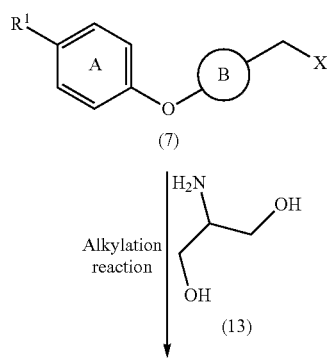

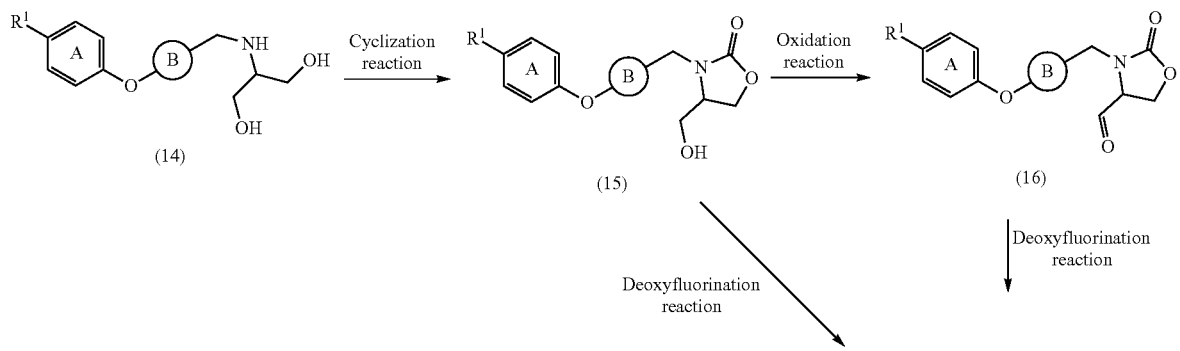

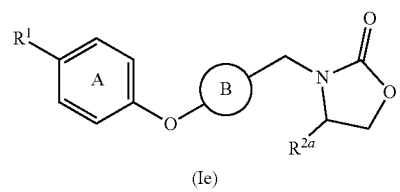

[Production Method F]

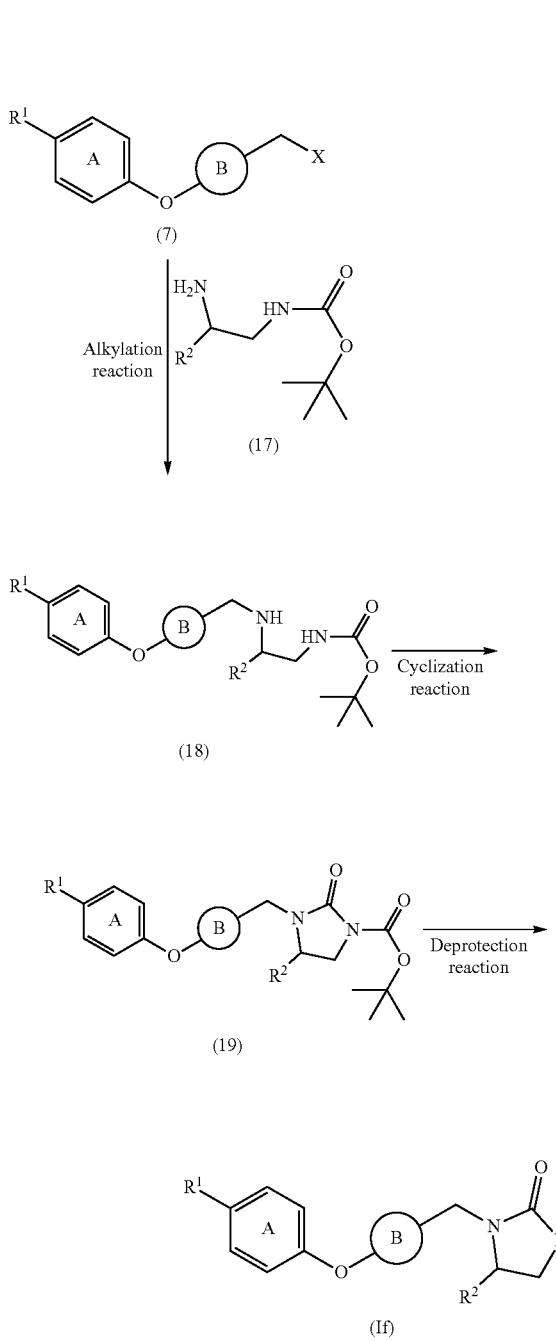

[Production Method G]

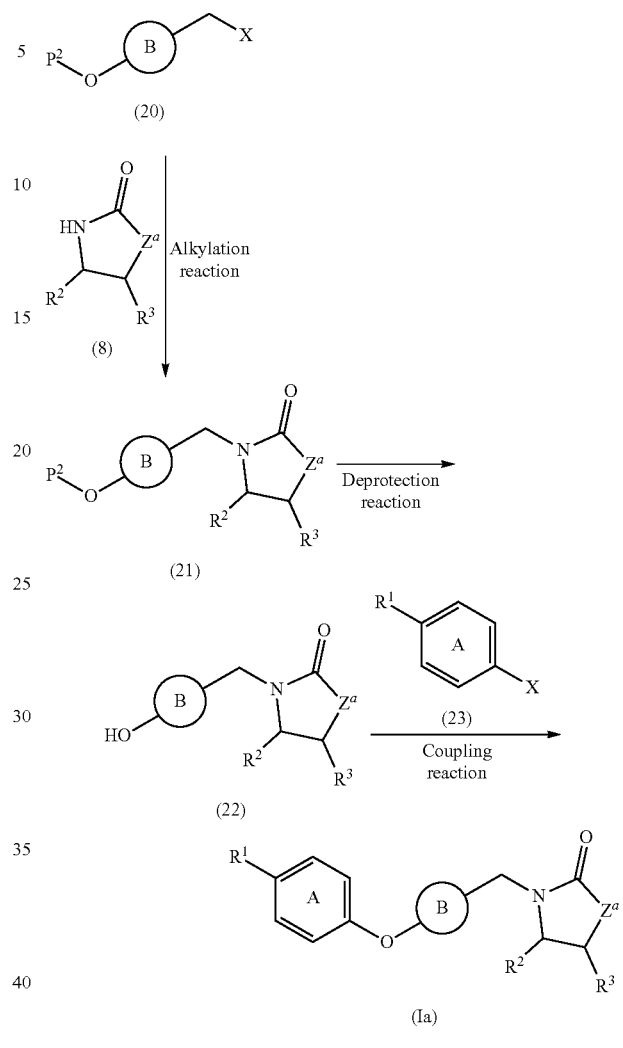

Compound (21) can be produced by subjecting compound (20) to an alkylation reaction together with compound (8). Compound (22) can be obtained by deprotecting compound (21). A compound of formula (Ia) can be produced by coupling compound (22) with compound (23).

A compound of formula (Ib), or a salt thereof, wherein $Z^a$ is $CH_2$ and $R^3$ is a hydroxyl group in a compound of formula (Ia), can also be produced from compound (20) by the following method.

[Production Method H]

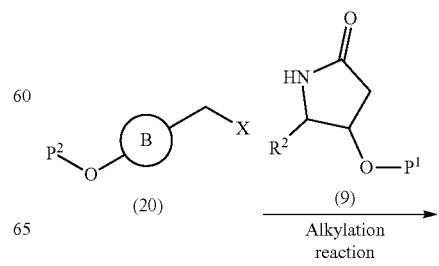

Compound (18) can be produced by subjecting compound (7) to an alkylation reaction together with compound (17). Compound (19) can be produced by subjecting compound (18) to a cyclization reaction in the presence of a base. Examples of cyclization agents include triphosgene and the like, and examples of bases include triethylamine and the like. A compound of formula (If) can be produced by deprotecting compound (19).

A compound of formula (Ia), or a salt thereof, wherein Z is $CH_2$, $CF_2$, or O in a compound of formula (I), can also be produced from compound (20) by the following method.

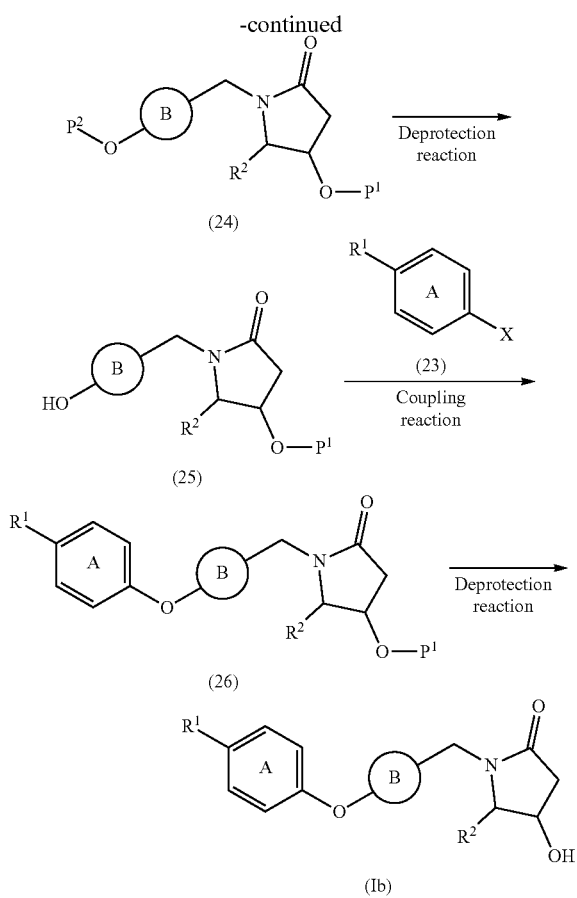

Compound (24) can be produced by subjecting compound (20) to an alkylation reaction together with compound (9). Compound (25) can be produced by deprotecting the $P^2$ group of compound (24). A compound of formula (Ib) can be produced by deprotecting the $P^1$ group of compound (26) obtained by coupling compound (25) with compound (23).

The intramolecular functional group in a compound of formula (I) can also be converted to a target functional group by combining chemical reactions known by those of ordinary skill in the art. Here, non-limiting examples of chemical reactions include oxidation reactions, reduction reactions, alkylation reactions, acylation reactions, urea addition reactions, hydrolysis reactions, amination reactions, esterification reactions, aryl coupling reactions, deprotecting reactions, and the like.

A compound of formula (I) obtained by a production method above can be isolated and purified by known procedures, such as, e.g., solvent extraction, pH conversion of solution, phase transfer, crystallization, recrystallization, and chromatography.

When a compound of formula (I) includes an optical isomer, stereoisomer, regioisomer, or rotamer, these are encompassed in compounds of formula (I) and each can be obtained individually by synthesis methods and separation methods known to those of ordinary skill in the art. For example, when a compound of formula (I) has an optical isomer, an optical isomer resolved from this compound is also encompassed in compounds of formula (I).

Optical isomers can be produced by methods known to those of ordinary skill in the art.

A compound of formula (I) may be in the form a crystal. Crystals of compounds of formula (I) (hereinafter sometimes referred to as crystals of the present disclosure) may be produced by crystallization by applying a crystallization method known to those of ordinary skill in the art to a compound of formula (I).

Crystals of the present disclosure may have superior physiochemical properties (such as, e.g., melting point, solubility, and stability) and biological properties (such as, e.g., pharmacokinetics (absorption, distribution, metabolism, and excretion) and efficacy) and are expected to be useful as a medicament.

EXAMPLES

The present disclosure is explained in further detail using the following by referring Examples, Experimental Examples, and Formulation Examples. These examples do not limit the present disclosure in any way and may be changed so long as they do not deviate from the scope of the present disclosure.

"Room temperature" in the following Examples generally means about 10° C. to about 35° C. The ratios indicated for mixed solvents are volumetric ratios unless otherwise specified. % means the wt. % unless specifically noted otherwise.

Elution in column chromatography in the Examples was performed under observation using TLC (thin layer chromatography). For TLC observation, 60 $F_{254}$ manufactured by Merck was used as a TLC plate, and the solvent used as an elution solvent in column chromatography was also used as a developing solvent. For detection, a UV detector was employed. In silica gel column chromatography, the recitation of NH refers to use of an aminopropylsilane-bound silica gel, and the recitation of diol refers to use of 3-(2,3-dihydroxypropoxy)propylsilane-bound silica gel. In preparative HPLC (high-performance liquid chromatography), the recitation of C18 refers to use of octadecyl-bounded silica gel. The ratio shown for elution solvents indicates a capacity ratio unless otherwise specified.

ACD/SpecManager (trade name) software or the like was used in $^1$H NMR analysis. Extremely gradual proton peaks such as those of hydroxyl groups or amino groups are sometimes not described.

MS was measured by LC/MS. An ESI method or APCI method was used as an ionization method. Data indicate measured values (found). Generally, molecular ion peaks are observed but sometimes they may be observed as fragment ions. In the case of salts, a molecular ion peak or a fragment ion peak of a free form is generally observed.

The unit of sample concentration (c) for optical rotation ($[α]_D$) is g/100 mL.

The elemental analysis value (anal.) is indicated as a calculated value (calcd) and a measured value (found).

The peaks in the powder x-ray diffraction of the Examples mean peaks measured at room temperature using an Ultima IV (Rigaku Corporation, Japan) using the Cu Kα radiation as a radiation source.

The measurement conditions are as follows.
Electric pressure/Electric current: 40 kV/50 mA
Scan speed: 6 degrees/min
Scan range of 2 theta: 2 to 35 degrees The crystallinity by the powder x-ray diffraction of the Examples was calculated by the Hermans method.

The abbreviations below are used in the following Examples.
mp: melting point
MS: mass spectrum
M: molar concentration N: normality
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
IPE: diisopropylether
DMF: N,N-dimethylformamide
THF: tetrahydrofuran
MeOH: methanol
MeCN: acetonitrile
NMP: N-methylpyrrolidone Example 13

(4S,5S)-4-hydroxy-5-methyl-1-{[6-(4-methylphenoxy)pyridine-3-yl]methyl}pyrrolidine-2-one A) Methyl 6-(p-tolyloxy)nicotinate Potassium carbonate (8.55 g) was added at room temperature to a suspension of methyl 6-fluoronicotinate (8.00 g) and p-cresol (5.96 mL) in DMF (80 mL), and the mixture was stirred for three hours at 80° C. After diluting with water, the resulting precipitate was filtered and washed with water to give the title compound (12.5 g).
MS: [M+H]$^+$ 244.1.

B) (6-(p-tolyloxy)pyridine-3-yl)methanol

Sodium borohydride (6.61 g) was added at room temperature to a suspension of methyl 6-(p-tolyloxy)nicotinate (11.5 g) in THF (100 mL)/MeOH (20 mL) and stirred overnight. Then, the mixture was stirred for three hours at 60° C. After diluting with an aqueous ammonium chloride solution and ethyl acetate, the mixture was extracted with ethyl acetate. The organic layer was washed with saturated saline solution, then dried over sodium sulfate and concentrated under reduced pressure. The residue was powderized using hexane to give the title compound (9.46 g).
MS: [M+H]$^+$ 216.1.

C) 5-(bromomethyl)-2-(p-tolyloxy)pyridine

Phosphorus tribromide (0.389 mL) was added at 0° C. to a mixture of (6-(p-tolyloxy)pyridine-3-yl)methanol (740 mg) and THF (10 mL) and stirred for three hours at room temperature.
After diluting with ethyl acetate and water, the mixture was extracted with ethyl acetate. After washing with an aqueous sodium hydrogen carbonate solution and saturated saline solution, the organic layer was dried over sodium sulfate and concentrated under reduced pressure. The residue was powderized using hexane/ethyl acetate to give the title compound (842 mg).
MS: [M+H]$^+$ 278.0.

D) (4S,5S)-4-hydroxy-5-methyl-1-{[6-(4-methylphenoxy)pyridine-3-yl]methyl}pyrrolidine one 0.5 M potassium hexamethyldisilazide toluene solution (19.2 mL) was added at 0° C. to a mixture of (4S,5S)-4-((tert-butyldimethylsilyl)oxy)-5-methylpyrrolidine-2-one (2.00 g), 5-(bromomethyl)-2-(p-tolyloxy)pyridine (3.64 g), and THF (20 mL), and stirred overnight at room temperature.

After diluting with ethyl acetate and water, the mixture was extracted with ethyl acetate. The organic layer was washed with saturated saline solution, then it was dried over sodium sulfate and concentrated under reduced pressure. The residue was purified by silica gel column chromatography (NH, ethyl acetate/hexane) to obtain (4S,5S)-4-((tert-butyldimethylsilyl)oxy)-5-methyl-1-((6-(p-tolyloxy)pyridine-3-yl)methyl)pyrrolidine-2-one (2.13 g). This was dissolved in THF (10 mL), then 4M hydrogen chloride cyclopentyl methyl ether solution (20 mL) was added at room temperature, and the mixture was stirred for three hours at 60° C.
After diluting with ethyl acetate and aqueous saturated sodium bicarbonate solution, the mixture was extracted with ethyl acetate. The organic layer was washed with saturated saline solution, then dried over sodium sulfate and concentrated under reduced pressure. The residue was purified by silica gel column chromatography (NH, ethyl acetate/hexane, and ethyl acetate/methanol) and powderized using hexane/ethyl acetate to give the title compound (1.24 g).
$^1$H NMR (300 MHz, DMSO-d$_6$) δ 1.05 (3H, d, J=6.8 Hz), 2.15 (1H, dd, J=16.6, 3.4 Hz), 2.31 (3H, s), 2.52-2.61 (1H, m), 3.43-3.55 (1H, m), 4.07 (1H, d, J=15.4 Hz), 4.11-4.21 (1H, m), 4.59 (1H, d, J=15.4 Hz), 5.06 (1H, d, J=4.9 Hz), 6.90-7.02 (3H, m), 7.20 (2H, d, J=7.9 Hz), 7.66 (1H, dd, J=8.5, 2.4 Hz), 8.01 (1H, d, J=1.9 Hz).

Example 17

(4 S, 5S)-1-({6-[4-(difluoromethyl)-2-fluorophenoxy]pyridin-3-yl}methyl)-4-hydroxy-5-methylpyrrolidine-2-one After adding 2 M hydrogen chloride-ethanol solution (240 mL) dropwise to an ethanol (100 mL) solution of the (4S,5S)-4-((tert-butyldimethylsilyl)oxy)-1-((6-(4-(difluoromethyl)-2-fluorophenoxy)pyridin-3-yl)methyl)-5-methylpyrrolidine-2-one (140 g) obtained by steps A) to E) in example 38 at 0° C., 5% hydrogen chloride-methanol solution (218 mL) was added, the resultant mixture was slowly returned to room temperature and stirred overnight (using grained silica gel tube). The mixture was concentrated, ethyl acetate (500 mL) was then added to the residue and cooled to 0° C., then aqueous sodium carbonate solution (500 mL) was slowly added, and the organic layer and the aqueous layer were isolated. The aqueous layer was washed with ethyl acetate (1000 mL), and the organic layer was isolated. The obtained organic layers were combined, dried over sodium sulfate, and concentrated under reduced pressure. After dissolving the residue in ethyl acetate (500 mL), it was then filtered through NH silica gel pad (eluted with ethyl acetate (2000 mL)) and concentrated under reduced pressure. Toluene/ethyl acetate (1:0.5) was added to the residue and heated to 50° C. while stirring, then filtered to obtain a crude product (90.5 g). After further concentrating the filtrate, the residue was purified by silica gel column chromatography (ethyl acetate/hexane) to obtain the title compound (6.37 g).
All steps to this point were repeated 7 times to finally obtain 525 g of the title compound.
Ethyl acetate (1630 mL) was added to the title compound (523 g) thus obtained, heated to 50° C., and stirred until dissolved. The solution was filtered and cooled to room temperature, then heptane (2120 mL) was added dropwise while stirring. After stirring the mixture for 1 hour, heptane (4230 mL) was added dropwise. Heptane (4230 mL) was added dropwise to the mixture, and the mixture was further stirred overnight. The precipitate was collected by filtration and washed with heptane, then dried under reduced pressure at 50° C. to obtain the title compound (500 g) as crystals.

$^1$H NMR (300 MHz, DMSO-$d_6$) δ 1.04 (3H, d, J=6.6 Hz) 2.15 (1H, dd, J=16.7, 3.3 Hz) 2.52-2.60 (1H, m) 3.45-3.54 (1H, m) 4.07-4.19 (2H, m) 4.59 (1H, d, J=15.5 Hz) 5.07 (1H, d, J=4.5 Hz) 6.86-7.27 (2H, m) 7.47 (2H, d, J=4.1 Hz) 7.61 (1H, d, J=11.3 Hz) 7.74 (1H, dd, J=8.5, 2.5 Hz) 7.99 (1H, d, J=1.9 Hz).

X-ray powder diffraction patterns were generated using a Rigaku Ultima IV (Rigaku, Tokyo, Japan) with Copper K-alpha radiation.

The obtained crystal was characterized by having specific peaks at the two thetas of 8.5°±0.2°, 11.2°±0.2°, 13.5°±0.2°, 14.6°±0.2°, 14.9°±0.2°, 19.8°±0.2°, 21.5°±0.2° and 22.5°±0.2° degrees in a powder X-ray diffraction pattern.

Example 37

(4S,5S)-1-{[6-(2,4-difluorophenoxy)pyridine-3-yl]methyl}-4-hydroxy-5-methylpyrrolidine-2-one A) Methyl 6-(2,4-difluorophenoxy)nicotinate A mixture of methyl 6-fluoronicotinate (4.31 g), 2,4-difluorophenol (3.80 g), potassium carbonate (5.76 g), and MeCN (30 mL) was stirred for 16 hours at 60° C. The mixture was diluted with ethyl acetate and water, and it was extracted with ethyl acetate. The organic layer was washed with 10% aqueous potassium carbonate solution and saturated saline solution, dried over sodium sulfate, passed through an NH silica gel pad, and concentrated under reduced pressure to give the title compound (7.37 g).

MS: [M+H]$^+$ 266.3.

B) Methyl (6-(2,4-difluorophenoxy)pyridine-3-yl)methanol

Sodium borohydride (4.21 g) was added at room temperature to a suspension of methyl 6-(2,4-difluorophenoxy)nicotinate (7.37 g) in THF (60 mL)/MeOH (15 mL), and the mixture was stirred for three hours at 60° C.

Then added sodium borohydride (4.21 g) at room temperature, and the mixture was stirred for an additional three hours at 60° C. The solvent was distilled off, and the mixture was diluted with water and extracted with ethyl acetate. The organic layer was washed with saturated saline solution, dried over sodium sulfate, passed through an NH silica gel pad, and concentrated under reduced pressure to give the title compound (6.59 g).

MS: [M+H]$^+$ 238.3.

C) 5-(bromomethyl)-2-(2,4-difluorophenoxy)pyridine

Phosphorus tribromide (2.90 mL) was added at 0° C. to a mixture of (6-(2,4-difluorophenoxy)pyridine-3-yl)methanol (6.59 g) and THF (70 mL) and stirred for 16 hours at room temperature.

The mixture was diluted with ethyl acetate, and the solution was washed with aqueous sodium hydrogen carbonate solution and saturated saline solution, and dried over sodium sulfate. The residue was purified by silica gel column chromatography (ethyl acetate/hexane) to give the title compound (7.07 g).

$^1$H NMR (300 MHz, DMSO-$d_6$) δ 4.72 (2H, s), 7.10-7.20 (2H, m), 7.36-7.50 (2H, m), 7.96 (1H, dd, J=8.5, 2.4 Hz), 8.18 (1H, d, J=2.3 Hz).

D) (4S,5S)-4-((tert-butyldimethylsilyl)oxy)-1-((6-(2,4-difluorophenoxy)pyridin-3-yl)methyl)-5-methylpyrrolidine-2-one 1.6 M butyllithium hexane solution (6.16 mL) was added at −78° C. to a mixture of (4S,5S)-4-((tert-butyldimethylsilyl)oxy)-5-methylpyrrolidine-2-one (2.26 g) and THF (40 mL) and stirred for 30 minutes at 0° C. 5-(bromomethyl)-2-(2,4-difluorophenoxy)pyridine (2.96 g) was added to the mixture and stirred for 1 hour at room temperature then stirred for an additional 7.5 hours at 50° C. After diluting with ethyl acetate and water, the mixture was extracted with ethyl acetate. The organic layer was washed with saturated saline solution, dried over sodium sulfate, passed through an NH silica gel pad, and concentrated under reduced pressure. The residue was purified by silica gel chromatography (ethyl acetate/hexane) to give the title compound (2.30 g).

MS: [M+H]$^+$ 449.2.

E) (4S,5S)-1-{(6-(2,4-difluorophenoxy)pyridine-3-yl]methyl}-4-hydroxy-5-methylpyrrolidine one A mixture of (4S,5S)-4-((tert-butyldimethyl silyl)oxy)-1-((6-(2,4-difluorophenoxy)pyridine-3-yl)methyl)-5-methylpyrrolidine-2-one (2.29 g) and 2M hydrogen chloride-ethanol solution (40 mL) were stirred for one hour at room temperature.

The mixture was concentrated, then the residue was diluted with aqueous sodium hydrogen carbonate solution, then extracted with ethyl acetate. The organic layer was washed with saturated saline solution, then dried over sodium sulfate and concentrated under reduced pressure. The residue was purified by silica gel column chromatography (ethyl acetate/hexane and ethyl acetate/methanol) to give a crude product. This was dissolved in ethyl acetate at 80° C., heptane was added dropwise to the solution, and the resulting suspension was stirred for 18 hours at room temperature.

The precipitate was collected by filtration and dried under reduced pressure at 60° C. to give the title compound (1.47 g).

$^1$H NMR (300 MHz, DMSO-$d_6$) δ 1.04 (3H, d, J=6.8 Hz), 2.14 (1H, dd, J=16.6, 3.0 Hz), 2.52-2.63 (1H, m), 3.44-3.54 (1H, m), 4.04-4.21 (2H, m), 4.59 (1H, d, J=15.4 Hz), 5.05 (1H, d, J=4.9 Hz), 7.06-7.19 (2H, m), 7.32-7.48 (2H, m), 7.71 (1H, dd, J=8.5, 2.4 Hz), 7.97 (1H, d, J=1.9 Hz).

Example 38

(4 S, 5S)-1-({6-[4-(difluoromethyl)-2-fluorophenoxy]pyridine-3-yl}methyl)-4-hydroxy-5-methylpyrrolidine-2-one A) Methyl 6-(2-fluoro-4-formylphenoxy)nicotinate A mixture of methyl 6-fluoronicotinate (12.2 g), 3-fluoro-4-hydroxybenzaldehyde (11.0 g), potassium carbonate (16.3 g), and NMP (75 mL) was stirred for 16 hours at 90° C. in a nitrogen atmosphere.

The mixture was diluted with ethyl acetate and water, and it was extracted with ethyl acetate. The organic layer was washed with 10% aqueous potassium carbonate solution and saturated saline solution, dried over sodium sulfate, and concentrated under reduced pressure. The residue was purified by silica gel column chromatography (ethyl acetate/hexane) and crystallized from hexane to give the title compound (17.4 g).
MS: [M+H]$^+$ 276.0.

B) Methyl 6-(4-(difluoromethyl)-2-fluorophenoxy)nicotinate (Diethylamino)sulfur trifluoride (11.5 mL) was added to a solution of methyl 6-(2-fluoro-4-formylphenoxy)nicotinate (8.00 g) in toluene (90 mL) at 0° C., and the mixture was stirred for one day at room temperature. After adding MeOH (10 mL) to stop the reaction, the mixture was diluted with 10% potassium carbonate aqueous solution and extracted with ethyl acetate. The organic layer was washed with saturated saline solution, dried over sodium sulfate, passed through an NH silica gel pad, and concentrated under reduced pressure. The residue was purified by silica gel column chromatography (ethyl acetate/hexane) to give the title compound (8.14 g).
MS: [M+H]$^+$ 298.0.

C) (6-(4-(difluoromethyl)-2-fluorophenoxy)pyridine-3-yl)methanol

Sodium borohydride (4.14 g) was added to a THF (60 mL)/MeOH (15 mL) suspension of methyl 6-(4-(difluoromethyl)-2-fluorophenoxy)nicotinate (8.14 g) at room temperature, and the mixture was stirred for 1 hour at 60° C. Sodium borohydride (4.14 g) was added at room temperature, and the mixture was stirred for an additional hour at 60° C. The mixture was diluted with water, and it was extracted with ethyl acetate. The organic layer was washed with saturated saline solution, dried over sodium sulfate, and concentrated under reduced pressure. The residue was purified by silica gel column chromatography (ethyl acetate/hexane) to give the title compound (5.33 g).
MS: [M+H]$^+$ 270.0.

D) 5-(bromomethyl)-2-(4-(difluoromethyl)-2-fluorophenoxy)pyridine

Phosphorus tribromide (0.357 mL) was added to a mixture of (6-(4-difluoromethyl)-2-fluorophenoxy)pyridine-3-yl)methanol (920 mg) and THF (10 mL) at 0° C., and this was stirred for 16 hours at room temperature. After diluting the mixture with ethyl acetate, the solution was washed with sodium hydrogen carbonate aqueous solution and a saturated saline solution and dried over sodium sulfate. The residue was purified by silica gel column chromatography (ethyl acetate/hexane) to give the title compound (977 mg).
MS: [M+H]$^+$ 332.0.

E) (4S,5S)-4-((tert-butyldimethylsilyl)oxy)-1-((6-(4-(difluoromethyl)-2-fluorophenoxy)pyridine-3-yl)methyl)-5-methylpyrrolidine-2-one 1.6 M butyllithium-hexane solution (4.50 mL) was added dropwise to a mixture of (4S,5S)-4-((tert-butyldimethylsilyl)oxy)-5-methylpyrrolidine-2-one (1.65 g) and THF (24 mL) at −78° C., and this was stirred for 30 minutes at 0° C. 5-(bromomethyl)-2-(4-(difluoromethyl) fluorophenoxy) pyridine (2.39 g) was added to the mixture, and this was stirred for 20 minutes at room temperature. Afterward, this was stirred for 22 hours at 50° C. and stirred for 48 hours at 40° C. The mixture was diluted with ethyl acetate and water and afterward it was extracted with ethyl acetate. The organic layer was washed with saturated saline solution, then dried over sodium sulfate, filtered, and concentrated under reduced pressure. The residue was purified by silica gel column chromatography (ethyl acetate/hexane), to give the title compound (2.15 g).
MS: [M+H]$^+$ 481.2.

F) (4S,5S)-1-({6-[4-(difluoromethyl)-2-fluorophenoxy]pyridine-3-yl}methyl)-4-hydroxy-5-methylpyrrolidine-2-one A mixture of (4S,5S)-4-((tert-butyldimethylsilyl)oxy)-1-((6-(4-(difluoromethyl)-2-fluorophenoxy)pyridine-3-yl)methyl)-5-methylpyrrolidine-2-one (2.14 g) and 2 M hydrogen chloride-ethanol solution (40 mL) was stirred for 18 hours at room temperature. The mixture was concentrated, then the residue was diluted with sodium hydrogen carbonate aqueous solution. Afterward, this was extracted with ethyl acetate. The organic layer was washed with saturated saline solution. Afterward, this was dried over sodium sulfate, filtered, and concentrated under reduced pressure. The residue was purified by silica gel column chromatography (ethyl acetate/hexane and ethyl acetate/methanol), and a crude product (1.61 g) was obtained. The crude product was dissolved in warm ethyl acetate (5 mL), to the solution was added heptane (8 mL) dropwise at room temperature, and the mixture was stirred for 15 minutes. Heptane (16 mL) was added dropwise to the obtained mixture at room temperature, and the mixture was stirred for an additional 30 minutes. Heptane (16 mL) was added dropwise to the obtained mixture at room temperature, and the mixture was stirred for an additional 72 hours. The precipitate was collected by filtration and dried under reduced pressure to give the title compound (1.52 g) as crystals.
$^1$H NMR (300 MHz, DMSO-d$_6$) δ 1.04 (3H, d, J=6.8 Hz), 2.15 (1H, dd, J=16.6, 3.4 Hz), 2.52-2.61 (1H, m), 3.45-3.55 (1H, m), 4.06-4.21 (2H, m), 4.59 (1H, d, J=15.4 Hz), 5.07 (1H, d, J=4.9 Hz), 7.07 (1H, t, J=57.0 Hz), 7.15 (1H, d, J=8.7 Hz), 7.47 (2H, d, J=4.1 Hz), 7.61 (1H, d, J=10.9 Hz), 7.74 (1H, dd, J=8.5, 2.4 Hz), 7.99 (1H, d, J=1.9 Hz).

X-ray powder diffraction patterns were generated using a Rigaku Ultima IV (Rigaku, Tokyo, Japan) with Copper K-alpha radiation.

The obtained crystal was characterized by having specific peaks at the two thetas of 5.1°±0.2°, 10.3°±0.2°, 14.3°±0.2°, 16.5°±0.2°, 17.6°±0.2°, 22.3°±0.2° and 25.2°±0.2° degrees in a powder X-ray diffraction pattern.

Example 45

(5S)-1-{[2-(2,4-difluorophenoxy)pyrimidine-5-yl]methyl}-5-methylpyrrolidine-2-one

A) methyl 2-(2,4-difluorophenoxy)pyrimidine-5-carboxylate

A mixture of methyl 2-chloropyrimidine-5-carboxylate (5.00 g), 2,4-difluorophenol (2.77 mL), potassium carbonate (6.01 g), and MeCN (60 mL) was stirred for 16 hours at room temperature in a nitrogen atmosphere. The mixture was diluted with ethyl acetate and water, and it was extracted with ethyl acetate. The organic layer was washed with 10% potassium carbonate aqueous solution and saturated saline solution, dried over sodium sulfate, passed through NH silica gel pad, and concentrated under reduced pressure. The residue was crystallized from hexane to give the title compound (7.18 g).

MS: [M+H]$^+$ 267.0.

B) 2-(2,4-difluorophenoxy)pyrimidine-5-carboxylic Acid

2 M sodium hydroxide aqueous solution (20.2 mL) was added to a mixture of methyl 2-(2,4-difluorophenoxy)pyrimidine-5-carboxylate (7.18 g) and THF (80 mL) at room temperature, and the mixture was stirred for 5 hours. The mixture was concentrated under reduced pressure, and this was diluted with water (40 mL) and then neutralized with 1 M hydrochloric acid (40 mL). The obtained precipitate was collected and washed with water to give the title compound (4.98 g).

MS: [M−H]$^+$ 250.9.

C) (2-(2,4-difluorophenoxy)pyrimidine-5-yl)methanol

Isobutyl chloroformate (3.07 mL) and 4-methylmorpholine (3.25 mL) were added to a mixture of 2-(2,4-difluorophenoxy)pyrimidine-5-carboxylic acid (4.97 g) and THF (80 mL) at 0° C., and the mixture was stirred for 1 hour at the same temperature. Sodium borohydride (1.86 g) and water (20 mL) were added dropwise at 0° C., and the mixture was stirred for an additional 16 hours at room temperature. The mixture was diluted with ethyl acetate and water, and it was extracted with ethyl acetate. The organic layer was washed with 10% potassium carbonate aqueous solution and saturated saline solution, dried over sodium sulfate, and concentrated under reduced pressure. The residue was purified by silica gel column chromatography (ethyl acetate/hexane) to give the title compound (2.93 g).

$^1$H NMR (300 MHz, DMSO-d$_6$) δ 4.50 (2H, d, J=5.7 Hz), 5.38 (1H, t, J=5.7 Hz), 7.11-7.21 (1H, m), 7.41-7.53 (2H, m), 8.59 (2H, s).

D) 5-(bromomethyl)-2-(2,4-difluorophenoxy)pyrimidine

Phosphorus tribromide (1.29 mL) was added to a mixture of (2-(2,4-difluorophenoxy)pyrimidine-5-yl)methanol (2.93 g) and THF (30 mL) at 0° C., and this was stirred for 16 hours at room temperature. The mixture was diluted with ethyl acetate, and the solution was washed with sodium hydrogen carbonate aqueous solution and saturated saline solution and dried over sodium sulfate. The residue was purified by silica gel column chromatography (ethyl acetate/hexane) to give the title compound (2.34 g).

MS: [M+H]$^+$ 300.9.

E) (5S)-1-{[2-(2,4-difluorophenoxy)pyrimidine-5-yl]methyl}-5-methylpyrrolidine-2-one 1.6 M butyllithium-hexane solution (2.30 mL) was added dropwise to a mixture of (S)-5-methylpyrrolidine-2-one (0.364 g) and THF (12 mL) at −78° C., and this was stirred for 30 minutes at 0° C. 5-(bromomethyl)-2-(2,4-difluorophenoxy)pyrimidine (1.11 g) was added to the mixture, and this was stirred for 1.5 hours at room temperature. The mixture was diluted with ethyl acetate and ammonium chloride aqueous solution and then it was extracted with ethyl acetate. The organic layer was washed with saturated saline solution, then dried over sodium sulfate, passed through a silica gel/NH silica gel pad, and concentrated under reduced pressure. The residue was purified by silica gel column chromatography (NH, ethyl acetate/hexane) and recrystallized from ethyl acetate/heptane to give the title compound (0.621 g) as crystals.

$^1$H NMR (300 MHz, DMSO-d$_6$) δ 1.13 (3H, d, J=6.4 Hz), 1.44-1.59 (1H, m), 2.06-2.34 (3H, m), 3.52-3.64 (1H, m), 4.17 (1H, d, J=15.8 Hz), 4.56 (1H, d, J=15.4 Hz), 7.11-7.21 (1H, m), 7.41-7.53 (2H, m), 8.55 (2H, s).

X-ray powder diffraction patterns were generated using a Rigaku Ultima IV (Rigaku, Tokyo, Japan) with Copper K-alpha radiation.

The obtained crystal was characterized by having specific peaks at the two thetas of 7.4°±0.2°, 10.3°±0.2°, 10.5°±0.2°, 14.5°±0.2°, 16.4°±0.2°, 17.8°±0.2°, 18.6°±0.2°, 19.5°±0.2°, 20.6°±0.2° and 21.3°±0.2° degrees in a powder X-ray diffraction pattern.

Example 49

(4S)-3-{[2-(4-chloro-2-fluorophenoxy)pyrimidine-5-yl]methyl}-4-methyl-1,3-oxazolidine-2-one

A) Methyl 2-(4-chloro-2-fluorophenoxy)pyrimidine-5-carboxylate

A mixture of methyl 2-chloropyrimidine-5-carboxylate (5.00 g), 4-chloro-2-fluorophenol (3.08 mL), potassium carbonate (6.01 g), and MeCN (60 mL) was stirred for 16 hours under a nitrogen atmosphere at room temperature. The mixture was diluted with ethyl acetate and water, and it was extracted with ethyl acetate. The organic layer was washed with water and saturated saline solution, dried over sodium sulfate, passed through NH silica gel pad, and concentrated under reduced pressure. The residue was crystallized from hexane to give the title compound (7.39 g).

MS: [M+H]$^+$ 283.0.

B) 2-(4-chloro-2-fluorophenoxy)pyrimidine-5-carboxylic Acid

2 M sodium hydroxide aqueous solution (14.4 mL) was added to a mixture of methyl 2-(4-chloro-2-fluorophenoxy)pyrimidine-5-carboxylate (7.39 g) and THF (50 mL) at room temperature, and the mixture was stirred for 16 hours. The reaction mixture was concentrated under reduced pressure, then diluted with water (30 mL) and neutralized with 1 M hydrochloric acid (29 mL). The obtained precipitate was collected by filtration and washed with water to give the title compound (6.35 g).

MS: [M−H]$^+$ 266.8.

C) (2-(4-chloro-2-fluorophenoxy)pyrimidine-5-yl)methanol

Isobutyl chloroformate (3.67 mL) and 4-methylmorpholine (3.89 mL) were added to a mixture of 2-(4-chloro-2-fluorophenoxy)pyrimidine-5-carboxylic acid (6.33 g) and THF (100 mL) at 0° C., and the mixture was stirred for 1 hour at the same temperature. Sodium borohydride (2.23 g) and water (25 mL) were added dropwise at 0° C., and the mixture was stirred for an additional 16 hours at room temperature. The mixture was diluted with ethyl acetate and water, and it was extracted with ethyl acetate. The organic layer was washed with water and saturated saline solution, dried over sodium sulfate, passed through NH silica gel pad, and concentrated under reduced pressure. The residue was purified by silica gel column chromatography (ethyl acetate/hexane), and the generated solid was washed with IPE to give the title compound (2.80 g).

$^1$H NMR (300 MHz, DMSO-$d_6$) δ 4.50 (2H, d, J=5.3 Hz), 5.39 (1H, t, J=5.7 Hz), 7.33-7.40 (1H, m), 7.42-7.51 (1H, m), 7.65 (1H, dd, J=10.5, 2.3 Hz), 8.59 (2H, s).

D) 5-(bromomethyl)-2-(4-chloro-2-fluorophenoxy)pyrimidine

Phosphorous tribromide (1.15 mL) was added to a mixture of (2-(4-chloro-2-fluorophenoxy)pyrimidine-5-yl)methanol (2.80 g) and THF (25 mL) at 0° C., and this was stirred for 16 hours at room temperature. The mixture was diluted with ethyl acetate, and this solution was washed with sodium hydrogen carbonate aqueous solution and dried over sodium sulfate. The residue was purified by silica gel column chromatography (ethyl acetate/hexane) and crystallized from hexane to give the title compound (2.22 g).

MS: [M+H]$^+$ 316.9.

E) (4S)-3-[2-(4-chloro-2-fluorophenoxy)pyrimidine-5-yl]methyl-4-methyl-1,3-oxazolidine-2-one 1.6 M butyllithium-hexane solution (0.637 mL) was added to a mixture of (S) methyloxazolidine-2-one (0.103 g) and THF (8 mL) at −78° C., and this was stirred for 30 minutes at 0° C. 5-(bromomethyl)-2-(4-chloro-2-fluorophenoxy)pyrimidine (0.323 g) was added to the mixture, and this was stirred for 60 hours at room temperature. The mixture was diluted with ethyl acetate and water and afterward it was extracted with ethyl acetate. The organic layer was washed with saturated saline solution, then dried over sodium sulfate and concentrated under reduced pressure. The residue was purified by silica gel column chromatography (NH, ethyl acetate/hexane) and recrystallized from ethyl acetate/heptane to give the title compound (0.233 g) as crystals.

$^1$H NMR (300 MHz, DMSO-$d_6$) δ 1.18 (3H, d, J=6.0 Hz), 3.77-3.87 (2H, m), 4.27 (1H, d, J=15.0 Hz), 4.35-4.50 (2H, m), 7.34-7.41 (1H, m), 7.43-7.51 (1H, m), 7.66 (1H, dd, J=10.4, 2.4 Hz), 8.63 (2H, s).

X-ray powder diffraction patterns were generated using a Rigaku Ultima IV (Rigaku, Tokyo, Japan) with Copper K-alpha radiation.

The obtained crystal was characterized by having specific peaks at the two thetas of 5.4°±0.2°, 14.0°±0.2°, 16.3°±0.2°, 17.4°±0.2°, 18.6°±0.2°, 20.3°±0.2°, 21.0°±0.2°, 21.8°±0.2° and 24.5°±0.2° degrees in a powder X-ray diffraction pattern.

The Example compounds are shown in the following Tables. In the Tables, MS indicates a measured value. The compounds of examples 1 to 12, 14 to 16, 18 to 36, 39 to 44, 46 to 48, and 50 were produced according to the methods given in the above Examples or methods equivalent thereto.

TABLE 1-1

| EXAMPLE | IUPACNAME | Structure | ADDITIVE | MS |
|---|---|---|---|---|
| 1 | 5-methyl-1-{[4-(4-methylphenoxy)phenyl]methyl}pyrrolidin-2-one | 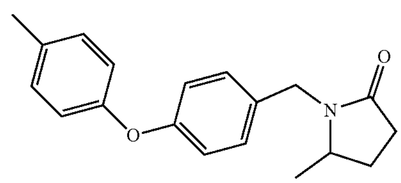 [SMILES: Cc1ccc(Oc2ccc(CN3C(=O)CCC3C)cc2)cc1] | | 296.3 |
| 2 | 5-methyl-1-{[4-(4-methylphenoxy)pheny]methyl}pyrrolidin-2-one (optical isomer) | 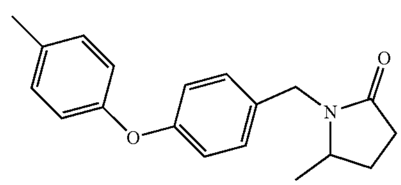 [SMILES: Cc1ccc(Oc2ccc(CN3C(=O)CCC3C)cc2)cc1] | | 296.2 |
| 3 | 5-methyl-1-{[4-(4-methylphenoxy)phenyl]methyl}pyrrolidin-2-one (optical isomer) | 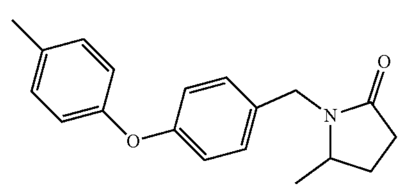 [SMILES: Cc1ccc(Oc2ccc(CN3C(=O)CCC3C)cc2)cc1] | | 296.2 |
| 4 | 5-methyl-1-{[5-(4-methylphenoxy)pyrazin-2-yl]methyl}yrrolidin-2-one | 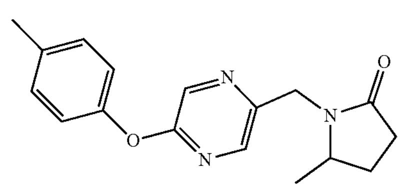 [SMILES: Cc1ccc(Oc2cnc(CN3C(=O)CCC3C)cn2)cc1] | | 298.2 |

TABLE 1-1-continued

| EXAMPLE | IUPACNAME | Structure | ADDITIVE | MS |
|---|---|---|---|---|
| 5 | 5-methyl-1-{[2-(4-methylphenoxy)pyrimidin-5-yl]methyl}pyrrolidin-2-one | 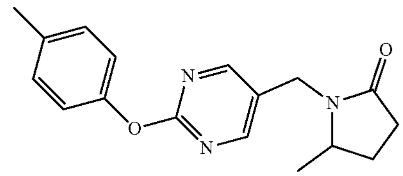 [SMILES: Cc1ccc(Oc2ncc(CN3C(=O)CCC3C)cn2)cc1] | | 298.2 |
| 6 | (4S,5S)-4-hydroxy-5-methyl-1-{[4-(4-methylphenoxy)phenyl]methyl}pyrrolidin-2-one | 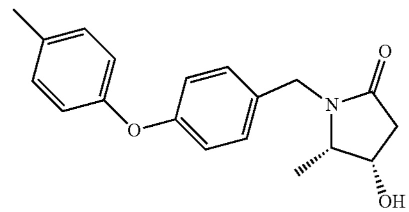 [SMILES: Cc1ccc(Oc2ccc(CN3C(=O)C[C@H](O)[C@@H]3C)cc2)cc1] | | 312.2 |
| 7 | (4S,5S)-5-ethyl-4-hydroxy-1-{[4-(4-methylphenoxy)phenyl]methyl}pyrrolidin-2-one | 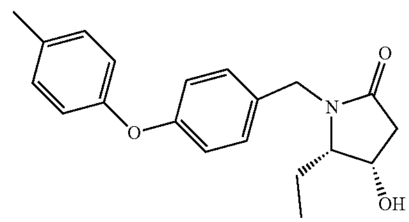 [SMILES: CC[C@H]1[C@@H](O)CC(=O)N1Cc1ccc(Oc2ccc(C)cc2)cc1] | | 326.2 |
| 8 | 5-methyl-1{[5-(4-methylphenoxy)pyrimidin-2-yl]methyl}pyrrolidin-2-one | 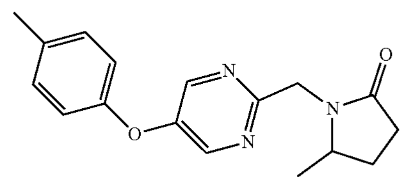 [SMILES: Cc1ccc(Oc2cnc(CN3C(=O)CCC3C)nc2)cc1] | | 298.1 |
| 9 | (4S,5S)-1-{[4-(4-fluorophenoxy)phenyl]methyl}-4-hydroxy-5-methylpyrrolidin-2-one | 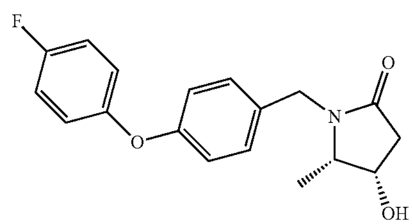 [SMILES: C[C@H]1[C@@H](O)CC(=O)N1Cc1ccc(Oc2ccc(F)cc2)cc1] | | 316.1 |
| 10 | (4R,5S)-4-hydroxy-5-methyl-1-{[4-(4-methylphenoxy)phenyl]methyl}pyrrolidin-2-one | 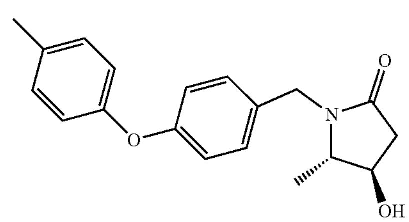 [SMILES: Cc1ccc(Oc2ccc(CN3C(=O)C[C@@H](O)[C@@H]3C)cc2)cc1] | | 312.2 |

TABLE 1-2

| EXAMPLE | IUPACNAME | Structure | ADDITIVE | MS |
|---|---|---|---|---|
| 11 | (4S,5R)-4-hydroxy-5-methyl-1-{[4-(4-methylphenoxy)pheny]methyl}pyrrolidin-2-one | 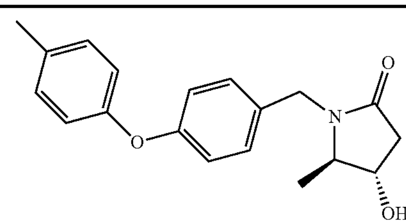 | | 312.2 |

TABLE 1-2-continued

| EXAMPLE | IUPACNAME | Structure | ADDITIVE | MS |
|---|---|---|---|---|
| 12 | (4R,5R)-4-hydroxy-5-methyl-1-{[4-(4-methylphenoxy)phenyl]methyl}pyrrolidin-2-one | 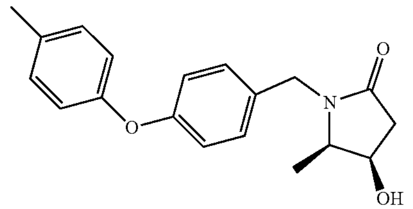 [SMILES: Cc1ccc(Oc2ccc(CN3C(=O)C[C@@H](O)[C@H]3C)cc2)cc1] | | 312.2 |
| 13 | (4S,5S)-4-hydroxy-5-methyl-1-{[6-(4-methylphenoxy)pyridin-3-yl]methyl}pyrrolidin-2-one | 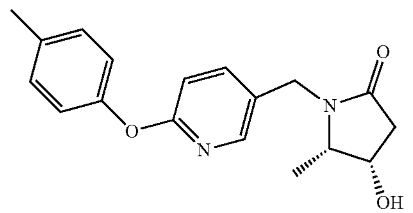 [SMILES: Cc1ccc(Oc2ccc(CN3C(=O)C[C@H](O)[C@@H]3C)cn2)cc1] | | 313.2 |
| 14 | (4S,5S)-4-hydroxy-5-methyl-1-{[6-(4-methylphenoxy)pyridin-3-yl]methyl}pyrrolidin-2-one | 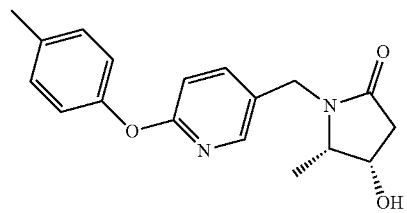 | HCl | 313.2 |
| 15 | (4S,5S)-4-hydroxy-5-methyl-1-{[2-(4-methylphenoxy)pyrimidin-5-yl]methyl}pyrrolidin-2-one | 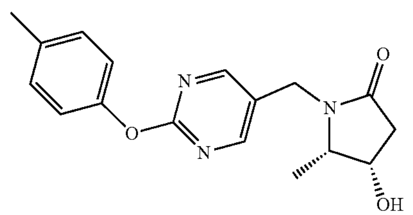 [SMILES: Cc1ccc(Oc2ncc(CN3C(=O)C[C@H](O)[C@@H]3C)cn2)cc1] | | 314.2 |
| 16 | (4S,5S)-4-hydroxy-5-methyl-1-{[5-(4-methylphenoxy)pyridin-2-yl]methyl}pyrrolidin-2-one | 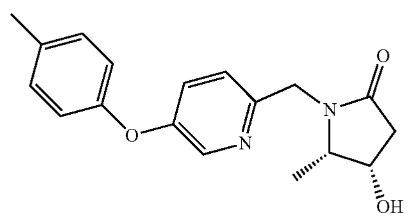 | | 313.2 |
| 17 | (4S,5S)-1-({6-[4-(difluoromethyl)-2-fluorophenoxy]pyridin-3-yl}methyl)-4-hydroxy-5-methylpyrrolidin-2-one | 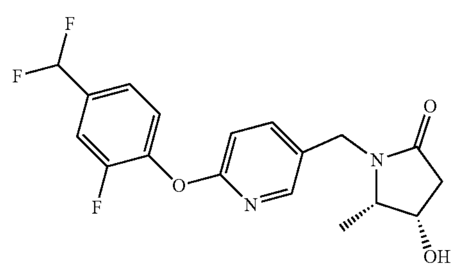 [SMILES: C[C@H]1[C@@H](O)CC(=O)N1Cc1ccc(Oc2ccc(C(F)F)cc2F)nc1] | | 367.1 |
| 18 | (4S)-4-methy-3-{[4-(4-methylphenoxy)phenyl]methyl}1,3-oxazolidin-2-one | 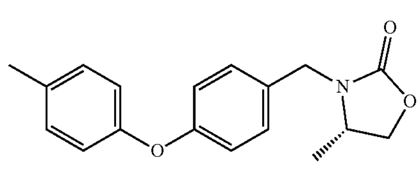 [SMILES: Cc1ccc(Oc2ccc(CN3C(=O)OC[C@@H]3C)cc2)cc1] | | 298.2 |

TABLE 1-2-continued

| EXAMPLE | IUPACNAME | Structure | ADDITIVE | MS |
|---|---|---|---|---|
| 19 | (4S,5S)-4-hydroxy-5-methyl-1-{[5-(4-methylphenoxy)pyrazin-2-yl]methyl}pyrrolidin-2-one | 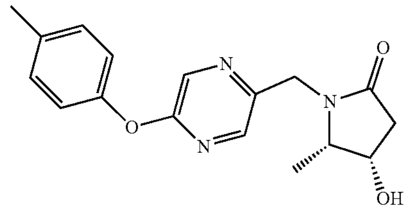 [SMILES: Cc1ccc(Oc2cnc(CN3C(=O)C[C@H](O)[C@@H]3C)cn2)cc1] | | 314.2 |
| 20 | (4S)-4-methyl-3-{[6-(4-methylphenoxy)pyridin-3-yl]methyl}-1,3-oxazolidin-2-one | 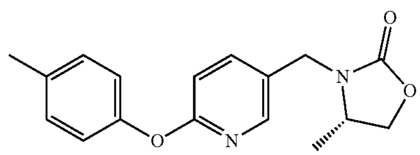 [SMILES: Cc1ccc(Oc2ccc(CN3C(=O)OC[C@@H]3C)cn2)cc1] | | 299.2 |

TABLE 1-3

| EXAMPLE | IUPACNAME | Structure | ADDITIVE | MS |
|---|---|---|---|---|
| 21 | (5S)-5-methyl-1-{[6-(4-methylphenoxy)pyridin-3-yl]methyl}pyrrolidin-2-one | 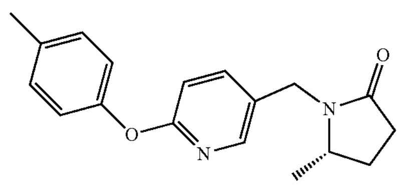 [SMILES: Cc1ccc(Oc2ccc(CN3C(=O)CC[C@@H]3C)cn2)cc1] | | 297.2 |
| 22 | (5S)-5-methyl-1-{[2-(4-methylphenoxy)pyrimidin-5-yl]methyl}pyrrolidin-2-one | 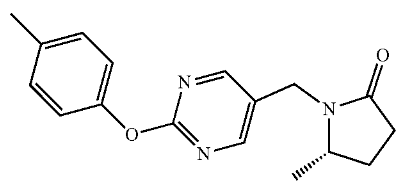 [SMILES: Cc1ccc(Oc2ncc(CN3C(=O)CC[C@@H]3C)cn2)cc1] | | 298.2 |
| 23 | (4S)-3-{[2-(2-fluoro-4-methylphenoxy)pyrimidin-5-yl]methyl}-4-methyl-1,3-oxazolidin-2-one | 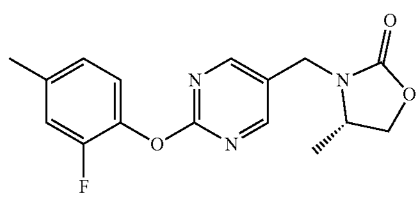 [SMILES: Cc1ccc(Oc2ncc(CN3C(=O)OC[C@@H]3C)cn2)c(F)c1] | | 318.2 |
| 24 | (4S)-4-methyl-3-{[2-(2,4,6-trifluorophenoxy)pyrimidin-5-yl]methyl}-1,3-oxazolidin-2-one | 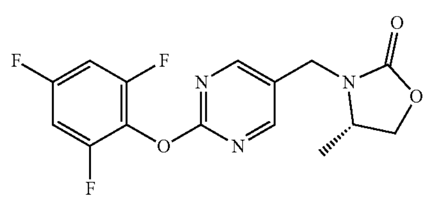 [SMILES: C[C@H]1COC(=O)N1Cc1cnc(Oc2c(F)cc(F)cc2F)nc1] | | 340.1 |
| 25 | (4S)-3-{[6-(2-fluoro-4-methylphenoxy)pyridin-3-yl]methyl}-4-methyl-1,3-oxazolidin-2-one | 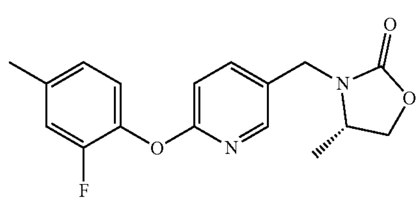 [SMILES: Cc1ccc(Oc2ccc(CN3C(=O)OC[C@@H]3C)cn2)c(F)c1] | | 317.2 |

TABLE 1-3-continued

| EXAMPLE | IUPACNAME | Structure | ADDITIVE | MS |
|---|---|---|---|---|
| 26 | (4S,5S)-1-{[6-(2-fluoro-4-methylphenoxy)pyridin-3-yl]methyl}-4-hydroxy-5-methylpyrrolidin-2-one | 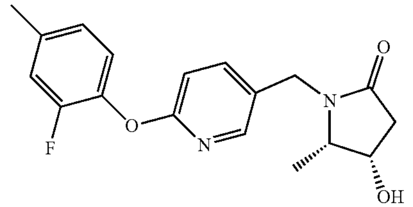 [SMILES: Cc1ccc(Oc2ccc(CN3C(=O)C[C@H](O)[C@@H]3C)cn2)c(F)c1] | | 331.2 |
| 27 | (4S,5S)-4-hydroxy-5-methyl-1-{[6-(2,4,6-trifluorophenoxy)pyridin-3-yl]methyl}pyrrolidin-2-one | 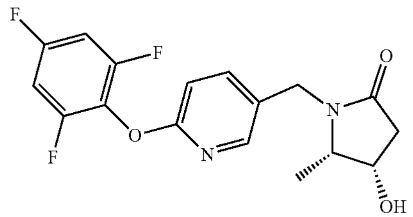 [SMILES: C[C@H]1[C@@H](O)CC(=O)N1Cc1ccc(Oc2c(F)cc(F)cc2F)nc1] | | 353.1 |
| 28 | (4S)-4-methyl-3-{[6-(2,4,6-trifluorophenoxy)pyridin-3-yl]methyl}-1,3-oxazolidin-2-one | 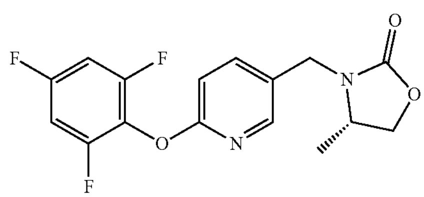 [SMILES: C[C@H]1COC(=O)N1Cc1ccc(Oc2c(F)cc(F)cc2F)nc1] | | 339.2 |
| 29 | 1-{[6-(4-methylphenoxy)pyridin-3-yl]methyl}-5-(trifluoromethyl)pyrrolidin-2-one | 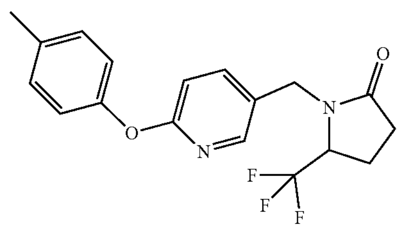 [SMILES: Cc1ccc(Oc2ccc(CN3C(=O)CCC3C(F)(F)F)cn2)cc1] | | 351.2 |
| 30 | (4S)-4-methyl-3-{[2-(4-methylphenoxy)pyrimidin-5-yl]methyl}-1,3-oxazolidin-2-one | 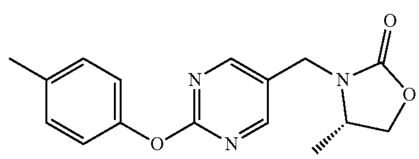 [SMILES: Cc1ccc(Oc2ncc(CN3C(=O)OC[C@@H]3C)cn2)cc1] | | 300.2 |

TABLE 1-4

| EXAMPLE | IUPACNAME | Structure | ADDITIVE | MS |
|---|---|---|---|---|
| 31 | (4S,5S)-1{[-6-(2,6-difluoro-4-methylphenoxy)pyridin-3-yl]methyl}4-hydroxy-5-methylpyrrolidin-2-one | 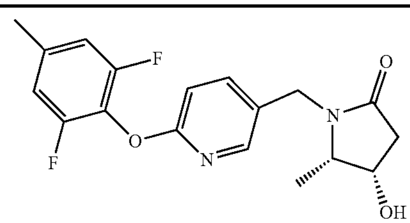 | | 349.2 |
| 32 | (4S)-3-{[2-(2,6-difluoro-4-methylphenoxy)pyrimidin-5-yl]methyl}-4-methyl-1,3-oxazolidin-2-one | 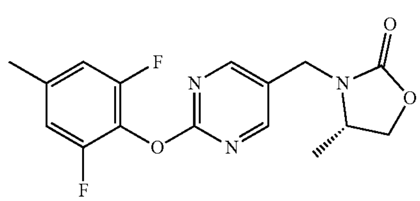 [SMILES: Cc1cc(F)c(Oc2ncc(CN3C(=O)OC[C@@H]3C)cn2)c(F)c1] | | 336.2 |

TABLE 1-4-continued

| EXAMPLE | IUPACNAME | Structure | ADDITIVE | MS |
|---|---|---|---|---|
| 33 | (5S)-5-methyl-1-{[6-(2,4,6-trifluorophenoxy)pyridin-3-yl]methyl}imidazolidin-2-one | 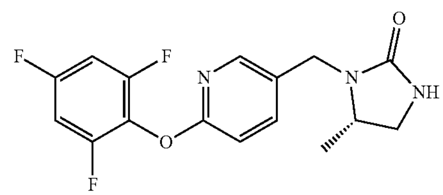 [SMILES: C[C@H]1CNC(=O)N1Cc1ccc(Oc2c(F)cc(F)cc2F)nc1] | | 338.1 |
| 34 | (4R,5S)-3,3-difluoro-4-hydroxy-5-methyl-1-{[6-(2,4,6-trifluorophenoxy)pyridin-3-yl]methyl}pyrrolidin-2-one | 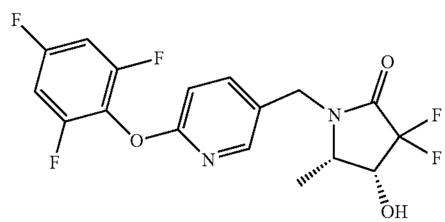 [SMILES: C[C@H]1[C@@H](O)C(F)(F)C(=O)N1Cc1ccc(Oc2c(F)cc(F)cc2F)nc1] | | 389.1 |
| 35 | (5S)-1-{[6-(2,4-difluorophenoxy)pyridin-3-yl]methyl}5-methylimidazolidin-2-one | 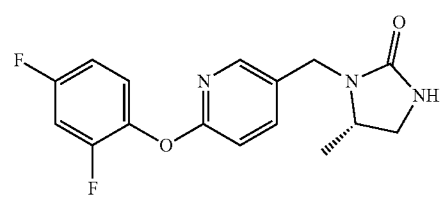 [SMILES: C[C@H]1CNC(=O)N1Cc1ccc(Oc2ccc(F)cc2F)nc1] | | 320.2 |
| 36 | (4R,5S)-1-{[6-(2,4-difluorophenoxy)pyridin-3-yl]methyl}-3,3-difluoro-4-hydroxy-5-methylpyrrolidin-2-one | 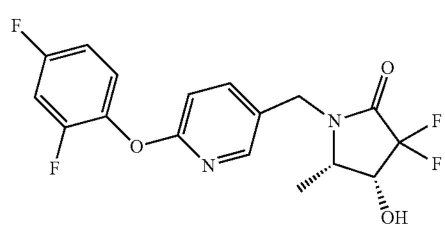 [SMILES: C[C@H]1[C@@H](O)C(F)(F)C(=O)N1Cc1ccc(Oc2ccc(F)cc2F)nc1] | | 371.1 |
| 37 | (4S,5S)-1{[-6-(2,4-difluorophenoxy)pyridin-3-yl]methyl}-4-hydroxy-5-methylpyrrolidin-2-one | 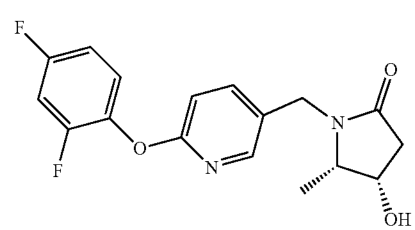 [SMILES: C[C@H]1[C@@H](O)CC(=O)N1Cc1ccc(Oc2ccc(F)cc2F)nc1] | | 335.2 |
| 38 | (4S,5S)-1-({6-[4-(difluoromethyl)-2-fluorophenoxy]pyridin-3-yl}methyl)-4-hydroxy-5-methylpyrrolidin-2-one | 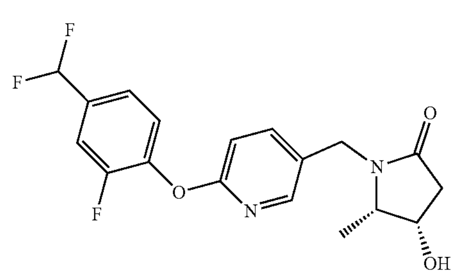 [SMILES: C[C@H]1[C@@H](O)CC(=O)N1Cc1ccc(Oc2ccc(C(F)F)cc2F)nc1] | | 367.1 |
| 39 | 4-(fluoromethyl)-3-{[6-(2-fluoro-4-methylphenoxy)pyridin-3-yl]methyl}-1,3-oxazolidin-2-one | 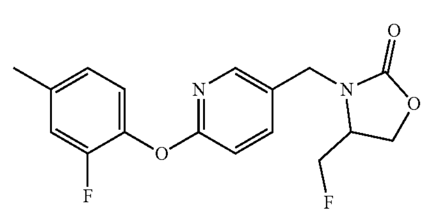 [SMILES: Cc1ccc(Oc2ccc(CN3C(=O)OCC3CF)cn2)c(F)c1] | | 335.1 |

TABLE 1-4-continued

| EXAMPLE | IUPACNAME | Structure | ADDITIVE | MS |
|---|---|---|---|---|
| 40 | 4-(difluoromethyl)-3-{[6-(2-fluoro-4-methylphenoxy)pyridin-3-yl]methyl}-1,3-oxazolidin-2-one | 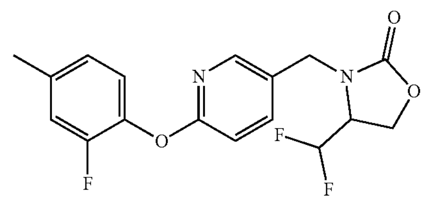 [SMILES: Cc1ccc(Oc2ccc(CN3C(=O)OCC3C(F)F)cn2)c(F)c1] | | 353.1 |

TABLE 1-5

| EXAMPLE | IUPACNAME | Structure | ADDITIVE | MS |
|---|---|---|---|---|
| 41 | (4S,5S)-1-({6-[2-fluoro-4-(trifluoromethyl)phenoxy]pyridin-3-yl}methyl)-4-hydroxy-5-methylpyrrolidin-2-one | 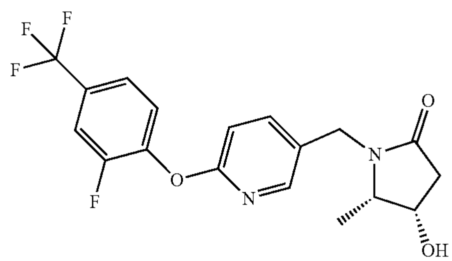 [SMILES: C[C@H]1[C@@H](O)CC(=O)N1Cc1ccc(Oc2ccc(C(F)(F)F)cc2F)nc1] | | 385.1 |
| 42 | (5S)-1-({2-[4-(difluoromethyl)-2-fluorophenoxy]pyrimidin-5-yl}methyl)-5-methylpyrrolidin-2-one | 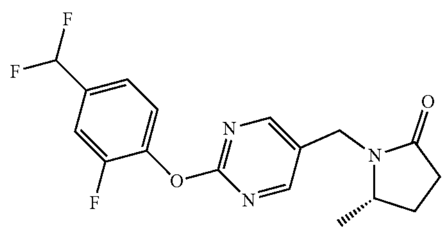 [SMILES: C[C@H]1CCC(=O)N1Cc1cnc(Oc2ccc(C(F)F)cc2F)nc1] | | 352.2 |
| 43 | (4S,5S)-1-{[6-(4-chloro-2-fluorophenoxy)pyridin-3-yl]methyl}4-hydroxy-5-methylpyrrolidin-2-one | 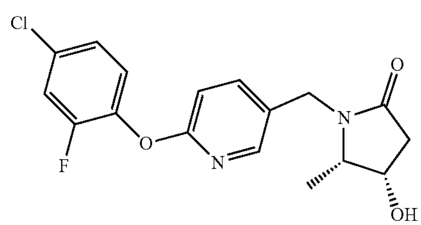 [SMILES: C[C@H]1[C@@H](O)CC(=O)N1Cc1ccc(Oc2ccc(Cl)cc2F)nc1] | | 351.1 |
| 44 | (5S)-1-{[2-(2-fluoro-4-methylphenoxy)pyrimidin-5-yl]methyl}-5-methylpyrrolidin-2-one | 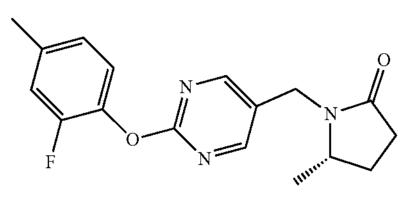 [SMILES: Cc1ccc(Oc2ncc(CN3C(=O)CC[C@@H]3C)cn2)c(F)c1] | | 316.1 |
| 45 | (5S)-1-2-{[2,4-difluorophenoxy)pyrimidin-5-yl]methyl}-methylpyrrolidin-2-one | 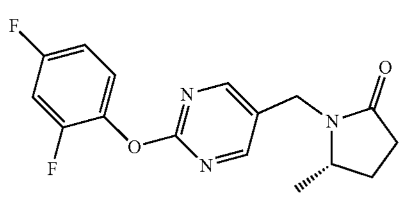 [SMILES: C[C@H]1CCC(=O)N1Cc1cnc(Oc2ccc(F)cc2F)nc1] | | 320.1 |

TABLE 1-5-continued

| EXAMPLE | IUPACNAME | Structure | ADDITIVE | MS |
|---|---|---|---|---|
| 46 | (5S)-1-{[2-(4-chloro-2-fluorophenoxy)pyrimidin-5-yl]methyl}-5-methylpyrrolidin-2-one | 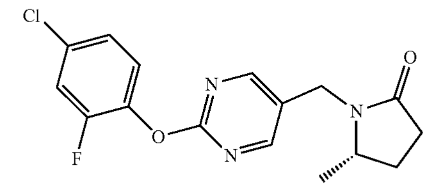 [SMILES: C[C@H]1CCC(=O)N1Cc1cnc(Oc2ccc(Cl)cc2F)nc1] | | 336.1 |
| 47 | (5S)-1-({6-[4-(difluoromethy)-2-fluorophenoxy]pyridin-3-yl}methyl)-5-methylpyrrolidin-2-one | 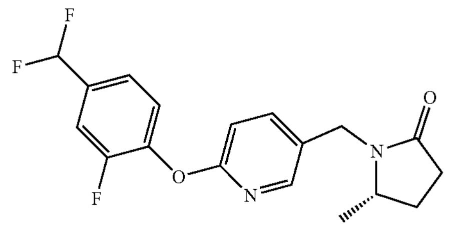 [SMILES: C[C@H]1CCC(=O)N1Cc1ccc(Oc2ccc(C(F)F)cc2F)nc1] | | 351.1 |
| 48 | (5S)-1-{[6-(2,4-difluorophenoxy)pyridin-3-yl]methyl}-5-methylpyrrolidin-2-one | 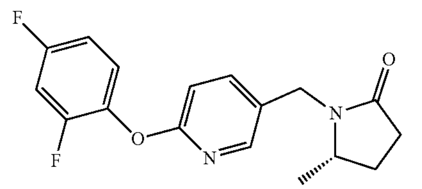 [SMILES: C[C@H]1CCC(=O)N1Cc1ccc(Oc2ccc(F)cc2F)nc1] | | 319.1 |
| 49 | (4S)-3-{[2-(4-chloro-2-fluorophenoxy)pyrimidin-5-yl]methyl}-4-methyl-1,3-oxazolidin-2-one | 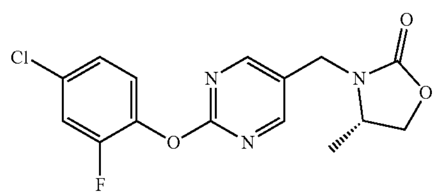 [SMILES: C[C@H]1COC(=O)N1Cc1cnc(Oc2ccc(Cl)cc2F)nc1] | | 338.1 |
| 50 | (4S)-3-({6-[4-(difluoromethyl)-2-fluorophenoxy]pyridin-3-yl}methyl)-4-methyl-1,3-oxazolidin-2-one | 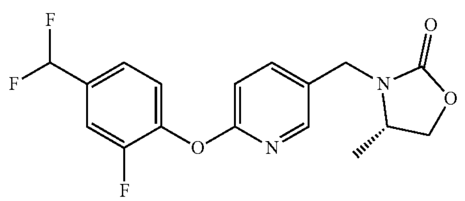 [SMILES: C[C@H]1COC(=O)N1Cc1ccc(Oc2ccc(C(F)F)cc2F)nc1] | | 353.1 |

Experimental Example 1: NR2B $Ca^{2+}$ Influx Assay

To confirm that compounds of the present disclosure exhibit antagonistic action on an NMDA receptor containing an NR2B subunit, human embryonic kidney cells expressing an NMDA receptor composed of four subunits including two sets of heterodimers of NR1 and NR2B—specifically, HEK 293 cells expressing human glutamate ionotropic receptor NMDA type subunit 1 (GRIN1) and human glutamate ionotropic receptor NMDA type subunit 2B (GRIN2B)—were used to measure an activation suppression effect on this receptor.

The HEK 293 cells that express GRIN1 and GRIN2B were purchased from ChanTest (human NMDA (NR1/NR2B) receptor-expressing, stable replicating cell line (HEK 293) catalog no. CT6121).

Intracellular calcium-ion ($Ca^{2+}$) influx caused by glycine and glutamic acid respectively binding to NR1 and NR2B was used as an index of NMDA receptor activation.

The HEK 293 cells expressing GRIN1 and GRIN2B were cultured in a cell culture flask in an incubator (37° C., in 5% $CO_2$) using a DMEM/F-12 (Cosmo Bio, 10-092-CM) medium supplemented with 10% FBS (fetal bovine serum, AusGene), 100 units/mL penicillin, 100 μg/mL streptomycin, 500 μg/mL neomycin, 100 μg/mL Zeocin (registered trademark of Invitrogen), and 5 μg/mL blasticidin.

On the day before the assay, the cells were detached from the flask by trypsinization, suspended in a seeding medium (DMEM (Invitrogen, 31053) supplemented with 10% FBS, 100 units/mL penicillin, and 100 μg/mL streptomycin) so as to be $8\times10^5$ cells/mL, seeded at 25 μL per well in a 384-well plate (Falcon, 356663) so as to be 20,000 cells/well, and cultured overnight using the incubator. On the day of the assay, tetracycline (Wako Pure Chemical, 209-16561) was diluted with the seeding medium at 2 μg/mL, and added at 25 μL/well to the plate into which the cells were seeded, and this was cultured for 2 hours in the incubator. Afterward, the medium was removed and washed with an assay buffer (137 mM NaCl, 4 mM KCl, 1.8 mM $CaCl_2$), 10 mM HEPES (pH 7.2), 10 mM glucose, 0.1% BSA) at 50 μL/well. Next, a loading buffer (buffer wherein 2.5 μM Fluo-4 AM, 2 mM amaranth, and 1 mM tartrazine are added to the assay buffer) was added at 25 μL/well, and this was incubated in the incubator for 30 minutes and for 15 minutes at room temperature. Solutions wherein the Example compounds were diluted with the above-mentioned assay buffer so as to be 30 μM (final concentration 10 μM) were added at 25 μL/well, and these were left standing for 15 minutes at room temperature. Using FDSS7000EX/μCELL (Hamamatsu Photonics), an assay buffer including 30 μM glutamic acid and 30 μM glycine was added at 25 μL/well, and a fluorescence signal of an Excitation wavelength of 480 nm and an Emission wavelength of 540 nm was measured every 3 seconds for 5 minutes. The inhibitory activity was calculated as a relative activity value (inhibitory rate) wherein relative to an integrated value of florescence values of each well, an integrated value of fluorescence values of a well into which an assay buffer without glutamic acid and glycine was defined as 100% inhibition. The results are shown in Table 2.

TABLE 2

| Example | % inhibited(10 μM) |
|---|---|
| 1 | 99 |
| 2 | 98 |
| 3 | 99 |
| 4 | 93 |
| 5 | 91 |
| 6 | 97 |
| 7 | 98 |
| 8 | 53 |
| 9 | 96 |
| 10 | 94 |
| 11 | 91 |
| 12 | 93 |
| 13 | 97 |
| 14 | 96 |
| 15 | 90 |
| 16 | 95 |
| 18 | 98 |
| 19 | 82 |
| 20 | 97 |
| 21 | 98 |
| 22 | 95 |
| 23 | 94 |
| 24 | 93 |
| 25 | 96 |
| 26 | 97 |
| 27 | 97 |
| 28 | 96 |
| 29 | 93 |
| 30 | 90 |
| 31 | 97 |
| 32 | 92 |
| 33 | 97 |
| 34 | 97 |
| 35 | 96 |
| 36 | 97 |
| 37 | 97 |
| 38 | 95 |
| 39 | 92 |
| 40 | 95 |
| 41 | 95 |
| 42 | 97 |
| 43 | 98 |
| 44 | 97 |
| 45 | 96 |
| 46 | 97 |
| 47 | 99 |
| 48 | 98 |
| 49 | 97 |
| 50 | 98 |

As indicated in Table 2 above, compounds of the present disclosure suppressed intracellular calcium-ion ($Ca^{2+}$) influx in an NMDA receptor containing an NR2B subunit. That is, it was confirmed that compounds of the present disclosure exert an antagonistic action on an NMDA receptor containing an NR2B subunit.

Experimental Example 2: [$^3$H]MK-801 Binding Test In Vivo

In order to confirm that compounds of the present disclosure exert functional antagonistic action on an NMDA receptor containing the NR2B subunit in vivo, a binding test was performed using tritium-labeled form of MK-801 ((5R,10S)-5-methyl-10,11-dihydro-5H-5,10-epiminodibenzo[a,d][7]annulene) ([$^3$H]MK-801), which is a compound capable of binding to the opening site of the NMDA receptor.

The example compound (3 mg/kg/2 mL, 0.5% MC water) or vehicle (0.5% MC water 2 ml) was orally administered (p.o.) to Sprague Dawley rats (body weight 180-260 g). After a certain time (around after time-to maximum blood concentration), [$^3$H]MK-801 (20 μCi/kg/mL, Muromachi Kikai) was intravenously administered. After 10 min, the rats were euthanized by decapitation, and subjected to craniotomy, and the hippocampus was collected. The collected hippocampus was homogenized in 30 volumes (30 mL per 1 g tissue) ice-cooled 20 mM HEPES (pH7.5, Hampton Research) using a homogenizer (T10 basic Ultra-Turrax) for 10 sec. Then, 600 μL of the homogenate was immediately filtered through GF/B Whatman glass filter (GE Health Care), which were presoaked in 0.5% polyethyleneimine (FUJIFILM Wako Pure Chemical Corporation) and set on Manifold Filtration System (Millipore) by suction. The filter was washed four times with ice-cooled saline (5 mL, Otsuka Pharmaceutical), put into a scintillation vial, and then 10 mL of liquid scintillator A (FUJIFILM Wako Pure Chemical Corporation) was added thereto, and the residual radioactivity was counted using liquid scintillation counter (ALOKA LSC-6100).

Separately, the residual radioactivity in 100 μL of the homogenate before the filtration was counted in the same way. The value of [the residual radioactivity in the filter/the residual radioactivity in the 100 μL of the homogenate] was calculated as a [$^3$H]MK-801 binding rate to the NMDA receptor expressing in each individual hippocampus tissue. Then, the [$^3$H]MK-801 binding rate in the vehicle control group was regarded as 100%, and the [$^3$H]MK-801 binding rate in the group subcutaneously administered with excess amount of MK-801 maleate (2 mg/kg/2 mL, 0.5% MC water) was regarded as 0%. The difference between the percentage of [$^3$H]MK-801 binding rate in the group orally administered with the example compound and that in the vehicle control group (100%) was analyzed as [$^3$H]MK-801 binding inhibitory rate by the example compound. The results are shown in Table 3.

TABLE 3

| Example No. | Inhibitory Rate (3 mg/kg, p.o.) |
|---|---|
| 38 | 22% |
| 45 | 13% |
| 49 | 19% |

As shown in the above-mentioned Table 3, compounds of the present disclosure inhibited the binding of [$^3$H]MK-801, which is a compound capable of binding to the opening site of the NMDA receptor containing the NR2B subunit. That is, compounds of the present disclosure were confirmed to have a functional antagonistic action on an NMDA receptor containing the NR2B subunit in vivo.

Formulation Example 1 (Production of Capsule)

| | | |
|---|---|---|
| 1) Compound of Example 1 | 30 mg | |
| 2) Fine cellulose powder | 10 mg | |
| 3) Lactose | 19 mg | |
| 4) Magnesium stearate | 1 mg | |
| Total | 60 mg | |

1), 2), 3), and 4) are mixed and filled in a gelatin capsule.

Formulation Example 2 (Production of Tablet)

| | | |
|---|---|---|
| 1) Compound of Example 1 | 30 g | |
| 2) Lactose | 50 g | |
| 3) Corn starch | 15 g | |
| 4) Carboxymethylcellulose calcium | 44 g | |
| 5) Magnesium stearate | 1 g | |
| 1,000 tablets Total | 140 g | |

The entirety of 1), 2), and 3) and 30 g of 4) are kneaded with water, vacuum-dried, and sieved. 14 g of 4) and 1 g of 5) are mixed into the sieved powder, and the mixture is punched by a tableting machine. In this manner, 1,000 tablets containing 30 mg of the compound of Example 1 per tablet are obtained.

What is claimed is:

1. A compound which is (4S)-3-{[2-(4-chloro-2-fluorophenoxy)pyrimidin-5-yl]methyl}-4-methyl-1,3-oxazolidine-2-one, or a salt thereof.

2. The compound according to claim 1, which is crystalline (4S)-3-{[2-(4-chloro-2-fluorophenoxy)pyrimidin-5-yl]methyl}-4-methyl-1,3-oxazolidine-2-one characterized by a powder X-ray diffraction pattern comprising peaks at 5.4°±0.2°, 14.0°±0.2°, 16.3°±0.2°, 17.4°±0.2°, 18.6°±0.2°, 20.3°±0.2°, 21.0°±0.2°, 21.8°±0.2°, and 24.5°±0.2° degrees two theta.

3. The compound according to claim 1, which is crystalline (4S)-3-{[2-(4-chloro-2-fluorophenoxy)pyrimidin-5-yl]methyl}-4-methyl-1,3-oxazolidine-2-one characterized by a powder X-ray diffraction pattern comprising at least three peaks at at least chosen from peaks at 5.4°±0.2°, 14.0°±0.2°, 16.3°±0.2°, 17.4°±0.2°, 18.6°±0.2°, 20.3°±0.2°, 21.0°±0.2°, 21.8°±0.2°, and 24.5°±0.2° degrees two theta.

4. The compound according to claim 1, which is crystalline (4S)-3-{[2-(4-chloro-2-fluorophenoxy)pyrimidin-5-yl]methyl}-4-methyl-1,3-oxazolidine-2-one characterized by a powder X-ray diffraction pattern comprising at least four peaks chosen from peaks at 5.4°±0.2°, 14.0°±0.2°, 16.3°±0.2°, 17.4°±0.2°, 18.6°±0.2°, 20.3°±0.2°, 21.0°±0.2°, 21.8°±0.2°, and 24.5°±0.2° degrees two theta.

5. A pharmaceutical composition comprising (4S)-3-{[2-(4-chloro-2-fluorophenoxy)pyrimidin-5-yl]methyl}-4-methyl-1,3-oxazolidine-2-one or a salt thereof and a pharmaceutically acceptable carrier.

6. A pharmaceutical composition comprising crystalline (4S)-3-{[2-(4-chloro-2-fluorophenoxy)pyrimidin-5-yl]methyl}-4-methyl-1,3-oxazolidine-2-one characterized by a powder X-ray diffraction pattern comprising peaks at 5.4°±0.2°, 14.0°±0.2°, 16.3°±0.2°, 17.4°±0.2°, 18.6°±0.2°, 20.3°±0.2°, 21.0°±0.2°, 21.8°±0.2°, and 24.5°±0.2° degrees two theta and a pharmaceutically acceptable carrier.

7. The pharmaceutical composition according to claim 5, the pharmaceutical composition comprising crystalline (4S)-3-{[2-(4-chloro-2-fluorophenoxy)pyrimidin-5-yl]methyl}-4-methyl-1,3-oxazolidine-2-one characterized by a powder X-ray diffraction pattern comprising at least three peaks chosen from peaks at 5.4°±0.2°, 14.0°±0.2°, 16.3°±0.2°, 17.4°±0.2°, 18.6°±0.2°, 20.3°±0.2°, 21.0°±0.2°, 21.8°±0.2°, and 24.5°±0.2° degrees two theta and a pharmaceutically acceptable carrier.

8. The pharmaceutical composition according to claim 5, the pharmaceutical composition comprising crystalline (4S)-3-{[2-(4-chloro-2-fluorophenoxy)pyrimidin-5-yl]methyl}-4-methyl-1,3-oxazolidine-2-one characterized by a powder X-ray diffraction pattern comprising at least four peaks chosen from peaks at 5.4°±0.2°, 14.0°±0.2°, 16.3°±0.2°, 17.4°±0.2°, 18.6°±0.2°, 20.3°±0.2°, 21.0°±0.2°, 21.8°±0.2°, and 24.5°±0.2° degrees two theta and a pharmaceutically acceptable carrier.

* * * * *